United States Patent
Gao et al.

(10) Patent No.: US 10,233,184 B2
(45) Date of Patent: Mar. 19, 2019

(54) 7-SUBSTITUTED SULFONIMIDOYLPURINONE COMPOUNDS AND DERIVATIVES FOR THE TREATMENT AND PROPHYLAXIS OF VIRUS INFECTION

(71) Applicant: Hoffmann-La Roche Inc., Little Falls, NJ (US)

(72) Inventors: Lu Gao, Shanghai (CN); Chungen Liang, Shanghai (CN); Hongying Yun, Shanghai (CN); Xiufang Zheng, Shanghai (CN); Jianping Wang, Shanghai (CN); Kun Miao, Shanghai (CN); Bo Zhang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/689,136

(22) Filed: Aug. 29, 2017

(65) Prior Publication Data
US 2018/0072730 A1     Mar. 15, 2018

(30) Foreign Application Priority Data

Aug. 29, 2016   (WO) ............... PCT/CN2016/097140
Jul. 12, 2017   (WO) ............... PCT/CN2017/092653

(51) Int. Cl.
  C07D 473/24   (2006.01)
  A61K 31/522   (2006.01)

(52) U.S. Cl.
  CPC ................. C07D 473/24 (2013.01)

(58) Field of Classification Search
  CPC ................................. C07D 473/24
  See application file for complete search history.

(56) References Cited

U.S. PATENT DOCUMENTS

| | | | |
|---|---|---|---|
| 7,642,350 | B2 | 1/2010 | Pryde et al. |
| 2010/0143301 | A1 | 6/2010 | Desai et al. |
| 2011/0150836 | A1 | 6/2011 | Halcomb et al. |

FOREIGN PATENT DOCUMENTS

| | | |
|---|---|---|
| CN | 101239980 A | 8/2008 |
| JP | 11193282 A | 7/1999 |
| WO | 98/01448 | 1/1998 |
| WO | 99/32122 | 1/1999 |
| WO | 2006/117670 A1 | 9/2006 |
| WO | 2008/0055555 A1 | 10/2008 |
| WO | 2009/005687 A1 | 8/2009 |
| WO | 201623511 | 2/2016 |
| WO | 2016/180695 A1 | 11/2016 |

OTHER PUBLICATIONS

Sepehri, Z., "The link between TLR7 signaling and hepatitis B virus infection." Life sciences 158 (2016): 63-69.*
Verweij, M. F., Preventive medicine between obligation and aspiration. vol. 4. Springer Science & Business Media, 2013.*
Hirota, K., "Discovery of 8-hydroxyadenines as a novel type of interferon inducer." Journal of medicinal chemistry 45.25 (2002): 5419-5422.*
Asselah et al., "Interferon therapy for chronic hepatitis B" Clin Liver Dis 11:839-849 ( 2007).
Connolly et al., "New developments in Tool-like receptor targeted therapeutics" Current Opinion in Pharmacology 12:510-518 ( 2012).
Gane et al., "Safety and pharmacodynamics of oral TLR-7 agonist GS-9620 in patients with chronic hepatitis B" Abstract Ann. Meeting Am. Assoc. Study Liver Dis, Washington, D.C., pp. 661A, Abstract 946 ( Nov. 2013).
Hemmi et al., "Small anti-viral compounds activate immune cells via the TLR7 MyD88-dependent signaling pathway" Nature Immunology 3(2):196 ( 2002).
Kaisho et al., "Turning NF-kB and IRFs on and off in DC" Trends in Immunology 29(7):329-336 ( 2008).
Kurimoto et al., "Prodrugs of 9-Benzyl-8-hydroxy-2-(2-hydroxyethylthio)adenine: Potent Interferon Inducing Agents in Monkeys" Chem Pharm Bull 52(4):466-469 ( 2004).
Roethle et al., "Identification and Optimization of Pteridinone Toll-like Receptor 7 (TLR7) Agonists for the Oral Treatment of Viral Hepatitis" Journal of Medicinal Chemistry 56(18):7324-7333 (Sep. 26, 2013).

* cited by examiner

*Primary Examiner* — John M Mauro
(74) *Attorney, Agent, or Firm* — Jonathan Duffield

(57) ABSTRACT

The present invention relates to compounds of formula (I),

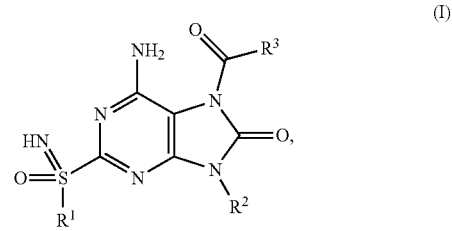

wherein $R^1$, $R^2$ and $R^3$ are as described herein, and their prodrugs or pharmaceutically acceptable salt, enantiomer or diastereomer thereof, and compositions including the compounds and methods of using the compounds.

31 Claims, 6 Drawing Sheets
Specification includes a Sequence Listing.

SEQUENCE LISTING

```
<160> NUMBER OF SEQ ID NOS: 3

<210> SEQ ID NO 1
<211> LENGTH: 20
<212> TYPE: DNA
<213> ORGANISM: Hepatitis B virus

<400> SEQUENCE: 1
aagaaaaacc ccgcctgtaa                                            20

<210> SEQ ID NO 2
<211> LENGTH: 23
<212> TYPE: DNA
<213> ORGANISM: Hepatitis B virus

<400> SEQUENCE: 2
cctgttctga ctactgcctc tcc                                        23

<210> SEQ ID NO 3
<211> LENGTH: 27
<212> TYPE: DNA
<213> ORGANISM: Hepatitis B virus

<400> SEQUENCE: 3
cctgatgtga tgttctccat gttcagc                                    27
```

7-SUBSTITUTED SULFONIMIDOYLPURINONE COMPOUNDS AND DERIVATIVES FOR THE TREATMENT AND PROPHYLAXIS OF VIRUS INFECTION

RELATED APPLICATIONS

This application claims the benefit of priority to International Application No. PCT/CN2017/092653, filed Jul. 12, 2017 and International Application No. PCT/CN2016/097140, filed Aug. 29, 2016, each of which is incorporated herein by reference in its entirety.

SEQUENCE LISTING

This application contains a Sequence Listing which has been submitted via EFS-Web and is hereby incorporated by reference in its entirety. Said ASCII copy, created on Aug. 28, 2017, is named Sequence_Listing.txt and is 902 bytes in size.

The present invention relates to novel sulfonimidoylpurinones derivatives that have in vivo Toll-like receptor agonism activity, as well as their manufacture, pharmaceutical compositions containing them and their potential use as medicaments.

FIELD OF THE INVENTION

The present invention relates to compounds of formula (I),

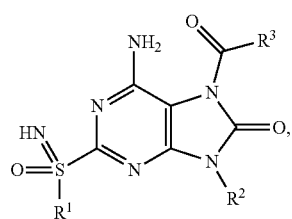

wherein $R^1$ to $R^3$ are described below, or pharmaceutically acceptable salt, enantiomer or diastereomer thereof.

Toll-like receptors (TLRs) detect a wide range of conserved pathogen-associated molecular patterns (PAMPs). They play an important role of sensing invading pathogens and subsequent initiation of innate immune responses. There are 10 known members of the TLR family in human, which are type I transmembrane proteins featuring an extracellular leucine-rich domain and a cytoplasmic tail that contains a conserved Toll/interleukin (IL)-1 receptor (TIR) domain. Within this family, TLR3, TLR7, TLR8 and TLR9 are located within endosomes. TLR7 can be activated by binding to a specific small molecule ligand (i.e., TLR7 agonist) or its native ligand (i.e., single-stranded RNA, ssRNA). Following binding of ssRNA to TLR7, the receptor in its dimerized form is believed to undergo a structural change leading to the subsequent recruitment of adapter proteins at its cytoplasmic domain, including the myeloid differentiation primary response gene 88 (MyD88). Following the initiation of the receptor signalling cascade via the MyD88 pathway, cytoplasmic transcription factors such as interferon regulatory factor 7 (IRF-7) and nuclear factor kappa B (NF-κB) are activated. These transcription factors then translocate to the nucleus and initiate the transcription of various genes, e.g., IFN-α and other antiviral cytokine genes. TLR7 is predominately expressed on plasmacytoid cells, and also on B-cells. Altered responsiveness of immune cells might contribute to the reduced innate immune responses during chronic viral infections. Agonist-induced activation of TLR7 might therefore represent a novel approach for the treatment of chronic viral infections. (D. J Connolly and L. A J O'Neill, Current Opinion in Pharmacology 2012, 12:510-518, P. A. Roethle et al, J. Med. Chem. 2013, 56, 7324-7333).

The current therapy of chronic HBV infection is based on two different types of drugs: the traditional antiviral nucleos (t)ide analogues and the more recent Pegylated INF-α (PEG-IFN-α). The oral nucleos(t)ide analogues act by suppressing the HBV replication. This is a life-long course of treatment during which drug resistance often occurs. As an alternative option, Pegylated INF-α (PEG-IFN-α) has been used to treat some chronic infected HBV patients within finite therapy duration. Although it has achieved seroconversion in HBeAg at least in a small percentage of HBV patients, the adverse effect makes it poorly tolerable. Notably, functional cure defined as HBsAg seroconversion is very rare with both current therapies. A new generation therapeutic option to treat HBV patients for a functional cure is therefore of urgent need. Treatment with an oral TLR7 agonist represents a promising solution to provide greater efficacy with better tolerability. Pegylated INF-α (PEG-IFN-α) is currently used to treat chronic HBV and is an alternative to potentially life-long treatment with antiviral nucleos(t)ide analogues. In a subset of chronic HBV patients, PEG-INF-α therapy can induce sustained immunologic control of the virus following a finite duration of therapy. However, the percentage of HBV patients that achieve seroconversion with interferon therapy is low (up to 27% for HBeAg-positive patients) and the treatment is typically poorly tolerated. Furthermore, functional cure (defined as HBsAg loss and seroconversion) is also very infrequent with both PEG-INF-α and nucleos(t)ide treatment. Given these limitations, there is an urgent need for improved therapeutic options to treat and induce a functional cure for chronic HBV. Treatment with an oral, small-molecule TLR7 agonist is a promising approach that has the potential to provide greater efficacy and tolerability (T. Asselah et al, Clin Liver Dis 2007, 11, 839-849).

In fact, several identified TLR7 agonists have been considered for therapeutic purposes. So far Imiquimod (ALDARA™) is a U.S. FDA approved TLR7 agonist drug for topical use to treat skin lesions by human papillomavirus. The TLR7/8 dual agonist resiquimod (R-848) and the TLR7 agonist 852A have been evaluated for treating human genital herpes and chemotherapy-refractory metastatic melanoma, respectively. ANA773 is an oral pro-drug TLR7 agonist, developed for the treatment of patients with chronic hepatitis C virus (HCV) infection and chronic hepatitis B infection. GS-9620 is an orally available TLR7 agonist. A phase Ib study demonstrated that treatment with GS-9620 was safe, well tolerated and resulted in dose-dependent ISG15 mRNA induction in patients with chronic hepatitis B (E. J. Gane et al, Annu Meet Am Assoc Study Liver Dis (November 1-5, Washington, D.C.) 2013, Abst 946). Therefore there is high unmet clinical need for developing potent and safe TLR7 agonists as new HBV treatment to offer more therapeutic solutions or replace existing partly effective treatment.

SUMMARY OF THE INVENTION

The present invention provides a series of novel 6-amino-2-sulfonimidoyl-9-substituted-7-substituted-purin-8-one compounds that have Toll-like receptor agonism activity and their prodrugs. The invention also provides the bio-activity of such compounds to induce SEAP level increase by activating Toll-like receptors, such as TLR7 receptor, the metabolic conversion of prodrugs to parent compounds in the presence of human hepatocytes, and the therapeutic or prophylactic use of such compounds and their pharmaceutical compositions comprising these compounds and their prodrugs to treat or prevent infectious disease like HBV or HCV. The present invention also provides compounds with superior activity. In addition, the compounds of formula (I) also show good solubility and PK profiles.

The present invention relates to novel compounds of formula (I),

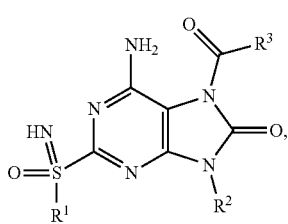

(I)

wherein
$R^1$ is $C_{1-6}$alkyl;
$R^2$ is benzyl, said benzyl being unsubstituted or substituted by one, two or three substituents independently selected from halogen and $C_{1-6}$alkyl;
$R^3$ is —$NR^4R^5$, wherein
  $R^4$ is $C_{1-6}$alkyl or $C_{1-6}$alkoxy$C_{1-6}$alkyl;
  $R^5$ is $(C_{1-6}$alkyl$)_2$NCOOC$_{1-6}$alkyl, $C_{1-6}$alkoxy$C_{1-6}$alkyl, $C_{1-6}$alkoxycarbonyl($C_{1-6}$alkyl)amino$C_{1-6}$alkyl, $C_{1-6}$alkoxycarbonyl(phenyl)$C_{1-6}$alkyl, $C_{1-6}$alkoxycarbonyl$C_{1-6}$alkyl, $C_{1-6}$alkoxycarbonyloxy$C_{1-6}$alkyl, $C_{1-6}$alkyl, $C_{1-6}$alkylcarbonyl($C_{1-6}$alkyl)amino$C_{1-6}$alkyl or pyrrolidinylcarbamoyloxy$C_{1-6}$alkyl; or
  $R^4$ and $R^5$ together with the nitrogen they are attached to form a heterocyclyl;
or pharmaceutically acceptable salt, enantiomer or diastereomer thereof;
with the proviso that
6-amino-9-benzyl-2-(propylsulfonimidoyl)-7-(pyrrolidine-1-carbonyl)purin-8-one;
6-amino-9-benzyl-7-(piperidine-1-carbonyl)-2-(propylsulfonimidoyl)purin-8-one;
6-amino-9-benzyl-7-(morpholine-4-carbonyl)-2-(propylsulfonimidoyl)purin-8-one;
6-amino-9-benzyl-7-(3,3-dimethylpyrrolidine-1-carbonyl)-2-(propyl sulfonimidoyl)purin-8-one; ethyl 1-[6-amino-9-benzyl-8-oxo-2-(propylsulfonimidoyl)purine-7-carbonyl]pyrrolidine-2-carboxylate;
6-amino-7-(2-azaspiro[3.3]heptane-2-carbonyl)-9-benzyl-2-(propylsulfonimidoyl)purin-8-one;
6-amino-9-benzyl-7-(2-oxa-6-azaspiro[3.3]heptane-6-carbonyl)-2-(propylsulfonimidoyl)purin-8-one;
6-amino-9-benzyl-7-(3,3-difluoropyrrolidine-1-carbonyl)-2-(propylsulfonimidoyl)purin-8-one;
6-amino-9-benzyl-7-(3-fluoro-3-methyl-pyrrolidine-1-carbonyl)-2-(propylsulfonimidoyl)purin-8-one;
and their enantiomers or diastereomers are excluded.

The invention also relates to their manufacture, medicaments based on a compound in accordance with the invention and their production as well as the use of compounds of formula (I) thereof as TLR7 agonist. Accordingly, the compounds of formula (I) are useful for the treatment or prophylaxis of HBV and/or HCV infection with Toll-like receptors agonism.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

Definitions

The term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl and n-propyl.

The term "$C_{1-6}$alkoxy" denotes a group of the formula $C_{1-6}$alkyl-O—. Examples of $C_{1-6}$alkoxy group include, but not limited to, methoxy, ethoxy, n-propoxy, isopropoxy, n-butoxy, isobutoxy and tert-butoxy. Particular "$C_{1-6}$alkoxy" groups are methoxy, ethoxy and isopropoxy. A more particular $C_{1-6}$alkoxy group is ethoxy.

The term "halogen" and "halo" are used interchangeably herein and denote fluoro, chloro, bromo, or iodo.

The term "heterocyclyl" denotes a monovalent saturated or partly unsaturated mono or bicyclic ring system of 3 to 10 ring atoms, comprising 1 to 5 ring heteroatoms selected from N, O and S, the remaining ring atoms being carbon. In particular embodiments, heterocyclyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, dimethylpyrrolidinyl, ethoxycarbonylpyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, dioxothiomorpholinyl, azepanyl, diazepanyl, homopiperazinyl, or oxazepanyl. Monocyclic saturated heterocyclyl can be further substituted by one to three substituents independently selected from halogen, $C_{1-6}$alkyl and $C_{1-6}$alkoxycarbonyl. Examples for substituted monocyclic saturated heterocyclyl are 4-methylpiperazinyl, dimethylpyrrolidinyl, ethoxycarbonylpyrrolidinyl, difluoropyrrolidinyl, fluoro(methyl)pyrrolidinyl. Examples for bicyclic saturated heterocyclyl are azabicyclo[3.2.1]octyl, quinuclidinyl, oxaazabicyclo[3.2.1]octyl, azabicyclo[3.3.1]nonyl, oxaazabicyclo[3.3.1]nonyl, thiaazabicyclo[3.3.1]nonyl, azaspiro[3.3]heptanyl and oxaazaspiro[3.3]heptanyl. Examples for partly unsaturated heterocyclyl are dihydrofuryl, imidazolinyl, dihydrooxazolyl, tetrahydropyridinyl and dihydropyranyl.

The term "carbonyl" alone or in combination refers to the group —C(O)—.

The term "$C_{1-6}$alkylcarbonyl" refers to a group $C_{1-6}$alkyl-C(O)—, wherein the "$C_{1-6}$alkyl" is as defined above. Particular "$C_{1-6}$alkylcarbonyl" group is acetyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) and their prodrugs which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The term "prodrug" denotes a form or derivative of a compound which is metabolized in vivo, e.g., by biological fluids or enzymes by a subject after administration, into a pharmacologically active form of the compound in order to produce the desired pharmacological effect. Prodrugs are described e.g. in "The Organic Chemistry of Drug Design and Drug Action", by Richard B. Silverman, Academic Press, San Diego, 2004, Chapter 8 Prodrugs and Drug Delivery Systems, pp. 497-558.

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

TLR7 Agonist and Prodrug

The present invention relates to a compound of formula (I),

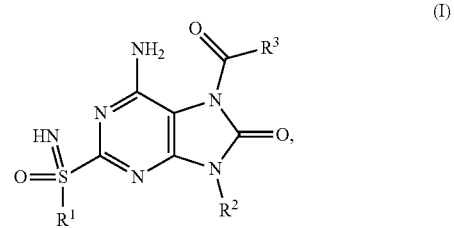

wherein
$R^1$ is $C_{1-6}$alkyl;
$R^2$ is benzyl, said benzyl being unsubstituted or substituted by one, two or three substituents independently selected from halogen and $C_{1-6}$alkyl;
$R^3$ is —$NR^4R^5$, wherein
  $R^4$ is $C_{1-6}$alkyl or $C_{1-6}$alkoxy$C_{1-6}$alkyl;
  $R^5$ is $(C_{1-6}$alkyl$)_2$NCOOC$_{1-6}$alkyl, $C_{1-6}$alkoxy$C_{1-6}$alkyl, $C_{1-6}$alkoxycarbonyl($C_{1-6}$alkyl)amino$C_{1-6}$alkyl, $C_{1-6}$alkoxycarbonyl(phenyl)$C_{1-6}$alkyk $C_{1-6}$alkoxycarbonyl$C_{1-6}$alkyl, $C_{1-6}$alkoxycarbonyloxy$C_{1-6}$alkyl, $C_{1-6}$alkyl, $C_{1-6}$alkylcarbonyl($C_{1-6}$alkyl)amino$C_{1-6}$alkyl or pyrrolidinylcarbamoyloxy$C_{1-6}$alkyl; or
  $R^4$ and $R^5$ together with the nitrogen they are attached to form a heterocyclyl;
or pharmaceutically acceptable salt, enantiomer or diastereomer thereof;
with the proviso that
6-amino-9-benzyl-2-(propylsulfonimidoyl)-7-(pyrrolidine-1-carbonyl)purin-8-one;
6-amino-9-benzyl-7-(piperidine-1-carbonyl)-2-(propylsulfonimidoyl)purin-8-one;
6-amino-9-benzyl-7-(morpholine-4-carbonyl)-2-(propylsulfonimidoyl)purin-8-one;
6-amino-9-benzyl-7-(3,3-dimethylpyrrolidine-1-carbonyl)-2-(propylsulfonimidoyl)purin-8-one;
ethyl 1-[6-amino-9-benzyl-8-oxo-2-(propylsulfonimidoyl)purine-7-carbonyl]pyrrolidine-2-carboxylate;
6-amino-7-(2-azaspiro[3.3]heptane-2-carbonyl)-9-benzyl-2-(propylsulfonimidoyl)purin-8-one;

6-amino-9-benzyl-7-(2-oxa-6-azaspiro[3.3]heptane-6-carbonyl)-2-(propylsulfonimidoyl)purin-8-one;
6-amino-9-benzyl-7-(3,3-difluoropyrrolidine-1-carbonyl)-2-(propylsulfonimidoyl)purin-8-one;
6-amino-9-benzyl-7-(3-fluoro-3-methyl-pyrrolidine-1-carbonyl)-2-(propylsulfonimidoyl)purin-8-one;
and their enantiomers or diastereomers are excluded.

A further embodiment of present invention is (ii) a compound of formula (I), wherein
$R^1$ is $C_{1-6}$alkyl;
$R^2$ is benzyl, said benzyl being unsubstituted or substituted by halogen or $C_{1-6}$alkyl;
$R^3$ is azetidinyl;
piperazinyl substituted by $C_{1-6}$alkyl;
piperidinyl substituted by piperidinyl;
pyrrolidinyl; or
—$NR^4R^5$, wherein
$R^4$ is $C_{1-6}$alkyl or $C_{1-6}$alkoxy$C_{1-6}$alkyl;
$R^5$ is $(C_{1-6}alkyl)_2NCOOC_{1-6}$alkyl, $C_{1-6}$alkoxy$C_{1-6}$alkyl, $C_{1-6}$alkoxycarbonyl$(C_{1-6}$alkyl)amino$C_{1-6}$alkyl, $C_{1-6}$alkoxycarbonyl(phenyl)$C_{1-6}$alkyl, $C_{1-6}$alkoxycarbonyl$C_{1-6}$alkyl, $C_{1-6}$alkoxycarbonyloxy$C_{1-6}$alkyl, $C_{1-6}$alkyl, $C_{1-6}$alkylcarbonyl$(C_{1-6}$alkyl)amino$C_{1-6}$alkyl or pyrrolidinylcarbamoyloxy$C_{1-6}$alkyl;
or pharmaceutically acceptable salt, enantiomer or diastereomer thereof.

A further embodiment of present invention is (iii) a compound of formula (I), wherein
$R^1$ is ethyl or propyl;
$R^2$ is benzyl, bromobenzyl, chlorobenzyl, fluorobenzyl or methylbenzyl;
$R^3$ is azetidinyl;
4-methylpiperazinyl;
piperidinylpiperidinyl;
pyrrolidinyl; or
—$NR^4R^5$, wherein
$R^4$ is methyl, ethyl, propyl or methoxyethyl;
$R^5$ is acetyl(methyl)aminoethyl, butyl, butyl(methyl)carbamoyloxyethyl, diethylcarbamoyloxyethyl, ethoxycarbonyl(methyl)aminoethyl, ethoxycarbonylethyl, ethoxycarbonylisobutyl, ethoxycarbonylisopentyl, ethoxycarbonylmethyl, ethoxycarbonyloxyethyl, ethoxycarbonyl(phenyl)ethyl, ethyl, isobutyl, isopropoxycarbonylisopentyl, isopropoxycarbonyl(phenyl)ethyl, isopropyl, methoxycarbonyl(methyl)aminoethyl, methoxyethyl, methoxypropyl, propyl, propyl(methyl)carbamoyloxyethyl, pyrrolidinylcarbamoyloxyethyl, tert-butoxycarbonyl(methyl)aminoethyl, tert-butoxycarbonyl ethyl, tert-butoxycarbonylisopentyl or tert-butoxycarbonyl(phenyl)ethyl;
or pharmaceutically acceptable salt, enantiomer or diastereomer thereof.

A further embodiment of present invention is (iii-1) a compound of formula (I), wherein
$R^1$ is ethyl or propyl;
$R^2$ is benzyl, chlorobenzyl, fluorobenzyl or methylbenzyl;
$R^3$ is azetidinyl;
4-methylpiperazinyl;
piperidinylpiperidinyl;
pyrrolidinyl; or
—$NR^4R^5$, wherein
$R^4$ is methyl, ethyl, propyl or methoxyethyl;
$R^5$ is acetyl(methyl)aminoethyl, butyl, butyl(methyl)carbamoyloxyethyl, diethylcarbamoyloxyethyl, ethoxycarbonyl(methyl)aminoethyl, ethoxycarbonylethyl, ethoxycarbonylisobutyl, ethoxycarbonylisopentyl, ethoxycarbonylmethyl, ethoxycarbonyloxyethyl, ethoxycarbonyl(phenyl)ethyl, ethyl, isobutyl, isopropoxycarbonylisopentyl, isopropoxycarbonyl(phenyl)ethyl, isopropyl, methoxycarbonyl(methyl)aminoethyl, methoxyethyl, methoxypropyl, propyl, propyl(methyl)carbamoyloxyethyl, pyrrolidinylcarbamoyloxyethyl, tert-butoxycarbonyl(methyl)aminoethyl, tert-butoxycarbonyl ethyl, tert-butoxycarbonylisopentyl or tert-butoxycarbonyl(phenyl)ethyl;
or pharmaceutically acceptable salt, enantiomer or diastereomer thereof.

A further embodiment of present invention is (iv) a compound of formula (I), wherein $R^3$ is azetidinyl, 4-methylpiperazinyl, piperidinylpiperidinyl, pyrrolidinyl, acetyl(methyl)aminoethyl(methyl)amino, bis(methoxyethyl)amino, butyl(ethyl)amino, butyl(methyl)amino, butyl(methyl)carbamoyloxyethyl(methyl)amino, diethylcarbamoyloxyethyl(methyl)amino, ethoxycarbonyl(methyl)aminoethyl(methyl)amino, ethoxycarbonylethyl(methyl)amino, ethoxycarbonylisobutyl(methyl)amino, ethoxycarbonylisopentyl(methyl)amino, ethoxycarbonylmethyl(methyl)amino, ethoxycarbonyloxyethyl(methyl)amino, ethoxycarbonyl(phenyl)ethyl(methyl)amino, ethyl(methyl)amino, isobutyl(methyl)amino, isopropoxycarbonylisopentyl(methyl)amino, isopropoxycarbonyl(phenyl)ethyl(methyl)amino, isopropyl(methyl)amino, methoxycarbonyl(methyl)aminoethyl(methyl)amino, methoxyethyl(ethyl)amino, methoxyethyl(methyl)amino, methoxyethyl(propyl)amino, methoxypropyl(methyl)amino, propyl(ethyl)amino, propyl(methyl)amino, propyl(methyl)carbamoyloxyethyl(methyl)amino, pyrrolidinylcarbamoyloxyethyl(methyl)amino, tert-butoxycarbonyl(methyl)aminoethyl(methyl)amino, tert-butoxycarbonylethyl(methyl)amino, tert-butoxycarbonylisopentyl(methyl)amino or tert-butoxycarbonyl(phenyl)ethyl(methyl)amino;
or pharmaceutically acceptable salt, enantiomer or diastereomer thereof.

A further embodiment of present invention is (v) a compound of formula (I), wherein $R^1$ is ethyl.

A further embodiment of present invention is (vi) a compound of formula (I), wherein $R^2$ is benzyl substituted by halogen or $C_{1-6}$alkyl.

A further embodiment of present invention is (vii) a compound of formula (I), wherein $R^2$ is bromobenzyl, chlorobenzyl, fluorobenzyl or methylbenzyl.

A further embodiment of present invention is (vii-1) a compound of formula (I), wherein $R^2$ is chlorobenzyl, fluorobenzyl or methylbenzyl.

A further embodiment of present invention is (viii) a compound of formula (I), wherein $R^2$ is bromobenzyl, chlorobenzyl or fluorobenzyl.

A further embodiment of present invention is (viii-1) a compound of formula (I), wherein $R^2$ is chlorobenzyl or fluorobenzyl.

A further embodiment of present invention is (ix) a compound of formula (I), wherein $R^3$ is —$NR^4R^5$, wherein $R^4$ is $C_{1-6}$alkyl, $R^5$ is $C_{1-6}$alkyl.

A further embodiment of present invention is (x) a compound of formula (I), wherein $R^3$ is propyl(methyl)amino or ethyl(methyl)amino.

A further embodiment of present invention is (xi) a compound of formula (I), wherein
$R^1$ is $C_{1-6}$alkyl;
$R^2$ is benzyl, said benzyl being substituted by halogen or $C_{1-6}$alkyl;
$R^3$ is —$NR^4R^5$, wherein $R^4$ is $C_{1-6}$alkyl, $R^5$ is $C_{1-6}$alkyl;

or pharmaceutically acceptable salt, enantiomer or diastereomer thereof.

A further embodiment of present invention is (xii) a compound of formula (I), wherein
$R^1$ is ethyl;
$R^2$ is methylbenzyl, bromobenzyl, chlorobenzyl or fluorobenzyl;
$R^3$ is propyl(methyl)amino or ethyl(methyl)amino;
or pharmaceutically acceptable salt, enantiomer or diastereomer thereof.

A further embodiment of present invention is (xii-1) a compound of formula (I), wherein
$R^1$ is ethyl;
$R^2$ is methylbenzyl, chlorobenzyl or fluorobenzyl;
$R^3$ is propyl(methyl)amino or ethyl(methyl)amino;
or pharmaceutically acceptable salt, enantiomer or diastereomer thereof.

Another embodiment of present invention is that (xiii) particular compounds of formula (I) are the following:

6-Amino-9-benzyl-N-methyl-8-oxo-N-propyl-2-(propylsulfonimidoyl)purine-7-carboxamide;
6-Amino-9-benzyl-N-(2-methoxyethyl)-N-methyl-8-oxo-2-(propyl sulfonimidoyl)purine-7-carboxamide;
6-Amino-9-benzyl-N-ethyl-8-oxo-N-propyl-2-(propylsulfonimidoyl)purine-7-carboxamide;
6-Amino-9-benzyl-7-[4-(1-piperidyl)piperidine-1-carbonyl]-2-(propylsulfonimidoyl)purin-8-one;
6-Amino-9-benzyl-N-ethyl-N-(2-methoxyethyl)-8-oxo-2-(propylsulfonimidoyl)purine-7-carboxamide;
6-Amino-9-benzyl-N-butyl-N-ethyl-8-oxo-2-(propylsulfonimidoyl)purine-7-carboxamide;
6-Amino-9-benzyl-N-(2-methoxyethyl)-8-oxo-N-propyl-2-(propyl sulfonimidoyl)purine-7-carboxamide;
6-Amino-9-benzyl-N,N-bis(2-methoxyethyl)-8-oxo-2-(propylsulfonimidoyl)purine-7-carboxamide;
6-Amino-7-(azetidine-1-carbonyl)-9-benzyl-2-(propylsulfonimidoyl)purin-8-one;
6-Amino-9-benzyl-N-isopropyl-N-methyl-8-oxo-2-(propylsulfonimidoyl)purine-7-carboxamide;
6-Amino-9-benzyl-7-(4-methylpiperazine-1-carbonyl)-2-(propylsulfonimidoyl)purin-8-one;
6-Amino-9-benzyl-N-(3-methoxypropyl)-N-methyl-8-oxo-2-(propylsulfonimidoyl)purine-7-carboxamide;
6-Amino-9-benzyl-N-isobutyl-N-methyl-8-oxo-2-(propylsulfonimidoyl)purine-7-carboxamide;
Ethyl 2-[[6-amino-9-benzyl-8-oxo-2-(propylsulfonimidoyl)purine-7-carbonyl]-methyl-amino]acetate;
Ethyl 3-[[6-amino-9-benzyl-8-oxo-2-(propylsulfonimidoyl)purine-7-carbonyl]-methyl-amino]propanoate;
tert-Butyl 3-[[6-amino-9-benzyl-8-oxo-2-(propylsulfonimidoyl)purine-7-carbonyl]-methyl-amino]propanoate;
Ethyl (2S)-2-[[6-amino-9-benzyl-8-oxo-2-(propylsulfonimidoyl)purine-7-carbonyl]-methyl-amino]propanoate;
tert-Butyl (2S)-2-[[6-amino-9-benzyl-8-oxo-2-(propylsulfonimidoyl)purine-7-carbonyl]-methyl-amino]-4-methylpentanoate;
Isopropyl (2S)-2-[[6-amino-9-benzyl-8-oxo-2-(propylsulfonimidoyl)purine-7-carbonyl]-methyl-amino]-4-methylpentanoate;
Ethyl (2S)-2-[[6-amino-9-benzyl-8-oxo-2-(propylsulfonimidoyl)purine-7-carbonyl]-methyl-amino]-3-methyl-butanoate;
Ethyl (2S)-2-[[6-amino-9-benzyl-8-oxo-2-(propylsulfonimidoyl)purine-7-carbonyl]-methyl-amino]-4-methylpentanoate;
Ethyl (2S)-2-[[6-amino-9-benzyl-8-oxo-2-(propylsulfonimidoyl)purine-7-carbonyl]-methyl-amino]-3-phenylpropanoate;
Isopropyl (2S)-2-[[6-amino-9-benzyl-8-oxo-2-(propylsulfonimidoyl)purine-7-carbonyl]-methyl-amino]-3-phenylpropanoate;
tert-Butyl (2S)-2-[[6-amino-9-benzyl-8-oxo-2-(propylsulfonimidoyl)purine-7-carbonyl]-methyl-amino]-3-phenylpropanoate;
N-[2-[Acetyl(methyl)amino]ethyl]-6-amino-9-benzyl-N-methyl-8-oxo-2-(propylsulfonimidoyl)purine-7-carboxamide;
Methyl N-[2-[[6-amino-9-benzyl-8-oxo-2-(propylsulfonimidoyl)purine-7-carbonyl]-methyl-amino]ethyl]-N-methyl-carbamate;
tert-Butyl N-[2-[[6-amino-9-benzyl-8-oxo-2-(propylsulfonimidoyl)purine-7-carbonyl]-methyl-amino]ethyl]-N-methyl-carbamate;
Ethyl N-[2-[[6-amino-9-benzyl-8-oxo-2-(propylsulfonimidoyl)purine-7-carbonyl]-methyl-amino]ethyl]-N-methyl-carbamate;
2-[[6-Amino-9-benzyl-8-oxo-2-(propylsulfonimidoyl)purine-7-carbonyl]-methyl-amino]ethyl N-butyl-N-methyl-carbamate;
2-[[6-Amino-9-benzyl-8-oxo-2-(propylsulfonimidoyl)purine-7-carbonyl]-methyl-amino]ethyl pyrrolidine-1-carboxylate;
2-[[6-Amino-9-benzyl-8-oxo-2-(propylsulfonimidoyl)purine-7-carbonyl]-methyl-amino]ethyl N-methyl-N-propyl-carbamate;
2-[[6-Amino-9-benzyl-8-oxo-2-(propylsulfonimidoyl)purine-7-carbonyl]-methyl-amino]ethyl N,N-diethylcarbamate;
2-[[6-Amino-9-benzyl-8-oxo-2-(propylsulfonimidoyl)purine-7-carbonyl]-methyl-amino]ethyl ethyl carbonate;
6-Amino-N-butyl-9-[(4-chlorophenyl)methyl]-N-methyl-8-oxo-2-[S(S)-propylsulfonimidoyl]purine-7-carboxamide;
6-amino-N-butyl-9-[(4-chlorophenyl)methyl]-N-methyl-8-oxo-2-[S(S)-propylsulfonimidoyl]purine-7-carboxamide;
6-Amino-9-[(4-chlorophenyl)methyl]-N-ethyl-N-methyl-8-oxo-2-(propylsulfonimidoyl)purine-7-carboxamide;
6-Amino-N-methyl-8-oxo-N-propyl-2[S(S)-propylsulfonimidoyl]-9-(p-tolylmethyl)purine-7-carboxamide;
6-Amino-N-methyl-8-oxo-N-propyl-2[S(R)-propylsulfonimidoyl]-9-(p-tolylmethyl)purine-7-carboxamide;
6-Amino-2-[S(S)-propylsulfonimidoyl]-9-(p-tolylmethyl)-7-(pyrrolidine-1-carbonyl)purin-8-one;
6-Amino-2-[S(R)-propylsulfonimidoyl]-9-(p-tolylmethyl)-7-(pyrrolidine-1-carbonyl)purin-8-one;
6-Amino-N-(2-methoxyethyl)-N-methyl-8-oxo-2-[S(S)-propylsulfonimidoyl]-9-(p-tolylmethyl)purine-7-carboxamide;
6-Amino-N-(2-methoxyethyl)-N-methyl-8-oxo-2-[S(R)-propylsulfonimidoyl]-9-(p-tolylmethyl)purine-7-carboxamide;
6-Amino-N-ethyl-N-methyl-8-oxo-2-(propylsulfonimidoyl)-9-(p-tolylmethyl)purine-7-carboxamide;
6-Amino-N-butyl-N-methyl-8-oxo-2-(propylsulfonimidoyl)-9-(p-tolylmethyl)purine-7-carboxamide;
6-Amino-9-[(4-chlorophenyl)methyl]-2-[S(R)-ethylsulfonimidoyl]-N-methyl-8-oxo-N-propyl-purine-7-carboxamide;
6-Amino-9-[(4-chlorophenyl)methyl]-2-[S(S)-ethylsulfonimidoyl]-N-methyl-8-oxo-N-propyl-purine-7-carboxamide;
6-Amino-9-[(4-chlorophenyl)methyl]-N-ethyl-2[S(S)-ethylsulfonimidoyl]-N-methyl-8-oxo-purine-7-carboxamide;
6-Amino-9-[(4-chlorophenyl)methyl]-N-ethyl-2-[S(R)-ethylsulfonimidoyl]-N-methyl-8-oxo-purine-7-carboxamide;
6-Amino-2-[S(S)-ethylsulfonimidoyl]-N-methyl-8-oxo-N-propyl-9-(p-tolylmethyl)purine-7-carboxamide;

6-Amino-2-[S(R)-ethylsulfonimidoyl]-N-methyl-8-oxo-N-propyl-9-(p-tolylmethyl)purine-7-carboxamide;
6-Amino-N-ethyl-2[S(S)-ethylsulfonimidoyl]-N-methyl-8-oxo-9-(p-tolylmethyl)purine-7-carboxamide;
6-Amino-N-ethyl-2-[S(R)-ethylsulfonimidoyl]-N-methyl-8-oxo-9-(p-tolylmethyl)purine-7-carboxamide;
6-Amino-2-[S(S)ethylsulfonimidoyl]-9-[(4-fluorophenyl)methyl]-N-methyl-8-oxo-N-propyl-purine-7-carboxamide;
6-Amino-2-[S(R)ethylsulfonimidoyl]-9-[(4-fluorophenyl)methyl]-N-methyl-8-oxo-N-propyl-purine-7-carboxamide;
6-Amino-N-ethyl-2-(ethylsulfonimidoyl)-9-[(4-fluorophenyl)methyl]-N-methyl-8-oxo-purine-7-carboxamide;
6-Amino-N-ethyl-2-[S(S)-(ethylsulfonimidoyl)]-9-[(4-fluorophenyl)methyl]-N-methyl-8-oxo-purine-7-carboxamide;
6-Amino-N-ethyl-2-[S(R)-(ethylsulfonimidoyl)]-9-[(4-fluorophenyl)methyl]-N-methyl-8-oxo-purine-7-carboxamide;
6-Amino-9-[(4-bromophenyl)methyl]-2-(ethylsulfonimidoyl)-N-methyl-8-oxo-N-propyl-purine-7-carboxamide;
6-Amino-2-[S(R)-ethylsulfonimidoyl]-9-[(4-bromophenyl)methyl]-N-methyl-8-oxo-N-propyl-purine-7-carboxamide;
6-Amino-2-[S(S)-ethylsulfonimidoyl]-9-[(4-bromophenyl)methyl]-N-methyl-8-oxo-N-propyl-purine-7-carboxamide;
6-Amino-9-[(4-bromophenyl)methyl]-N-ethyl-2-(ethylsulfonimidoyl)-N-methyl-8-oxo-purine-7-carboxamide;
6-Amino-9-[(4-bromophenyl)methyl]-N-ethyl-2-[S(S)-(ethylsulfonimidoyl)]-N-methyl-8-oxo-purine-7-carboxamide; and
6-Amino-9-[(4-bromophenyl)methyl]-N-ethyl-2-[S(R)-(ethylsulfonimidoyl)]-N-methyl-8-oxo-purine-7-carboxamide;

or pharmaceutically acceptable salt, enantiomer or diastereomer thereof.

Another embodiment of present invention is that (xiv) more particular compounds of formula (I) are the following:
6-Amino-9-benzyl-N-methyl-8-oxo-N-propyl-2-(propylsulfonimidoyl)purine-7-carboxamide;
6-Amino-9-[(4-chlorophenyl)methyl]-2-[ S(R)-ethylsulfonimidoyl]-N-methyl-8-oxo-N-propyl-purine-7-carboxamide;
6-Amino-9-[(4-chlorophenyl)methyl]-2-[S(S)-ethylsulfonimidoyl]-N-methyl-8-oxo-N-propyl-purine-7-carboxamide;
6-Amino-9-[(4-chlorophenyl)methyl]-N-ethyl-2[S(S)-ethylsulfonimidoyl]-N-methyl-8-oxo-purine-7-carboxamide;
6-Amino-9-[(4-chlorophenyl)methyl]-N-ethyl-2-[S(R)-ethylsulfonimidoyl]-N-methyl-8-oxo-purine-7-carboxamide;
6-Amino-2-[S(S)-ethylsulfonimidoyl]-N-methyl-8-oxo-N-propyl-9-(p-tolylmethyl)purine-7-carboxamide;
6-Amino-2-[S(R)-ethylsulfonimidoyl]-N-methyl-8-oxo-N-propyl-9-(p-tolylmethyl)purine-7-carboxamide;
6-Amino-N-ethyl-2[S(S)-ethylsulfonimidoyl]-N-methyl-8-oxo-9-(p-tolylmethyl)purine-7-carboxamide;
6-Amino-N-ethyl-2-[S(R)-ethylsulfonimidoyl]-N-methyl-8-oxo-9-(p-tolylmethyl)purine-7-carboxamide;
6-amino-2-(ethylsulfonimidoyl)-9-[(4-fluorophenyl)methyl]-N-methyl-8-oxo-N-propyl-purine-7-carboxamide;
6-Amino-2-[S(S)ethylsulfonimidoyl]-9-[(4-fluorophenyl)methyl]-N-methyl-8-oxo-N-propyl-purine-7-carboxamide;
6-Amino-2-[S(R)ethylsulfonimidoyl]-9-[(4-fluorophenyl)methyl]-N-methyl-8-oxo-N-propyl-purine-7-carboxamide;
6-Amino-N-ethyl-2-(ethylsulfonimidoyl)-9-[(4-fluorophenyl)methyl]-N-methyl-8-oxo-purine-7-carboxamide;
6-Amino-N-ethyl-2-[S(S)-(ethylsulfonimidoyl)]-9-[(4-fluorophenyl)methyl]-N-methyl-8-oxo-purine-7-carboxamide;
6-Amino-N-ethyl-2-[S(R)-(ethylsulfonimidoyl)]-9-[(4-fluorophenyl)methyl]-N-methyl-8-oxo-purine-7-carboxamide;
6-Amino-9-[(4-bromophenyl)methyl]-2-(ethylsulfonimidoyl)-N-methyl-8-oxo-N-propyl-purine-7-carboxamide;
6-Amino-2-[S(R)-ethylsulfonimidoyl]-9-[(4-bromophenyl)methyl]-N-methyl-8-oxo-N-propyl-purine-7-carboxamide;
6-Amino-2-[S(S)-ethylsulfonimidoyl]-9-[(4-bromophenyl)methyl]-N-methyl-8-oxo-N-propyl-purine-7-carboxamide;
6-Amino-9-[(4-bromophenyl)methyl]-N-ethyl-2-(ethylsulfonimidoyl)-N-methyl-8-oxo-purine-7-carboxamide;
6-Amino-9-[(4-bromophenyl)methyl]-N-ethyl-2-[S(S)-(ethylsulfonimidoyl)]-N-methyl-8-oxo-purine-7-carboxamide; and
6-Amino-9-[(4-bromophenyl)methyl]-N-ethyl-2-[S(R)-(ethylsulfonimidoyl)]-N-methyl-8-oxo-purine-7-carboxamide;

or pharmaceutically acceptable salt, enantiomer or diastereomer thereof.

In some embodiments, compounds of present invention were tested and compared with the following reference compounds. As the most successful biopharmaceutical companies focusing on discovery and development of TLR7 agonists for treating liver diseases, Gilead has the most advanced TLR7 agonist pipeline with leading compounds such as GS-9620 which has entered into Phase II studies. Gilead compound GS-9620 disclosed in US20100143301 as example 49, compound S-2 and compound S-3 disclosed in JP1999193282 were all chosen as the reference compounds in this application:

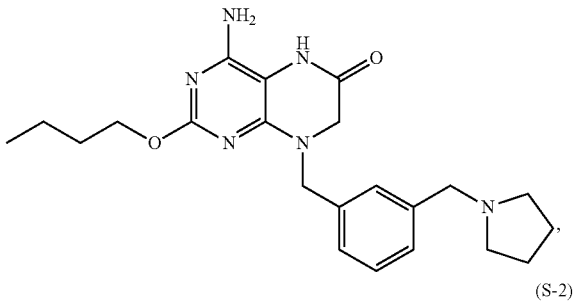
(GS-9620)

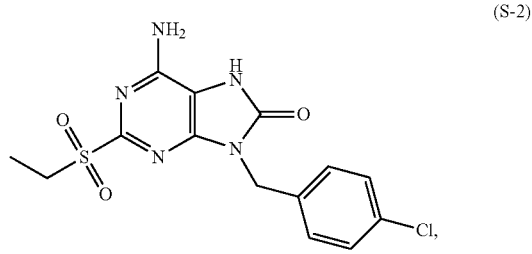
(S-2)

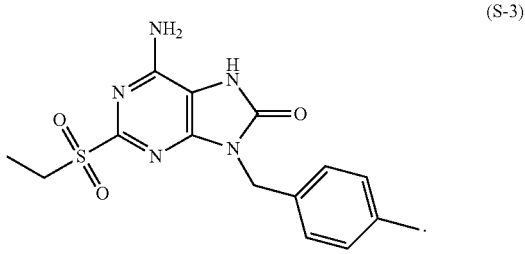
(S-3)

Synthesis

The compounds of the present invention can be prepared by any conventional means. Suitable processes for synthesizing these compounds as well as their starting materials are provided in the schemes below and in the examples. All substituents, in particular, $R^1$ to $R^{14}$ are as defined above unless otherwise indicated. Furthermore, and unless explicitly otherwise stated, all reactions, reaction conditions, abbreviations and symbols have the meanings well known to a person of ordinary skill in organic chemistry.

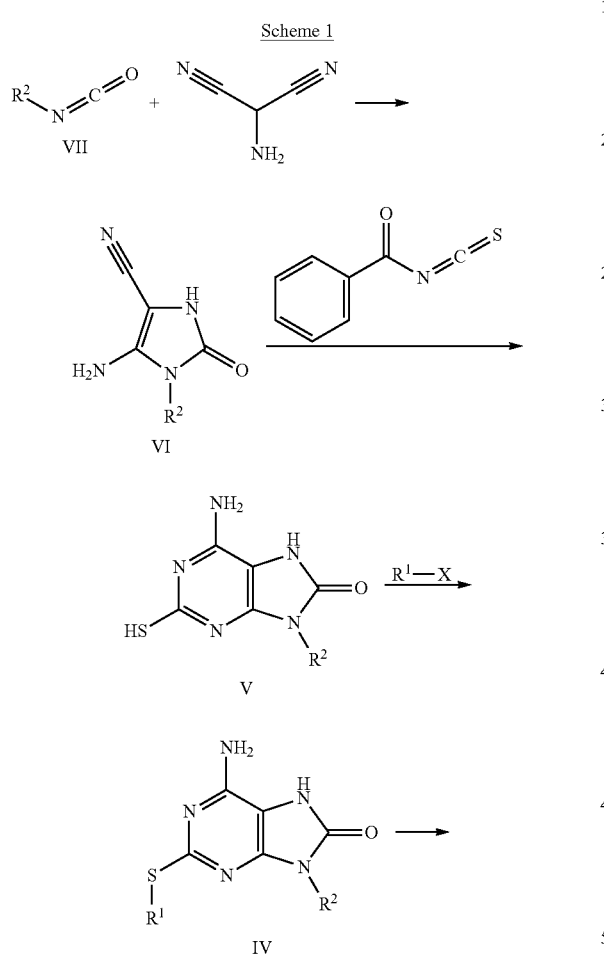

A compound of formula VI is prepared by cyclization of isocyanate VII with aminomalononitrilep-toluenesulfonate. Then bicycle V is synthesized by reaction of compound of formula VI with benzoyl isothiocyanate in the presence of inorganic base, such as NaOH or KOH. Alkylation of bicycle V with alkylhalide in the presence of base, such as $K_2CO_3$, NaH or $Cs_2CO_3$, gives compound of formula IV. Compound of formula III is prepared by oxidation of compound of formula IV with an oxidant, such as meta-chloroperoxybenzoic acid, urea-hydrogen peroxide adduct and $HIO_4$. Compound of formula II is obtained by imination of compound of formula III with imination reagent, such as sodium azide in acid, said acid is, for example, Eaton's reagent or PPA. Compound of formula I is obtained by reaction of compound of formula II with carbamoyl chloride in the presence of a mixed base such as pyridine and triethylamine, pyridine and DIPEA, DMAP and triethylamine, or DMAP and DIPEA.

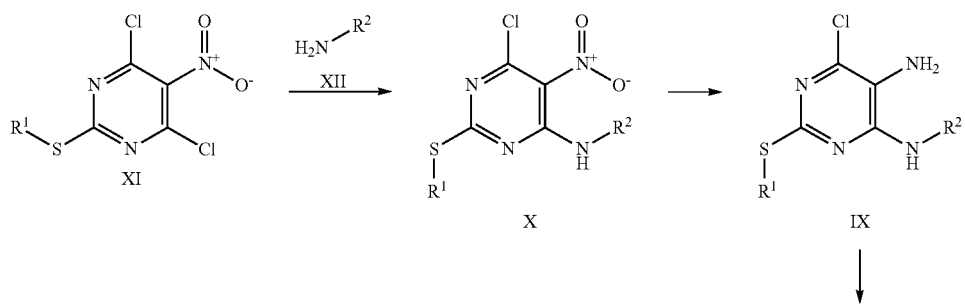

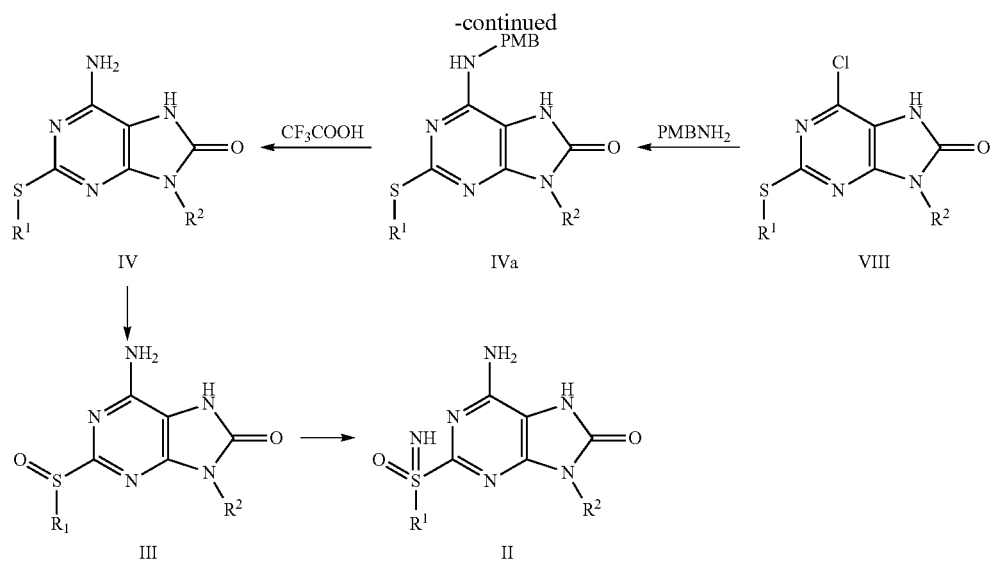

Compound of formula II can also be prepared as Scheme 2.

A compound of formula X is prepared by reaction of compound of formula XI with R²NH₂. Reduction of compound X with reducing reagent, such as Zinc or Iron powder in AcOH, gives the compound of formula IX. Cyclization of compound of formula IX with cyclization reagents, such as phosgene, carbonyl diimidazole, diethyl carbonate and triphosgene, affords compound of formula VIII A compound of formula IVa is prepared by treating the compound of formula VIII with PMBNH₂. A compound of formula III is prepared by deprotection of compound of formula IVa with acid, such as CF₃COOH, followed by oxidation with an oxidant, such as meta-chloroperoxybenzoic acid, urea-hydrogen peroxide adduct and HIO₄. Compound of formula II is obtained by the imination of compound of formula III with imination reagent, such as sodium azide in acid, said acid is for example Eaton's reagent or PPA.

This invention also relates to a process for the preparation of a compound of formula (I) comprising the reaction of:
the reaction of a compound of formula (II),

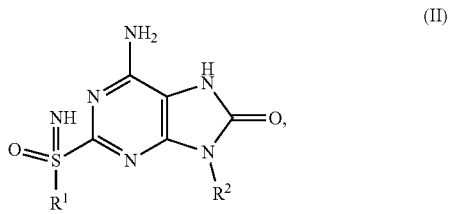

with carbamoyl chloride in the presence of a mixed base;
wherein R¹ and R² are defined above.

In above step, the mixed base can be, for example, pyridine and triethylamine, pyridine and DIPEA, DMAP and triethylamine, or DMAP and DIPEA.

A compound of formula (I) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) are formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to activate TLR7 receptor and lead to produce INF-α and other cytokines, which can be used, but not limited, for the treatment or prevention of hepatitis B and/or C viral infected patients.

In one example, the pharmaceutically effective amount of the compound of the invention administered parenterally per dose will be in the range of about 0.1 to 50 mg/kg, alternatively about 0.1 to 30 mg/kg of patient body weight per day, with the typical initial range of compound used being 0.3 to 15 mg/kg/day. In another embodiment, oral unit dosage forms, such as tablets and capsules, preferably contain from about 20 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 20 to 1000 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 20 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I) or pharmaceutically acceptable salts or enantiomers or diastereomers thereof.

In a further embodiment includes a pharmaceutical composition comprising a compound of formula (I) or pharmaceutically acceptable salts or enantiomers or diastereomers thereof, together with a pharmaceutically acceptable carrier or excipient.

Another embodiment includes a pharmaceutical composition comprising a compound of formula (I) or pharmaceutically acceptable salts or enantiomers or diastereomers thereof for use in the treatment of hepatitis B virus infection.

Indications and Methods of Treatment

The present invention provides methods for treating or preventing a hepatitis B viral infection and/or hepatitis C viral infection in a patient in need thereof.

The present invention further provides methods for introducing a therapeutically effective amount of a compound of formula (I) or other compounds of the invention into the blood stream of a patient for the treatment and/or prevention of hepatitis B and/or C viral infection.

The methods of the present invention are particularly well suited for human patients. In particular, the methods and doses of the present invention can be useful for, but not limited to, HBV and/or HCV infected patients. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Another embodiment includes a method of treating or preventing hepatitis B viral infection and/or hepatitis C viral infection in a mammal in need of such treatment, wherein the method comprises administering to said mammal a therapeutically effective amount of a compound of formula (I) or enantiomers, diastereomers, prodrugs or pharmaceutically acceptable salts thereof.

EXAMPLES

Figure 1:
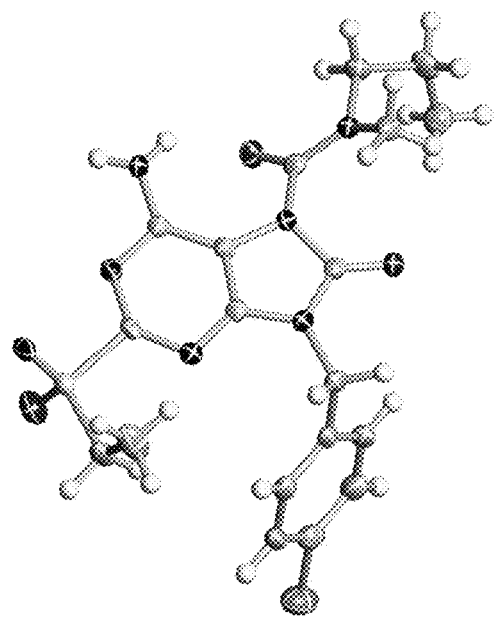
FIG. 1 Single crystal X-ray diffraction of Example 41-B.

The invention will be more fully understood by reference to the following examples. They should not, however, be construed as limiting the scope of the invention.

Abbreviations aq. aqueous
BSA: N,O-bis(trimethylsilyl)acetamide
CDI: N,N'-carbonyl diimidazole
DIEPA: N,N-diethylpropylamine DBU: 1,8-Diazabicycloundec-7-ene DPPA: diphenylphosphoryl azide $EC_{50}$: the molar concentration of an agonist, which produces 50% of the maximum possible response for that agonist.

EDC: N1-((ethylimino)methylene)-N3,N3-dimethyipropane-1,3-diamine

EtOAc or EA: ethyl acetate

HATU: (1-[Bis(dimethylamino)methylene]-1H-1,2,3-triazolo[4,5-b]pyridinium 3-oxid hexafluorophosphate)

hr(s): hour(s)

HPLC: high performance liquid chromatography

HOBt: N-hydroxybenzotriazole

MS (ESI): mass spectroscopy (electron spray ionization)

m-CPBA: 3-chloroperbenzoic acid

MTEB: methyl tert-butyl ether

NMP: N-methylpyrrolidone obsd. observed

PE: petroleum ether

PMB: p-methoxybenzyl

PPA: polyphosphoric acid

QOD every other day

QW once a week

RT or rt: room temperature sat. saturated

TFA: trifluoroacetic acid

TEA: triethylamine

V/V volume ratio

General Experimental Conditions

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 µm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 µm, OBD™ 30×100 mm) column or SunFire™ Perp $C_{18}$ (5 µm, OBD™ 30×100 mm) column.

LC/MS spectra were obtained using a Waters UPLC-SQD Mass. Standard LC/MS conditions were as follows (running time 3 minutes):

Acidic condition: A: 0.1% formic acid and 1% acetonitrile in $H_2O$; B: 0.1% formic acid in acetonitrile;

Basic condition: A: 0.05% $NH_3.H_2O$ in $H_2O$; B: acetonitrile.

Mass spectra (MS): generally only ions which indicate the parent mass are reported, and unless otherwise stated the mass ion quoted is the positive mass ion $(M+H)^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Preparation of Intermediate

Intermediate AA

N-methyl-N-propyl-carbamoyl chloride

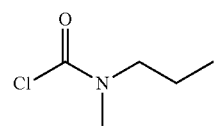

AA

To a mixture of N-methylpropan-1-amine (5 g, 68.4 mmol) and sodium hydrogencarbonate (11.5 g, 137 mmol) in DCM (70 mL) at 0° C. was added bis(trichloromethyl) carbonate (8.11 g, 27.3 mmol) in DCM (30 mL) dropwise. The mixture was stirred at room temperature for 2 hrs and filtered. The filtrate was concentrated in vacuo. The obtained N-methyl-N-propyl-carbamoyl chloride (7.2 g, Intermediate AA) was used for next step without further purification.

Intermediate AB

N-(2-Methoxyethyl)-N-methyl-carbamoyl chloride

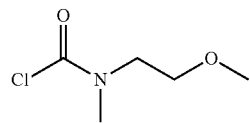

AB

Intermediate AB was prepared in analogy to Intermediate AA by using 2-methoxy-N-methyl-ethanamine instead of N-methylpropan-1-amine. N-(2-Methoxyethyl)-N-methylcarbamoyl chloride (8 g, Intermediate AB) was obtained and used for next step without further purification.

Intermediate AC

N-Ethyl-N-propyl-carbamoyl chloride

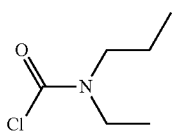

AC

Intermediate AC was prepared in analogy to Intermediate AA by using N-ethylpropan-1-amine instead of N-methylpropan-1-amine. N-Ethyl-N-propyl-carbamoyl chloride (12.6 g, Intermediate AC) was obtained as a yellow oil and used for next step without further purification.

Intermediate AD

N-Ethyl-N-(2-methoxyethyl)carbamoyl chloride

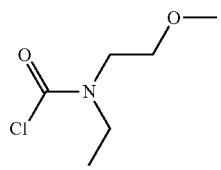

AD

Intermediate AD was prepared in analogy to Intermediate AA by using N-ethyl-2-methoxyethanamine instead of N-methylpropan-1-amine. The crude N-ethyl-N-(2-methoxyethyl)carbamoyl chloride (2.5 g, Intermediate AD) was obtained as a light yellow oil and used for next step without further purification.

Intermediate AE

N-Butyl-N-ethyl-carbamoyl chloride

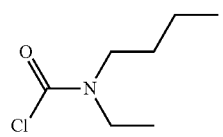

AE

Intermediate AE was prepared in analogy to Intermediate AA by using N-ethylbutan-1-amine (5 g) instead of N-methylpropan-1-amine. The crude N-butyl-N-ethyl-carbamoyl chloride (6.3 g, Intermediate AE) was obtained as a light yellow oil and used for next step without further purification.

Intermediate AF

N-(2-Methoxyethyl)-N-propyl-carbamoyl chloride

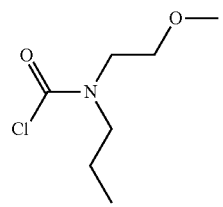

AF

Intermediate AF was prepared in analogy to Intermediate AA by using N-(2-methoxyethyl)propan-1-amine (2 g, 17.1 mmol) instead of N-methylpropan-1-amine. The crude N-(2-methoxyethyl)-N-propyl-carbamoyl chloride (2.5 g, Intermediate AF) was obtained as a light yellow oil and used for next step without further purification.

Intermediate AG

N,N-Bis(2-methoxyethyl)carbamoyl chloride

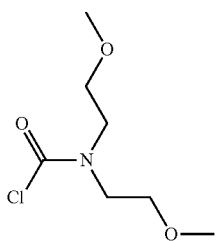

AG

Intermediate AG was prepared in analogy to Intermediate AA by using of bis(2-methoxyethyl)amine (2 g, 15 mmol) instead of N-methylpropan-1-amine. The crude product N,N-bis(2-methoxyethyl)carbamoyl chloride (2.6 g, Intermediate AG) was obtained as a light yellow oil and used for next step without further purification.

Intermediate AH

Azetidine-1-carbonyl chloride

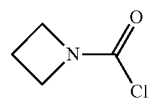

AH

Intermediate AH was prepared in analogy to Intermediate AA by using azetidine hydrochloride (10.7 g, 107 mmol) and sodium bicarbonate (3 equiv.) instead of N-methylpropan-1-amine and sodium bicarbonate (2 equiv.). The crude azetidine-1-carbonyl chloride (1.5 g, Intermediate AH) was obtained as a light yellow oil and used for next step without further purification.

Intermediate AI

N-Isopropyl-N-methyl-carbamoyl chloride

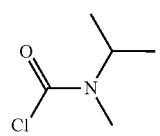

AI

Intermediate AI was prepared in analogy to Intermediate AA by using N-methylpropan-2-amine (5 g, 19.4 mmol) instead of N-methylpropan-1-amine. The crude N-isopropyl-N-methyl-carbamoyl chloride (8.6 g, Intermediate AI) was obtained as a yellow oil and used for next step without further purification.

Intermediate AL

N-Isobutyl-N-methyl-carbamoyl chloride

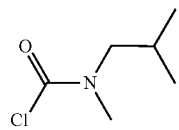

AL

Intermediate AL was prepared in analogy to Intermediate AA by using N-2-dimethylpropan-1-amine (4.8 g) instead of N-methylpropan-1-amine. The crude N-isobutyl-N-methyl-carbamoyl chloride (8.1 g, Intermediate AL) was obtained as a light yellow oil and used for next step without further purification.

Intermediate AP

Ethyl 2-[chlorocarboyl(methyl)amino]acetate

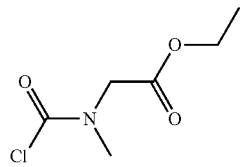

AP

To a solution of triphosgene (728 mg, 2.45 mmol) in DCM (5 mL) was added a solution of ethyl 2-(methylamino)acetate hydrochloride (1.3 g, 8.46 mmol) and pyridine (1 mL) in DCM (5 mL) dropwise at 0° C. The reaction mixture became orange and a yellow precipitate appeared, then it was allowed to warm to room temperature. After stirred for 1 hr, aqueous HCl (0.1N, 25 mL) was added to the reaction mixture, the organic layer was separated, washed with 0.1N HCl (10 mL) twice, brine (10 mL), dried over $Na_2SO_4$ and concentrated in vacuo to give the crude ethyl 2-[chlorocarbonyl(methyl)amino]acetate (2.0 g, Intermediate AP) as a light yellow oil and used for next step without further purification.

Intermediate AR tert-Butyl 3-[chlorocarboyl(methyl)amino]propanoate

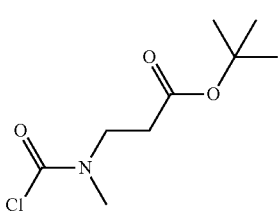

AR

Step 1: Preparation of tert-butyl 3-(methylamino)propanoate (Compound AR-1)

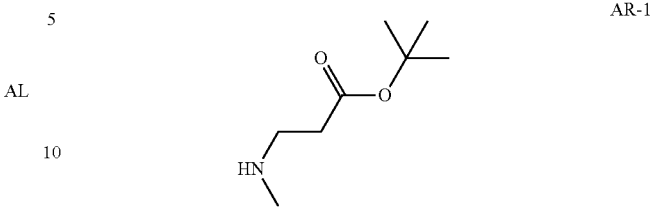

AR-1

To a solution of tert-butyl acrylate (3 g) in DMF (40 mL) was added methylamine hydrochloride (4.74 g, 70 mmol) and DBU (21.4 g, 140 mmol) at −45° C. Then the reaction temperature was allowed to warm to −10° C. The reaction mixture was stirred at the same temperature for 2.5 hrs. $Et_2O$ (200 mL) was added and the resulting mixture was washed with brine (50 mL) four times. The separated organic layer was dried over $Na_2SO_4$ and concentrated in vacuo to afford tert-butyl 3-(methylamino)propanoate (3.5 g, Compound AR-1) as a light yellow oil.

Step 2: Preparation of tert-butyl 3-[chlorocarbonyl(methyl)amino]propanoate (Intermediate AR)

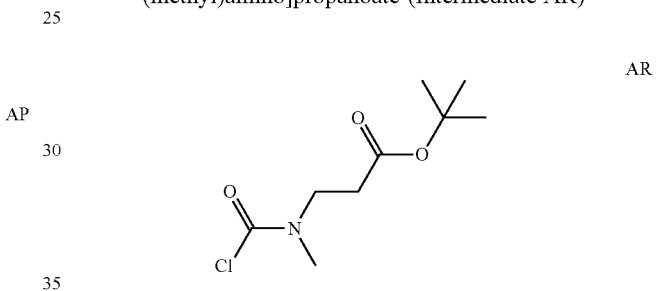

AR

Intermediate AR was prepared in analogy to Intermediate AP by using tert-butyl 3-(methylamino)propanoate (3.4 g, Compound AR-1) instead of ethyl 2-(methylamino)acetate hydrochloride. The crude tert-butyl 3-[chlorocarbonyl (methyl)amino]propanoate (3.5 g, Intermediate AR) was obtained and used for next step without further purification.

Intermediate AS

Ethyl(2S)-2-[chlorocarbonyl(methyl)amino]propanoate

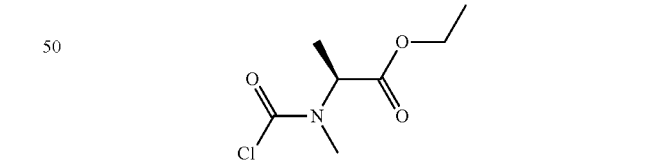

AS

Step 1: Preparation of ethyl(2S)-2-(methylamino)propanoate hydrochloride (Compound AS-1)

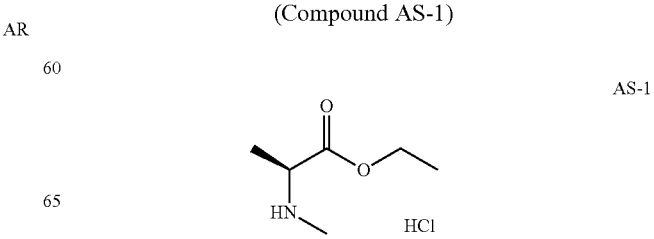

AS-1

To a solution of (2S)-2-(methylamino)propanoic acid (1 g, 9.70 mmol) in EtOH (10 mL) was added SOCl$_2$ (1.50 g, 12.61 mmol) dropwise at 0° C. in 0.5 hr. The reaction mixture was stirred at 25° C. for 15.5 hrs, then diluted with EA (20 mL), washed with H$_2$O (5 mL) and brine (5 mL). The organic layer was dried over Na$_2$SO$_4$ and concentrated in vacuo. Ethyl (2S)-2-(methylamino)propanoate hydrochloride (1.8 g, Compound AS-1) was obtained as a yellow oil and used for next step without further purification.

Step 2: Preparation of ethyl(2S)-2-(methylamino)propanoate (Compound AS-2)

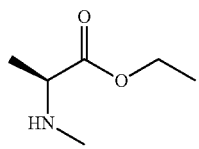

AS-2

A solution of ethyl (2S)-2-(methylamino)propanoate hydrochloride (1.8 g, Compound AS-1) in EA (10 mL) was adjusted to pH=8 with 10 wt. % aqueous NaHCO$_3$. The reaction mixture was stirred at room temperature for 0.5 hr. The organic layer was washed with brine (5 mL), dried over Na$_2$SO$_4$ and concentrated in vacuo. Ethyl (2S)-2-(methylamino)propanoate (620 mg, Compound AS-2) was obtained as a yellow oil and used for the next step without further purification.

Step 3: Preparation of ethyl(2S)-2-[chlorocarbonyl(methyl)amino]propanoate (Intermediate AS)

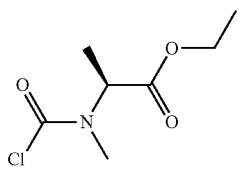

AS

Intermediate AS was prepared in analogy to Intermediate AP by using ethyl (2S)-2-(methylamino)propanoate (260 mg, Compound AS-2) instead of ethyl 2-(methylamino)acetate hydrochloride. The crude ethyl (2S)-2-[chlorocarbonyl(methyl)amino]propanoate (200 mg, Intermediate AS) was obtained as a yellow oil and used for the next step without further purification.

Intermediate AT tert-Butyl(2S)-2-[chlorocarbonyl(methyl)amino]-4-methyl-pentanoate

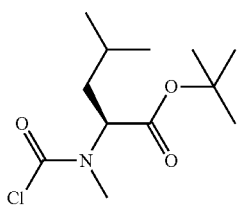

AT

Step 1: Preparation of tert-butyl(2S)-4-methyl-2-(methylamino)pentanoate (Compound AT-1)

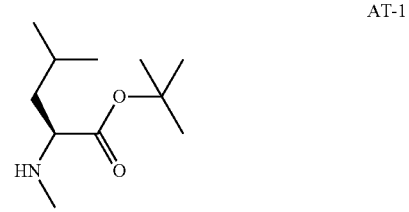

AT-1

2-Methylpropene (25 g, 446 mmol) was bubbled into DCM (50 mL) at −78° C. Then the 2-methylpropene solution was added to a solution of (S)-4-methyl-2-(methylamino)pentanoic acid hydrochloride (500 mg, 2.75 mmol) and H$_2$SO$_4$ (3.68 g, 2 mL, 37.5 mmol) in dioxane (20 mL) at 0° C. The reaction mixture was stirred at room temperature for 18 hrs in a sealed tube. The reaction solution was poured into an ice cold aqueous KOH solution (8.4 g in water (30 mL)) and the resulting mixture was extracted with DCM (50 mL) twice. The combined organic layer was washed with brine (30 mL) twice, dried over Na$_2$SO$_4$ and concentrated in vacuo to afford the crude product tert-butyl (2S)-4-methyl-2-(methylamino)pentanoate (Compound AT-1) as a light yellow oil.

Step 2: Preparation of tert-butyl(2S)-2-[chlorocarboyl(methyl)amino]-4-methyl-pentanoate (Intermediate AT)

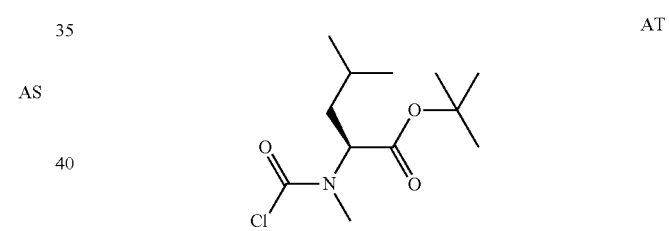

AT

Intermediate AT was prepared in analogy to Intermediate AP by using tert-butyl (2S)-4-methyl-2-(methylamino)pentanoate (300 mg, Compound AT-1) instead of ethyl 2-(methylamino)acetate hydrochloride. The crude tert-butyl (2S)-2-[chlorocarbonyl(methyl)amino]-4-methyl-pentanoate (350 mg, Intermediate AT) was obtained as a light yellow oil and used for the next step without further purification.

Intermediate AU

Isopropyl(2S)-2-[chlorocarboyl(methyl)amino]-4-methyl-pentanoate

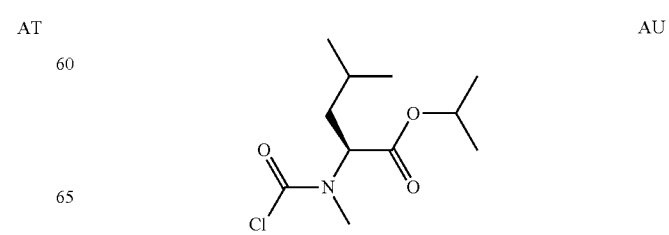

AU

Step 1: Preparation of isopropyl(2S)-4-methyl-2-(methylamino)pentanoate hydrochloride (Compound AU-1)

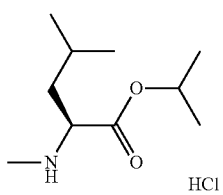

AU-1

To a solution of (S)-4-methyl-2-(methylamino)pentanoic acid hydrochloride (0.5 g) in i-PrOH (7.8 g, 10 mL) was added thionyl chloride (655 mg, 402 µL) dropwise at room temperature. The resulting mixture was stirred and refluxed for 16 hrs and then concentrated in vacuo. The residue was basified with saturated aqueous NaHCO₃ (30 mL) and extracted with DCM (50 mL). The organic layer was washed with brine, dried over Na₂SO₄ and concentrated in vacuo. The residue was salified with HCl/EtOAc (10 mL, 1 mmol/mL) and concentrated to afford isopropyl (2S)-4-methyl-2-(methyl amino)pentanoate hydrochloride (510 mg, Compound AU-I) as a white solid.

Step 2: Preparation of isopropyl(2S)-2-[chlorocarboyl(methyl)amino]-4-methyl-pentanoate (Intermediate AU)

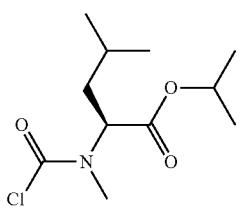

AU

Intermediate AU was prepared in analogy to Intermediate AP by using isopropyl (2S)-4-methyl-2-(methylamino)pentanoate hydrochloride (500 mg, Compound AU-I) instead of ethyl 2-(methylamino)acetate hydrochloride. The crude isopropyl (2S)-2-[chlorocarbonyl(methyl)amino]-4-methyl-pentanoate (650 mg, Intermediate AU) was obtained as a light yellow oil and used for the next step without further purification.

Intermediate AV

Ethyl(2S)-2-[chlorocarboyl(methyl)amino]-3-methyl-butanoate

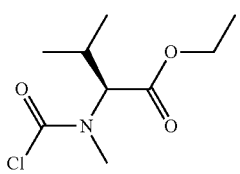

AV

Step 1: Preparation of ethyl(2S)-3-methyl-2-(methylamino)butanoate hydrochloride (Compound AV-1)

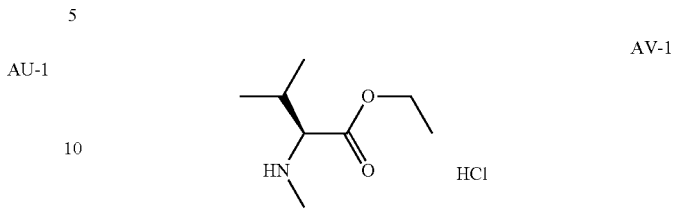

AV-1

To a solution of (2S)-3-methyl-2-(methylamino)butanoic acid (1.0 g, 7.6 mmol) in EtOH (10 mL) was added thionyl chloride (2.45 g, 21 mmol) dropwise at room temperature. The resulting mixture was stirred and refluxed for 16 hrs and then concentrated in vacuo. The residue was basified with saturated aqueous NaHCO₃ (30 mL) and extracted with DCM (50 mL) twice. The combined organic layer was washed with brine, dried over Na₂SO₄ and concentrated in vacuo. The residue was dissolved in HCl/EtOAc (10 mL, 1M) and concentrated to afford ethyl (2S)-3-methyl-2-(methylamino)butanoate hydrochloride (1.9 g, Compound AV-1) as a white solid.

Step 2: Preparation of ethyl(2S)-2-[chlorocarbonyl(methyl)amino]-3-methyl-butanoate (Intermediate AV)

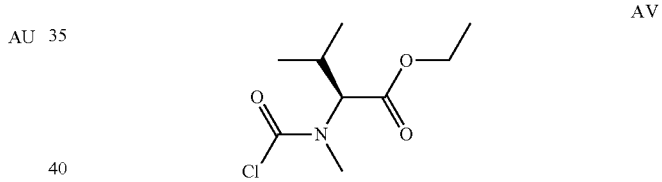

AV

Intermediate AV was prepared in analogy to Intermediate AP by using ethyl (2S)-3-methyl-2-(methylamino)butanoate hydrochloride (500 mg, Compound AV-1) instead of ethyl 2-(methylamino)acetate hydrochloride. The crude ethyl (2S)-2-[chlorocarbonyl(methyl)amino]-3-methyl-butanoate (600 mg, Intermediate AV) was obtained as a light yellow oil and used for the next step without further purification.

Intermediate AW

Ethyl(2S)-2-[chlorocarbonyl(methyl)amino]-4-methyl-pentanoate

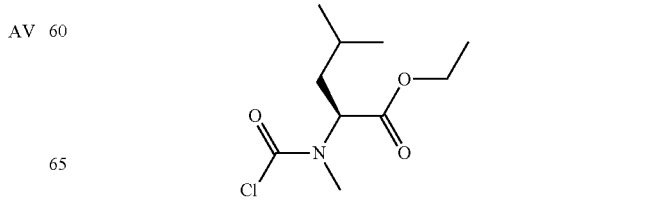

AW

Step 1: Preparation of ethyl(2S)-4-methyl-2-(methylamino)pentanoate hydrochloride (Compound AW-1)

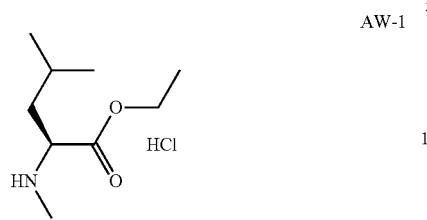

To a solution of (2S)-4-methyl-2-(methylamino)pentanoic acid (1 g, 6.9 mmol) in EtOH (10 mL) was added thionyl chloride (1.07 g, 8.3 mmol) dropwise at room temperature. The resulting mixture was stirred at reflux for 16 hrs and then concentrated in vacuo. The residue was basified with saturated aqueous NaHCO$_3$ (30 mL) and extracted with DCM (50 mL). The organic layer was washed with brine, dried over Na$_2$SO$_4$ and concentrated in vacuo. The residue was salified with HCl/EtOAc (10 mL, 1 mmol/mL) and concentrated to give ethyl (2S)-4-methyl-2-(methylamino) pentanoate hydrochloride (1.8 g, Compound AW-1) as a white solid.

Step 2: Preparation of ethyl(2S)-2-[chlorocarboyl (methyl)amino]-4-methyl-pentanoate (Intermediate AW)

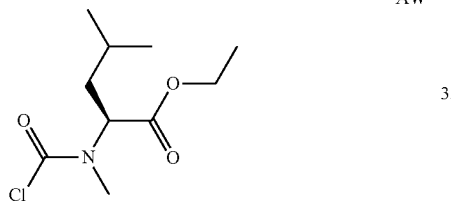

Intermediate AW was prepared in analogy to Intermediate AP by using ethyl (2S)-4-methyl-2-(methylamino)pentanoate hydrochloride (610 mg, AW-1) instead of ethyl 2-(methylamino)acetate hydrochloride. The crude ethyl (2S)-2-[chlorocarbonyl(methyl)amino]-4-methyl-pentanoate (280 mg, Intermediate AW) was obtained as a light yellow oil and used for the next step without further purification.

Intermediate AX

Ethyl(2S)-2-[chlorocarboyl(methyl)amino]-3-phenyl-propanoate

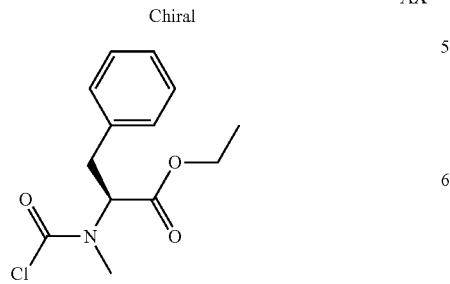

Intermediate AX was prepared in analogy to Intermediate AP by using (S)-ethyl-2-(methylamino)-3-phenylpropanoate instead of ethyl 2-(methylamino)acetate hydrochloride. The crude ethyl (2S)-2-[chlorocarbonyl(methyl)amino]-3-phenyl-propanoate (200 mg, Intermediate AX) was obtained as a light yellow oil and used for the next step without further purification Intermediate AY Isopropyl(2S)-2-[chlorocarbonyl(methyl)amino]-3-phenyl-propanoate

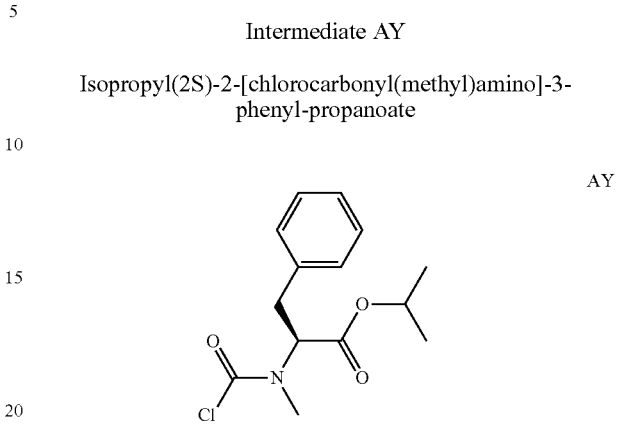

Intermediate AY was prepared in analogy to Intermediate AP by using isopropyl (2S)-2-(methylamino)-3-phenyl-propanoate (190 mg) instead of ethyl 2-(methylamino)acetate hydrochloride. The crude isopropyl (2S)-2-[chlorocarbonyl (methyl)amino]-3-phenyl-propanoate (220 mg, Intermediate AY) was obtained as light brown oil and used for the next step without further purification.

Intermediate AZ (S)-tert-butyl 2-((chlorocarbonyl)(methyl)amino)-3-phenylpropanoate

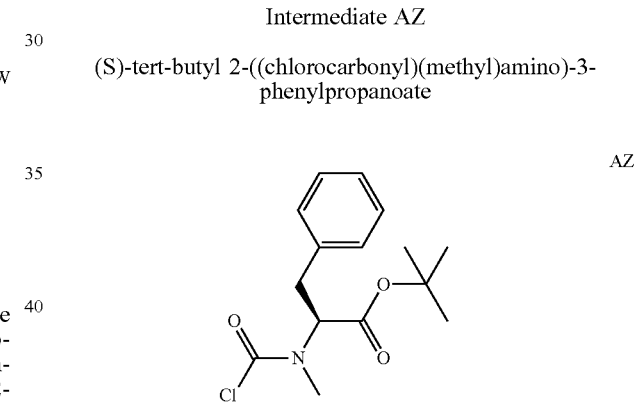

Step 1: Preparation of tert-butyl(2S)-2-(methylamino)-3-phenyl-propanoate (Compound AZ-1)

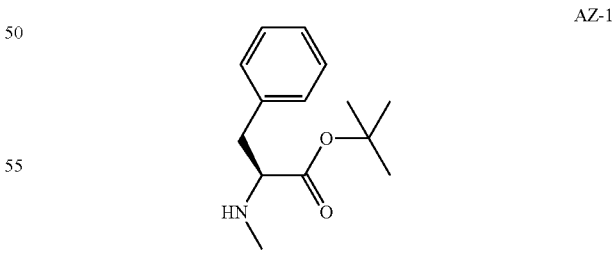

2-Methylpropene (25 g, 446 mmol) was bubbled into DCM (50 mL) at −78° C. Then the 2-methylpropene solution was added to a solution of (S)-2-(methylamino)-3-phenylpropanoic acid (500 mg) and H$_2$SO$_4$ (3.68 g, 2 mL) in dioxane (20 mL) at 0° C. The reaction mixture was stirred at room temperature for 18 hrs in a sealed tube. The reaction mixture was poured into an ice cold aqueous KOH solution (8.4 g in water (30 mL)) and the resulting mixture was extracted with DCM (50 mL) twice. The organic layer was washed with brine (30 mL) 2 times, dried over Na$_2$SO$_4$ and concentrated in vacuo to afford tert-butyl (2S)-2-(methyl-amino)-3-phenyl-propanoate (710 mg, Compound AZ-1) as a light yellow oil.

Step 2: Preparation of (S)-tert-butyl 2-((chlorocar-bonyl)(methyl)amino)-3-phenylpropanoate (Intermediate AZ)

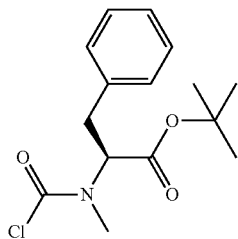

Intermediate AZ was prepared in analogy to intermediate AP by using tert-butyl (2S)-2-(methylamino)-3-phenyl-propanoate (Compound AZ-1) instead of ethyl 2-(methylamino) acetate hydrochloride. The crude tert-butyl (2S)-2-[chloro-carbonyl(methyl)amino]-3-phenyl-propanoate (360 mg, Intermediate AZ) was obtained as a light yellow oil and used for next step without further purification Intermediate BA N-[2-[acetyl(methyl)amino]ethyl]-N-methyl-carbam-oyl chloride

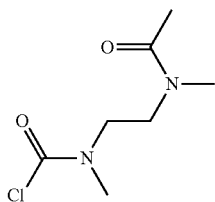

Step 1: Preparation of tert-butyl N-[2-[acetyl(methyl)amino]ethyl]-N-methyl-carbamate (Compound BA-1)

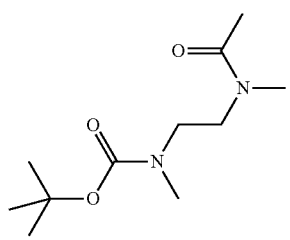

To a solution of tert-butyl methyl(2-(methylamino)ethyl) carbamate (1.13 g, 6 mmol) in pyridine (10 mL) was added acetic anhydride (3.06 g, 30 mmol) dropwise at 0° C. Then the solution was stirred at room temperature for 0.5 hr. The solvent was removed in vacuo and the residue was partitioned between EtOAc (50 mL) and saturated aqueous NaHCO$_3$ (25 mL). The organic layer was separated, washed with brine (20 mL), dried over Na$_2$SO$_4$ and concentrated in vacuo to afford tert-butyl N-[2-[acetyl(methyl)amino]ethyl]-N-methyl-carbamate (1.28 g, Compound BA-1) as a yellow oil.

Step 2: Preparation of N-methyl-N-(2-(methyl-amino)ethyl)acetamide hydrochloride (Compound BA-2)

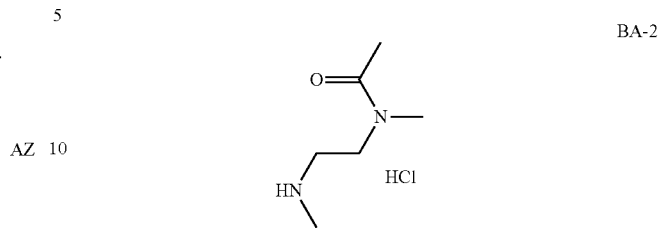

A mixture of tert-butyl N-[2-[acetyl(methyl)amino] ethyl]-N-methyl-carbamate (1.1 g, Compound BA-1) in HCl/EtOAc (10 mL, 1N HCl in EtOAc) was stirred at room temperature for 2 hrs, then the mixture was filtered. The collected solid was washed with EtOAc (5 mL) three times and dried in vacuo to afford the crude N-methyl-N-(2-(methylamino)ethyl)acetamide hydrochloride (460 mg, Compound BA-2) as a white solid.

Step 3: Preparation of N-[2-[acetyl(methyl)amino] ethyl]-N-methyl-carbamoyl chloride (Intermediate BA)

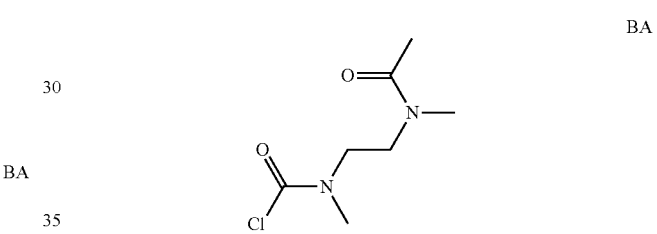

Intermediate BA was prepared in analogy to Intermediate AP by using N-methyl-N-(2-(methylamino)ethyl)acetamide hydrochloride (200 mg, Compound BA-2) instead of ethyl 2-(methylamino)acetate hydrochloride The crude N-[2-[acetyl(methyl)amino]ethyl]-N-methyl-carbamoyl chloride (300 mg, Intermediate BA) was obtained and used for next step without further purification.

Intermediate BB

Methyl N-[2-[chlorocarbonyl(methyl)amino]ethyl]-N-methyl-carbamate

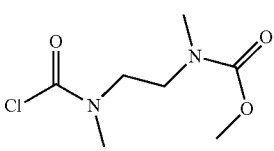

Step 1: Preparation of methyl N-methyl-N-[2-(methylamino)ethyl]carbamate (Compound BB-1)

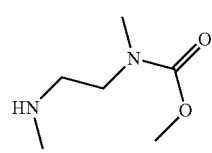

To a solution of N,N'-dimethylethane-1,2-diamine (10 g) in THF (40 mL) was added methyl chloroformate (1.92 g) dropwise at −70° C. in 1 hr. The mixture was stirred at 25° C. for 15 hrs and then filtered and washed with water and brine. The organic layer was dried and concentrated to afford a yellow residue, which was purified by column chromatography to afford methyl N-methyl-N-[2-(methylamino)ethyl]carbamate (2 g, Compound BB-1) as a colorless oil.

Step 2: Preparation of methyl N-[2-[chlorocarbonyl(methyl)amino]ethyl]-N-methyl-carbamate (Intermediate BB)

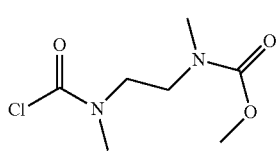

BB

Intermediate BB was prepared in analogy to Intermediate AP by using methyl N-methyl-N-[2-(methylamino)ethyl]carbamate (2.0 g, Compound BB-1) instead of ethyl 2-(methylamino)acetate hydrochloride. The crude methyl N-[2-[chlorocarbonyl(methyl)amino]ethyl]-N-methyl-carbamate (2.2 g, Intermediate BB) was obtained and used for next step without further purification.

Intermediate BC tert-Butyl N-[2-[chlorocarbonyl(methyl)amino]ethyl]-N-methyl-carbamate

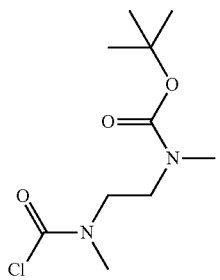

BC

Step 1: Preparation of tert-butyl N-methyl-N-[2-(methylamino)ethyl]carbamate (Compound BC-1)

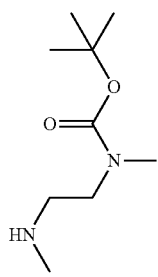

BC-1

To a solution of N,N'-dimethylethane-1,2-diamine (40.4 g) in DCM (300 mL) was added a solution of Boc$_2$O (10 g, 10.6 mL, 45.8 mmol) in DCM (100 mL) dropwise at 0° C. over 1 hr. The reaction mixture was stirred at room temperature for 18 hrs. The organic layer was washed with saturated aqueous NaHCO$_3$ (50 mL), brine (50 mL), dried over Na$_2$SO$_4$ and concentrated in vacuo. The residue was purified by column chromatography to afford tert-butyl N-methyl-N-[2-(methylamino)ethyl]carbamate (6.8 g, Compound BC-1) as a yellow oil. $^1$H NMR (400 MHz, CDCl$_3$) δ ppm: 3.34 (br. s., 2H), 2.89 (s, 3H), 2.74 (t, J=6.7 Hz, 2H), 2.46 (s, 3H), 1.47 (s, 9H).

Step 2: Preparation of tert-butyl N-[2-[chlorocarbonyl(methyl)amino]ethyl]-N-methyl-carbamate (Intermediate BC)

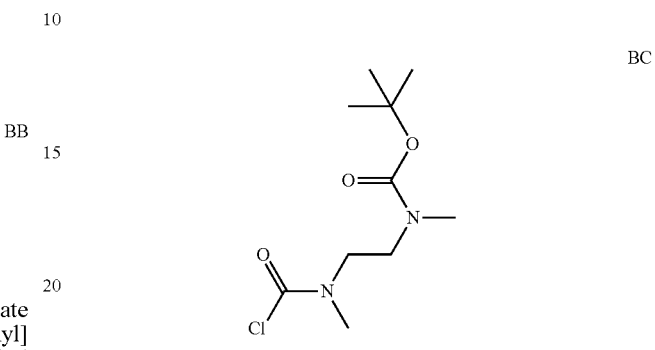

Intermediate BC was prepared in analogy to Intermediate AP by using tert-butyl N-methyl-N-[2-(methylamino)ethyl]carbamate (1.15 g, Compound BC-1) instead of ethyl 2-(methylamino)acetate hydrochloride. The crude tert-butyl N-[2-[chlorocarbonyl(methyl)amino]ethyl]-N-methyl-carbamate (1.3 g, Intermediate BC) was obtained and used for the next step without further purification.

Intermediate BD

Ethyl N-[2-[chlorocarboyl(methyl)amino]ethyl]-N-methyl-carbamate

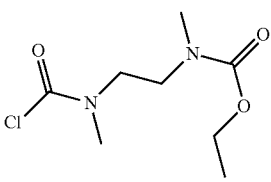

BD

Step 1: Preparation of ethyl N-methyl-N-[2-(methylamino)ethyl]carbamate (Compound BD-1)

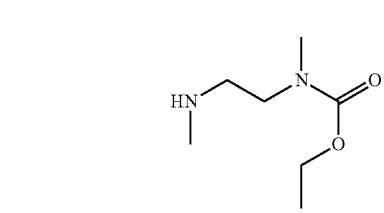

BD-1

To a solution of N,N'-dimethylethane-1,2-diamine (10 g) in DCM (40 mL) was added ethyl chloroformate (2.58 g) dropwise at −70° C. in 1 hr. The reaction mixture was stirred at 25° C. for 15 hrs and then filtered and washed with water and brine. The organic layer was dried and concentrated in vacuo. The yellow residue was purified by column chromatography to afford ethyl N-methyl-N-[2-(methylamino) ethyl]carbamate (2 g, Compound BD-1) as a colorless oil.

Step 2: Preparation of ethyl N-[2-[chlorocarboyl (methyl)amino]ethyl]-N-methyl-carbamate (Intermediate BD)

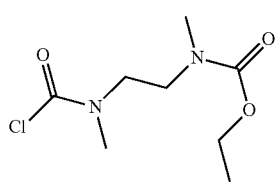

BD

Intermediate BD was prepared in analogy to Intermediate AA by using ethyl N-methyl-N-[2-(methylamino)ethyl]carbamate (Compound BD-1) instead of ethyl 2-(methylamino) acetate hydrochloride. The crude ethyl N-[2-[chlorocarbonyl (methyl)amino]ethyl]-N-methyl-carbamate (2.2 g, Intermediate BD) was obtained and used for the next step without further purification.

Intermediate BE

2-[Chlorocarboyl(methyl)amino]ethyl N-butyl-N-methyl-carbamate

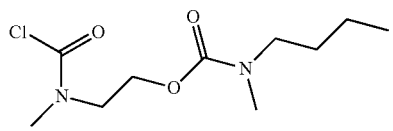

BE

Step 1: Preparation of tert-butyl N-(2-hydroxyethyl)-N-methyl-carbamate (Compound BE-1)

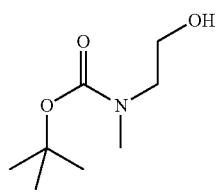

BE-1

To a solution of 2-(methylamino)ethanol (10 g, 133.14 mmol) in DCM (10 mL) was added Boc$_2$O (34.87 g, 159.77 mmol) at 25° C. The mixture was stirred at 25° C. for 16 hrs and then concentrated. The residue was purified by column chromatography to afford tert-butyl N-(2-hydroxyethyl)-N-methyl-carbamate (20 g, Compound BE-1) as a colorless oil.

Step 2: Preparation of 2-[tert-butoxycarbonyl (methyl)amino]ethyl N-butyl-N-methyl-carbamate (Compound BE-2)

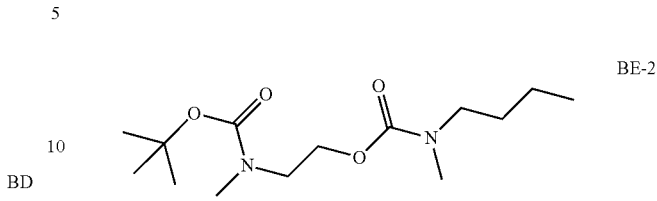

BE-2

To a solution of tert-butyl N-(2-hydroxyethyl)-N-methyl-carbamate (880 mg, Compound BE-1) and Et$_3$N (1 g, 10.08 mmol) in DCM (10 mL) was added N-butyl-N-methyl-carbamoyl chloride (903 mg, 7.04 mmol) dropwise at −10° C. in 1 hr. The reaction mixture was stirred at 25° C. for 15 hrs and then filtered and washed with water and brine. The organic layer was dried and concentrated to afford 2-[tert-butoxycarbonyl(methyl)amino]ethyl N-butyl-N-methyl-carbamate (2 g, Compound BE-2) as a colorless oil.

Step 3: Preparation of 2-(methylamino)ethyl N-butyl-N-methyl-carbamate hydrochloride (Compound BE-3)

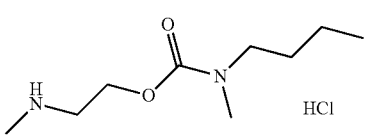

BE-3

To a solution of 2-[tert-butoxycarbonyl(methyl)amino] ethyl N-butyl-N-methyl-carbamate (1 g, Compound BE-2) was added HCl/EA (40 mL, 1M). The reaction mixture was stirred at 0° C. for 0.5 hr and warmed to 25° C. and stirred for another 15.5 hrs. The reaction mixture was concentrated to afford 2-(methylamino)ethyl-N-butyl-N-methyl-carbamate hydrochloride (400 mg, Compound BE-3) as a colorless oil.

Step 4: Preparation of 2-[chlorocarbonyl(methyl) amino]ethyl N-butyl-N-methyl-carbamate (Intermediate BE)

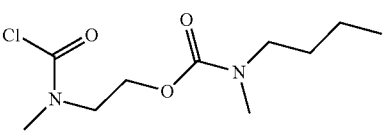

BE

Intermediate BE was prepared in analogy to Intermediate AP by using 2-(methylamino)ethyl N-butyl-N-methyl-carbamate hydrochloride (374 mg, Compound BE-3) instead of ethyl 2-(methylamino)acetate hydrochloride. The crude 2-[chlorocarbonyl(methyl)amino]ethyl N-butyl-N-methyl-carbamate (330 mg, Intermediate BE) was obtained and used for next step without further purification.

Intermediate BF

2-[Chlorocarbonyl(methyl)amino]ethyl pyrrolidine-1-carboxylate

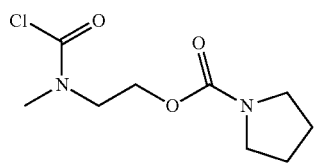
BF

Step 1: Preparation of tert-butyl N-(2-hydroxyethyl)-N-methyl-carbamate (Compound BF-1)

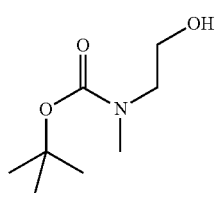
BF-1

To a solution of 2-(methylamino)ethanol (10 g, 133.14 mmol) in DCM (10 mL) was added Boc₂O (34.87 g, 159.77 mmol) at 25° C. The mixture was stirred at 25° C. for 16 hrs. The reaction mixture was concentrated to give the residue, which was purified by column chromatography to afford tert-butyl N-(2-hydroxyethyl)-N-methyl-carbamate (20 g, Compound BF-1) as a colorless oil.

Step 2: Preparation of 2-[tert-butoxycarbonyl(methyl)amino]ethyl pyrrolidine-1-carboxylate (Compound BF-2)

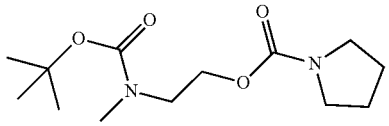
BF-2

To a solution of tert-butyl N-(2-hydroxyethyl)-N-methyl-carbamate (300 mg, 1.71 mmol, Compound BF-1) and Et₃N (578 mg, 5.71 mmol) in DCM (5 mL) was added pyrrolidine-1-carbonyl chloride (458 mg, 3.4 mmol) dropwise at 0° C. for 0.5 hr and then stirred at 25° C. for 15.5 hrs. After filtration, the filtrate was washed with water and brine. The organic layer was dried and concentrated to afford the 2-[tert-butoxycarbonyl(methyl)amino]ethyl pyrrolidine-1-carboxylate (335 mg, Compound BF-2) as a colorless oil.

Step 3: Preparation of 2-(methylamino)ethyl pyrrolidine-1-carboxylate hydrochloride (Compound BF-3)

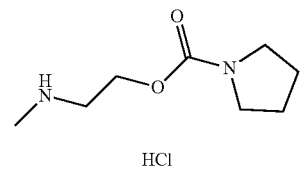
BF-3

HCl

2-[tert-butoxycarbonyl(methyl)amino]ethyl pyrrolidine-1-carboxylate (335 mg, Compound BF-2) was added to HCl in EA (12.3 mL, 1M) and the mixture was stirred at 0° C. for 0.5 hr and then at 25° C. for another 15.5 hrs. The reaction mixture was concentrated to afford 2-(methylamino)ethyl pyrrolidine-1-carboxylate hydrochloride (300 mg, Compound BF-3) as a colorless oil.

Step 4: Preparation of 2-[chlorocarbonyl(methyl)amino]ethyl pyrrolidine-1-carboxylate (Intermediate BF)

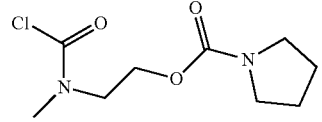
BF

Intermediate BF was prepared in analogy to Intermediate AP by using the 2-(methylamino)ethyl pyrrolidine-1-carboxylate hydrochloride (299 mg, Compound BF-3) instead of ethyl 2-(methylamino)acetate hydrochloride. The crude 2-[chlorocarbonyl(methyl)amino]ethyl pyrrolidine-1-carboxylate (230 mg, Intermediate BF) was obtained and used for next step without further purification.

Intermediate BG

2-[Chlorocarbonyl(methyl)amino]ethyl N-methyl-N-propyl-carbamate

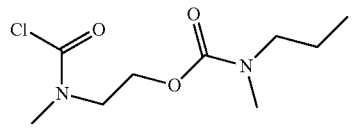
BG

Step 1: Preparation of tert-butyl N-(2-hydroxyethyl)-N-methyl-carbamate (Compound BG-1)

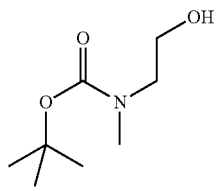
BG-1

To a solution of 2-(methylamino)ethanol (10 g, 133.14 mmol) in DCM (10 mL) was added Boc₂O (34.87 g, 159.77 mmol) at 25° C. The reaction mixture was stirred at 25° C. for 16 hrs, then concentrated to give the residue, which was purified by column chromatography to afford tert-butyl N-(2-hydroxyethyl)-N-methyl-carbamate (20 g, Compound BG-1) as a colorless oil.

Step 2: Preparation of tert-butyl-N-methyl-N-[2-[methyl(propyl)carbamoyl]oxyethyl]carbamate (Compound BG-2)

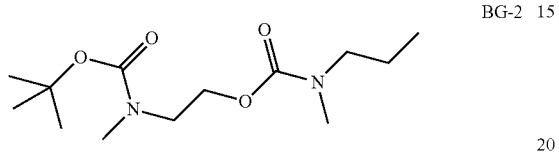

BG-2

To a solution of tert-butyl N-(2-hydroxyethyl)-N-methyl-carbamate (265 mg, Compound BG-1) and Et₃N (1 mL, 5.71 mmol) in DCM (5 mL) was added N-methyl-N-propyl-carbamoyl chloride (410 mg, 1.83 mmol) dropwise at 0° C. for 0.5 hr. The reaction mixture was stirred at 25° C. for 15.5 hrs and then filtered and the filtrate was washed with water and brine. The organic layer was dried and concentrated to afford tert-butyl N-methyl-N-[2-[methyl(propyl)carbamoyl]oxyethyl]carbamate (380 mg, Compound BG-2) as a colorless oil.

Step 3: Preparation of 2-(methylamino)ethyl N-methyl-N-propyl-carbamate hydrochloride (Compound BG-3)

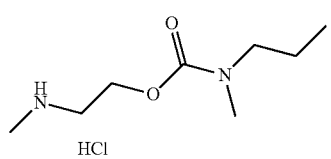

BG-3 tert-butyl N-methyl-N-[2-[methyl(propyl)carbamoyl]oxyethyl]carbamate (380 mg, Compound BG-2) was added to HCl in EA (13.7 mL, 1M). The mixture was stirred at 0° C. for 0.5 hr. Then the mixture was stirred at 25° C. for another 15.5 hrs and concentrated to afford 2-(methylamino)ethyl N-methyl-N-propyl-carbamate hydrochloride (300 mg, Compound BG-3) as a colorless oil.

Step 4: Preparation of 2-[chlorocarbonyl(methyl)amino]ethyl N-methyl-N-propyl-carbamate (Intermediate BG)

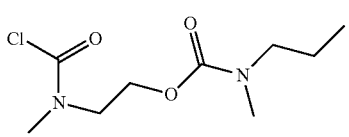

BG

Intermediate BG was prepared in analogy to Intermediate AP by using 2-(methylamino)ethyl N-methyl-N-propyl-carbamate hydrochloride (330 mg, Compound BG-3) instead of ethyl 2-(methylamino)acetate hydrochloride. The 2-[chlorocarbonyl(methyl)amino]ethyl-N-methyl-N-propyl-carbamate (300 mg, Intermediate BG) was obtained and used for next step without further purification.

Intermediate BH

2-[Chlorocarboyl(methyl)amino]ethyl N,N-diethylcarbamate

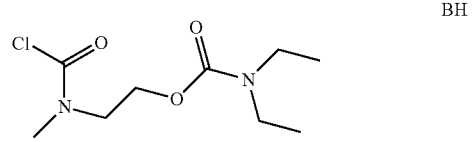

BH

Step 1: Preparation of tert-butyl N-(2-hydroxyethyl)-N-methyl-carbamate (Compound BH-1)

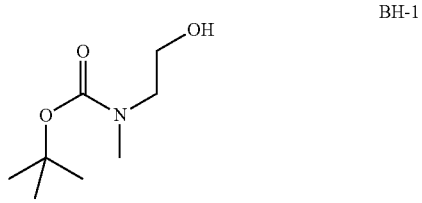

BH-1

To a solution of 2-(methylamino)ethanol (10 g, 133.14 mmol) in DCM (10 mL) was added Boc₂O (34.87 g, 159.77 mmol) at 25° C. The mixture was stirred at 25° C. for 16 hrs and then concentrated, the residue was purified by column chromatography to afford tert-butyl N-(2-hydroxyethyl)-N-methyl-carbamate (20 g, Compound BH-1) as a colorless oil.

Step 2: Preparation of 2-[tert-butoxycarbonyl(methyl)amino]ethyl-N,N-diethylcarbamate (Compound BH-2)

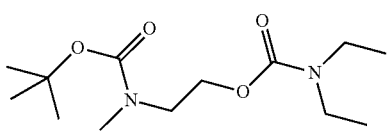

BH-2

To a solution of tert-butyl N-(2-hydroxyethyl)-N-methyl-carbamate (200 mg, 1.14 mmol, Compound BH-1) and Et₃N (578 mg, 5.71 mmol) in DCM (5 mL) was added N,N-diethylcarbamoyl chloride (248 mg, 1.83 mmol) dropwise at 0° C. for 0.5 hr and stirred at 25° C. for 15.5 hrs. After filtration, the filtrate was washed with water and brine. The organic layer was dried and concentrated to afford the 2-[tert-butoxycarbonyl(methyl)amino]ethyl N,N-diethylcarbamate (313 mg, Compound BH-2) as a colorless oil.

Step 3: Preparation of 2-(methylamino)ethyl N,N-diethylcarbamate hydrochloride (Compound BH-3)

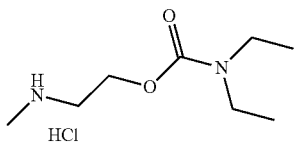
BH-3

2-[tert-butoxycarbonyl(methyl)amino]ethyl N,N-diethylcarbamate (436 mg, 1.77 mmol, Compound BH-2) was added to HCl in EA (17 mL, 1M). The mixture was stirred at 0° C. for 0.5 hr. Then the mixture was stirred at 25° C. for another 15.5 hrs and concentrated to afford 2-(methylamino)ethyl N,N-diethylcarbamate hydrochloride (230 mg, Compound BH-3) as a colorless oil.

Step 4: Preparation of 2-[chlorocarboyl(methyl)amino]ethyl N,N-diethylcarbamate (Intermediate BH)

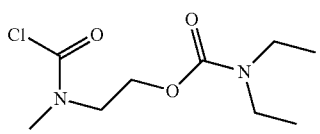
BH

Intermediate BH was prepared in analogy to Intermediate AP by using 2-(methylamino)ethyl N,N-diethylcarbamate hydrochloride (274 mg, Compound BH-3) instead of ethyl 2-(methylamino)acetate hydrochloride. The crude 2-[chlorocarbonyl(methyl)amino]ethyl N,N-diethylcarbamate (250 mg, Intermediate BH) was obtained and used for next step without further purification.

Intermediate BI

2-[Chlorocarboyl(methyl)amino]ethyl ethyl carbonate

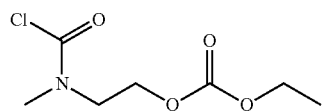
BI

Step 1: Preparation of tert-butyl N-(2-hydroxyethyl)-N-methyl-carbamate (Compound BI-1)

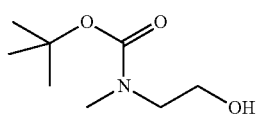
BI-1

To a solution of 2-(methylamino)ethanol (1 g, 13.31 mmol) in DCM (10 mL) was added Boc$_2$O (3.49 g, 15.98 mmol) at 25° C. The reaction mixture was stirred at 25° C. for 16 hrs, then concentrated to give the crude product, which was purified by column chromatography to afford tert-butyl N-(2-hydroxyethyl)-N-methyl-carbamate (1.6 g, Compound BI-1) as a colorless oil.

Step 2: Preparation of 2-[tert-butoxycarbonyl (methyl)amino]ethyl methyl carbonate (Compound BI-2)

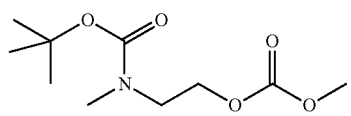
BI-2

To a solution of tert-butyl N-(2-hydroxyethyl)-N-methyl-carbamate (1 g, Compound BI-1), DMAP (0.1 g) and pyridine (1.15 g, 11.41 mmol) in EA (20 mL) was added methyl chloroformate (1.21 g, 11.15 mmol) dropwise at −10° C. The mixture was stirred at −10° C. for 1 hr. The reaction mixture was filtered and the filtrate was washed with 5% citric acid and brine. The organic layer was dried and concentrated to afford 2-[tert-butoxycarbonyl(methyl)amino]ethyl methyl carbonate (1.22 g, Compound BI-2) as a colorless oil.

Step 3: Preparation of ethyl 2-(methylamino)ethyl carbonate hydrochloride (Compound BI-3)

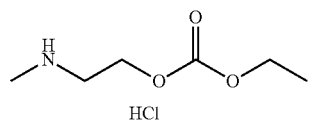
BI-3

2-[tert-butoxycarbonyl(methyl)amino]ethyl methyl carbonate (1.22 g, 4.94 mmol, Compound BI-2) was added to HCl in EA (10 mL, 40 mmol) and the mixture was stirred at 0° C. for 0.5 hr and at 25° C. for another 15.5 hrs. The reaction mixture was concentrated to afford ethyl 2-(methylamino)ethyl carbonate hydrochloride (1.06 g, Compound BI-3).

Step 4: Preparation of 2-[chlorocarboyl(methyl)amino]ethyl ethyl carbonate (Intermediate BI)

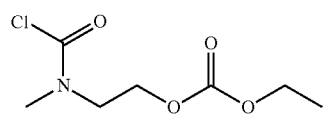
BI

Intermediate BI was prepared in analogy to Intermediate AP by using ethyl 2-(methylamino)ethyl carbonate hydrochloride (150 mg, Intermediate BI-3) instead of ethyl 2-(methylamino)acetate hydrochloride. The crude 2-[chlorocarbonyl(methyl)amino]ethyl ethyl carbonate (145 mg, Intermediate BI) was obtained and used for next step without further purification.

PREPARATIVE EXAMPLES

Example 1

6-Amino-9-benzyl-N-methyl-8-oxo-N-propyl-2-(propylsulfonimidoyl)purine-7-carboxamide

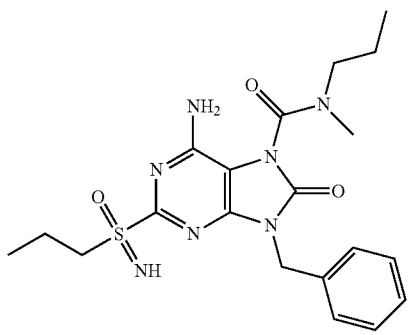

1

Method A:

Step 1: Preparation of 4-amino-3-benzyl-2-oxo-1H-imidazole-5-carbonitrile (Compound 1a)

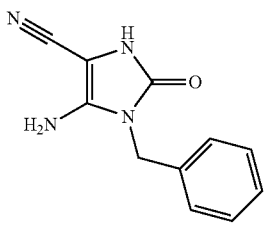

1a

To a solution of aminomalononitrilep-toluenesulfonate (25 g, 98.5 mmol, TCI, Catalog number: A1119-25G) in dry THF (100 mL) was added benzyl isocyanate (13.2 g, 98.5 mmol) and TEA (10.2 g, 79.0 mmol) at RT. After stirred at RT for 24 hrs, the reaction was concentrated in vacuo and the residue was partitioned between EtOAc (500 mL) and water (250 mL). The separated organic layer was washed with brine (50 mL) twice, and extracted with sodium hydroxide solution (50 mL, 1N) twice. The combined sodium hydroxide solution layer was neutralized with 10 wt. % sodium hydrogen sulfate solution and extracted with EtOAc. The separated organic layer was washed with brine, dried over Na$_2$SO$_4$, filtered and concentrated in vacuo. The residue was triturated in 2-isopropoxypropane and then the suspension was filtered to give 4-amino-3-benzyl-2-oxo-1H-imidazole-5-carbonitrile (15 g, Compound 1a) as a yellow solid. The product was used for the next step without further purification. MS obsd. (ESI$^+$) [(M+H)$^+$]: 215.

Step 2: Preparation of 6-amino-9-benzyl-2-sulfanyl-7H-purin-8-one (Compound 1b)

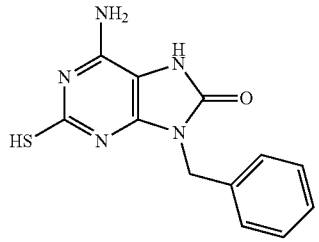

1b

To a solution of 4-amino-3-benzyl-2-oxo-1H-imidazole-5-carbonitrile (15.0 g, 70.0 mmol, Compound 1a) in THF (700 mL) was added benzoylisothiocyanate (28.6 g, 175.1 mmol, TCI, Catalog number: A11596-100G) dropwise. After stirred at RT for 12 hrs, the reaction mixture was concentrated in vacuo. The residue was triturated in diethyl ether (100 mL) and the resulting precipitate was collected by filtration.

To a solution of the obtained precipitate in THF (700 mL) was added sodium hydroxide (70 mL, 2N). The mixture was refluxed for 50 hrs, and then acidified to pH=3 with 10 wt. % aqueous sodium hydrogen sulfate solution. The resulting precipitate was collected by filtration to give a crude 6-amino-9-benzyl-2-sulfanyl-7H-purin-8-one (8.1 g, Compound 1b) as a yellow solid. The product was used for the next step without further purification. MS obsd. (ESI$^+$) [(M+H)$^+$]: 274.

Step 3: Preparation of 6-amino-9-benzyl-2-(2-propylsulfanyl)-7H-purin-8-one (Compound 1c)

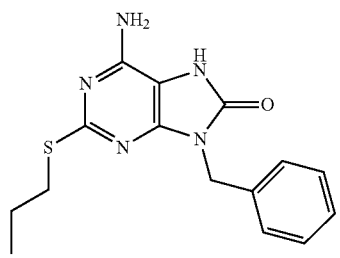

1c

To a solution of 6-amino-9-benzyl-2-sulfanyl-7H-purin-8-one (5.46 g, 20.0 mmol, Compound 1b) in DMF was added potassium carbonate (2.76 g, 20.0 mmol). And then 1-bromopropane (2.44 g, 20.0 mmol, TCI, Catalog number: B0638-500G) in DMF (5.0 mL) was slowly added to previous solution. After stirred at RT for 12 hrs, the reaction mixture was poured into water (200 mL), then acidified with 10 wt. % aqueous sodium hydrogen sulfate solution and extracted with EtOAc (100 mL) twice. The organic layer was washed with brine, dried over Na$_2$SO$_4$ and concentrated in vacuo to give the crude product, which was purified by flash chromatography on silica gel to give 6-amino-9-benzyl-2-(2-propylsulfanyl)-7H-purin-8-one (4.8 g, Compound 1c) as a white solid. MS obsd. (ESI$^+$) [(M+H)$^+$]: 316.

45

Step 4: Preparation of 6-amino-9-benzyl-2-propyl-sulfinyl-7H-purin-8-one (Compound 1d)

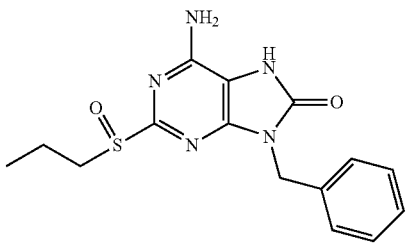

1d

To a suspension of compound 6-amino-9-benzyl-2-(2-propylsulfanyl)-7H-purin-8-one (2.7 g, 8.7 mmol, Compound 1c) in DCM/MeOH (500 mL, V/V=1:1) was added 3-chloroperbenzoic acid (2.15 g, 8.7 mmol, 70% purity, Aldrich, Catalog number: 273031-100G). After reaction mixture was stirred for 2 hrs, the volume of reaction mixture was reduced in vacuo to about 50 mL. The resulting precipitate was collected by filtration, washed with methanol and dried to give 6-amino-9-benzyl-2-propylsulfinyl-7H-purin-8-one (1.0 g, Compound 1d) as a white solid. The product was used for the next step without further purification. MS obsd. (ESI$^+$) [(M+H)$^+$]: 332.

Step 5: Preparation of 6-amino-9-benzyl-2-(propyl-sulfonimidoyl)-7H-purin-8-one (Compound 1e)

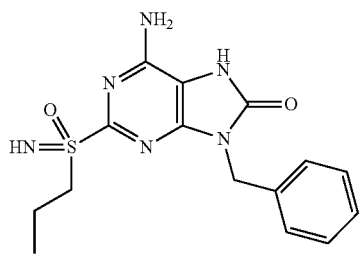

1e

To a solution of 6-amino-9-benzyl-2-propylsulfinyl-7H-purin-8-one (1.52 g, 4.6 mmol, Compound 1d) in Eaton's reagent (40 mL, phosphorus pentoxide, 7.5 wt. % in methanesulphonic acid, Aldrich, Catalog number: 380814-100ML) was added sodium azide (360 mg, 5.5 mmol) at 50° C. After being stirred at this temperature for 30 minutes, the reaction mixture was cooled to RT and poured into sat. aqueous sodium bicarbonate solution. The reaction mixture was extracted with n-BuOH (100 mL) twice, and the organic phase was concentrated in vacuo. The residue was submitted for purification by prep-HPLC to give 6-amino-9-benzyl-2-(propylsulfonimidoyl)-7H-purin-8-one (1.2 g, Compound 1e) as a white solid. $^1$H NMR (400 MHz, DMSO-d$_6$) δ ppm: 10.65 (br. s., 1H), 7.26-7.37 (m, 5H), 6.98 (br. s., 2H), 4.97 (s, 2H), 4.02 (s, 1H), 3.33 (t, J=7.53 Hz, 2H), 1.55-1.74 (m, 2H), 0.92 (t, J=7.53 Hz, 3H). MS obsd. (ESI$^+$) [(M$^+$H)$^+$]: 347.

46

Separation of compound 1e by chiral HPLC afforded Compound 1e-A (slower eluting, 500 mg) and Compound 1e-B (faster eluting, 490 mg) as white solid. (Separation condition: methanol 5%-40% (0.05% DEA)/CO$_2$ on Chiral-Pak AS-3 column.)

Compound 1e-A: $^1$H NMR (DMSO-d$_6$, 400 MHz) δ ppm: 10.56 (s, 1H), 7.21-7.46 (m, 5H), 7.03 (s, 2H), 4.96 (s, 2H), 4.04 (s, 1H), 3.25-3.33 (m, 2H), 1.59-1.67 (m, 2H), 0.92 (t, J=7.4 Hz, 3H).

Compound 1e-B: $^1$H NMR (DMSO-d$_6$, 400 MHz) δ ppm: 10.57 (s, 1H), 7.23-7.39 (m, 5H), 6.97 (s, 2H), 4.96 (s, 2H), 4.05 (s, 1H), 3.31-3.30 (m, 2H), 1.49-1.74 (m, 2H), 0.91 (t, J=7.4 Hz, 3H).

Step 6: Preparation of 6-amino-9-benzyl-N-methyl-8-oxo-N-propyl-2-(propylsulfonimidoyl)purine-7-carboxamide (Example 1)

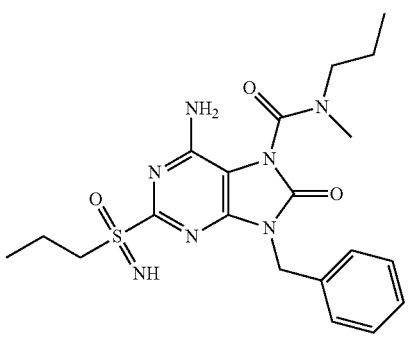

1

To a solution of 6-amino-9-benzyl-2-(propylsulfonimidoyl)-7H-purin-8-one (300 mg, Compound 1e), pyridine (329 mg, 4.2 mmol) and DIPEA (538 mg, 4.2 mmol) in NMP (5 mL) was added N-methyl-N-propyl-carbamoyl chloride (564 mg, 4.2 mmol, Intermediate AA) at RT. The mixture was stirred at RT for 10 hrs. The reaction mixture was concentrated and the residue was purified by prep-HPLC to give 6-amino-9-benzyl-N-methyl-8-oxo-N-propyl-2-(propylsulfonimidoyl)purine-7-carboxamide (108 mg, Example 1) as a white solid. $^1$H NMR (400 MHz, DMSO-d$_6$) δ ppm: 7.45-7.24 (m, 5H), 6.89 (s, 2H), 5.01 (s, 2H), 4.17 (s, 1H), 3.44-3.34 (m, 2H), 3.36-3.34 (m, 2H), 3.10-3.00 (m, 3H), 1.74-1.52 (m, 4H), 1.01-0.72 (m, 6H). MS obsd. (ESI$^+$) [(M+H)$^+$]: 446.

Separation of compound of Example 1 by chiral HPLC afforded Example 1-A (slower eluting, 50 mg) and Example 1-B (faster eluting, 40 mg) as white solid with isopropanol 5%-40% (0.05% DEA)/CO$_2$ on ChiralPak AD-3 column.

Example 1-A: $^1$H NMR (400 MHz, DMSO-d$_6$) δ ppm: 7.44-7.24 (m, 5H), 6.89 (s, 2H), 5.01 (s, 2H), 4.17 (s, 1H), 3.44-3.37 (m, 2H), 3.37-3.35 (m, 2H), 3.10-3.00 (m, 3H), 1.74-1.52 (m, 4H), 1.00-0.72 (m, 6H). MS obsd. (ESI$^+$) [(M+H)$^+$]: 446.

Example 1-B: $^1$H NMR (400 MHz, DMSO-d$_6$) δ ppm: 7.45-7.26 (m, 5H), 6.88 (s, 2H), 5.01 (s, 2H), 4.15 (s, 1H), 3.44-3.36 (m, 2H), 3.34 (s, 2H), 3.10-3.01 (m, 3H), 1.77-1.52 (m, 4H), 1.02-0.67 (m, 6H). MS obsd. (ESI$^+$) [(M+H)$^+$]: 446.

Method B: Alternative method to prepare 6-amino-9-benzyl-2-(propylsulfonimidoyl)-7H-purin-8-one (Compound 1e)

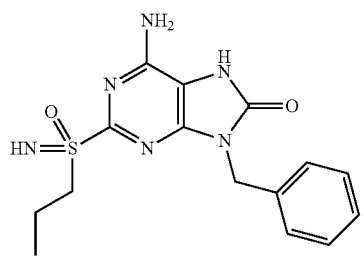

Step 1: Preparation of N-benzyl-6-chloro-5-nitro-2-propylsulfanyl-pyrimidin-4-amine (Compound 1f)

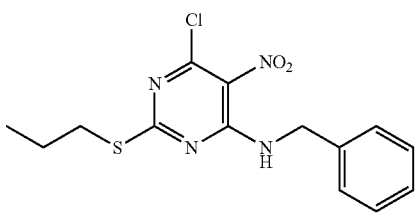

To a solution of 4,6-dichloro-5-nitro-2-propylsulfanylpyrimidine (150.0 g, 559.5 mmol) and DIPEA (108.5 g, 839.2 mmol) in THF (1.5 L) was added phenylmethanamine (60.0 g, 559.5 mmol) in THF (200 mL) slowly at −78° C. After addition, the mixture was warmed to 25° C., and stirred at this temperature for 16 hrs. The resulting mixture was diluted with EA (1 L), washed with water (400 mL) three times and brine (500 mL). The separated organic phase was dried over Na$_2$SO$_4$, filtered and concentrated in vacuo to give N-benzyl-6-chloro-5-nitro-2-propylsulfanyl-pyrimidin-4-amine (180.0 g, Compound 1f) as a yellow solid and used for next step without further purification. MS obsd. (ESI$^+$) [(M+H)$^+$]: 339.1.

Step 2: Preparation of N4-benzyl-6-chloro-2-propylsulfanyl-pyrimidine-4,5-diamine (Compound 1g)

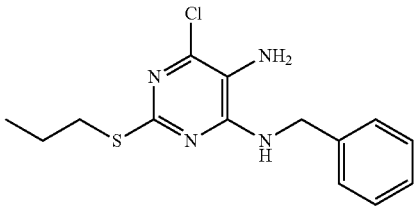

To a solution of N-benzyl-6-chloro-5-nitro-2-propylsulfanyl-pyrimidin-4-amine (180 g, Compound 1f) and HOAc (319 g, 5.31 mol) in THF (3.0 L) was added Zn (174 g, 2.66 mol) slowly at 25° C. After the addition, the mixture was stirred at 25° C. for 16 hrs. The reaction was filtered and the filtrate was basified with saturated aq. NaHCO$_3$ (800 mL), extracted with EA (400 mL) three times, dried over Na$_2$SO$_4$ and concentrated in vacuo. The residue was purified by silica gel chromatography to give N4-benzyl-6-chloro-2-propylsulfanyl-pyrimidine-4,5-diamine (125 g, Compound 1g) as a brown solid. MS obsd. (ESI$^+$) [(M+H)$^+$]: 309.1.

Step 3: Preparation of 9-benzyl-6-chloro-2-propylsulfanyl-7H-purin-8-one (Compound 1h)

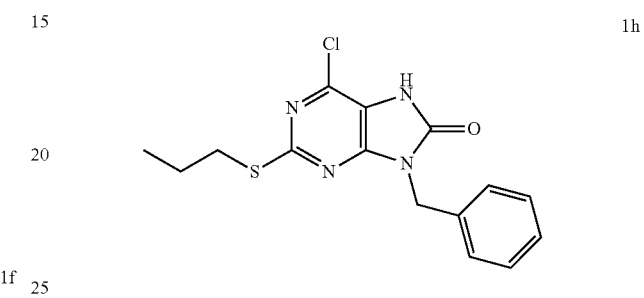

To a solution of N-benzyl-6-chloro-2-(propylsulfanyl)pyrimidine-4,5-diamine (72.0 g, 233.1 mmol, Compound 1g) and CDI (75.2 g, 233.1 mmol) in THF (800 mL) was stirred at 80° C. for 16 hrs. The resulting mixture was diluted with EA (400 mL), washed with water (200 mL) twice and brine (200 mL). The separated organic layer was dried over Na$_2$SO$_4$, concentrated in vacuo. The residue was washed with MTBE (200 mL) to give 9-benzyl-6-chloro-2-propylsulfanyl-7H-purin-8-one (58.0 g, Compound 1h) as a white solid and was used in next step without further purification. MS obsd. (ESI$^+$) [(M+H)$^+$]: 335.1.

Step 4: Preparation of 9-benzyl-6-[(4-methoxyphenyl)methylamino]-2-propylsulfanyl-7H-purin-8-one (Compound 1i)

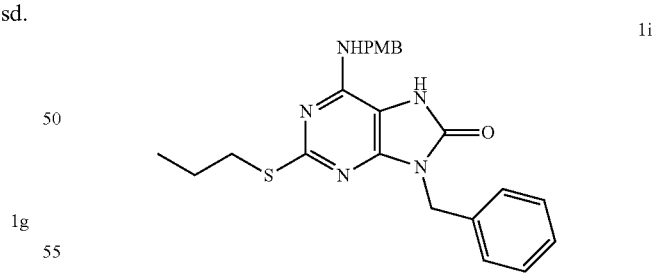

A solution of 9-benzyl-6-chloro-2-propylsulfanyl-7H-purin-8-one (58.0 g, Compound 1h) and PMBNH$_2$ (54.7 g, 398.42 mmol) in n-BuOH (600 mL) was stirred at 120° C. for 20 hrs. The reaction was concentrated and the residue was washed with MTBE (400 mL) to give 9-benzyl-6-[(4-methoxyphenyl)methylamino]-2-propylsulfanyl-7H-purin-8-one (75 g, Compound 1i) as a white solid and was used in next step without further purification. MS obsd. (ESI$^+$) [(M+H)$^+$]: 436.2.

Step 5: Preparation of 6-amino-9-benzyl-2-propyl-sulfanyl-7H-purin-8-one (Compound 1c)

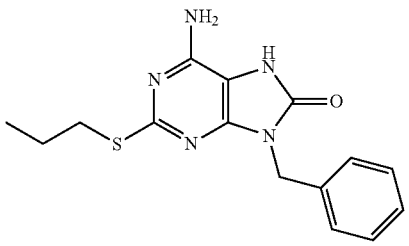

1c

9-Benzyl-6-[(4-methoxyphenyl)methylamino]-2-propyl-sulfanyl-7H-purin-8-one (87.0 g, Compound 1i) in TFA (200 mL) was stirred at 80° C. for 16 hrs. The resulting reaction mixture was concentrated, basified with saturated aq. NaHCO₃ (600 mL). The resulting precipitate was collected by filtration and washed with (PE/DCM=2:1, 400 mL) to give 6-amino-9-benzyl-2-propylsulfanyl-7H-purin-8-one (38.0 g, Compound 1c) as a white solid. MS obsd. (ESI⁺) [(M+H)⁺]: 316.1.

Step 6: Preparation of 6-amino-9-benzyl-2-propyl-sulfinyl-7H-purin-8-one (Compound 1d)

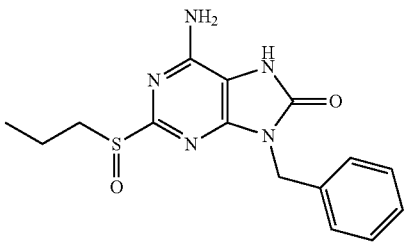

1d

To a solution of m-CPBA (22.98 g, 113.2 mmol) in THF (50 mL) was added dropwise to a suspension of 6-amino-9-benzyl-2-propylsulfanyl-7H-purin-8-one (35.0 g, compound 1c) in THF (200 mL) at 0° C. After the addition, the reaction mixture was stirred at 25° C. for 0.5 hr. The mixture was filtered and washed with MeCN (400 mL), MTBE (500 mL) to give 6-amino-9-benzyl-2-propylsulfinyl-7H-purin-8-one (35.1 g, Compound 1d) as a white solid, which was used for the next step without further purification. MS obsd. (ESI⁺) [(M+H)⁺]: 332.1.

Step 7: Preparation of 6-amino-9-benzyl-2-(propyl-sulfonimidoyl)-7H-purin-8-one (Compound 1e)

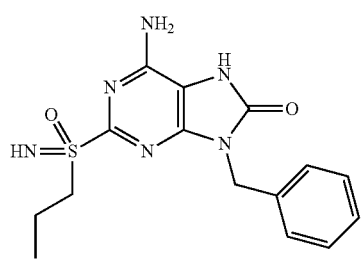

1e

To a solution of 6-amino-9-benzyl-2-propylsulfinyl-7H-purin-8-one (34.0 g, Compound 1d) in Eaton's reagent (170.0 mL, 7.5 wt. % in methanesulphonic acid) was added NaN₃ (15.34 g, 253.97 mmol) at 60° C. slowly. Then the mixture was stirred at 60° C. for 30 mins. The resulting reaction mixture was cooled to 25° C., poured into ice cold NH₃.H₂O (500 mL, 1 mol/L), extracted with n-BuOH (100 mL) four times and concentrated in vacuo. The residue was purified by prep-HPLC to give 6-amino-9-benzyl-2-(propylsulfonimidoyl)-7H-purin-8-one (10 g, Compound 1e). ¹H NMR (400 MHz, DMSO-d₆) δ ppm: 10.65 (br. s., 1H), 7.26-7.37 (m, 5H), 6.98 (br. s., 2H), 4.97 (s, 2H), 4.02 (s, 1H), 3.33 (t, J=7.53 Hz, 2H), 1.55-1.74 (m, 2H), 0.92 (t, J=7.53 Hz, 3H). MS obsd. (ESI⁺) [(M⁺H)⁺]: 347.

Example 2

6-Amino-9-benzyl-N-(2-methoxyethyl)-N-methyl-8-oxo-2-(propylsulfonimidoyl)purine-7-carboxamide

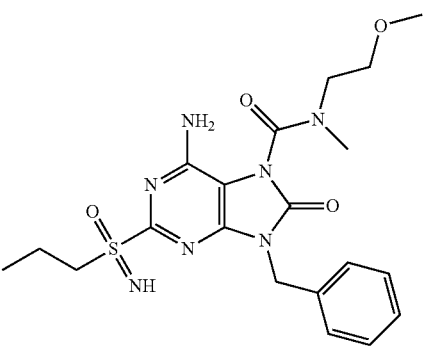

2

The title compound was prepared in analogy to Example 1, Method A, Step 6 by using N-(2-methoxyethyl)-N-methyl-carbamoyl chloride (Intermediate AB) instead of N-methyl-N-propyl-carbamoyl chloride (Intermediate AA). 6-Amino-9-benzyl-N-(2-methoxyethyl)-N-methyl-8-oxo-2-(propyl sulfonimidoyl)purine-7-carboxamide (120 mg, Example 2) was obtained as a white solid. ¹H NMR (400 MHz, DMSO-d₆) δ ppm: 7.27-7.39 (m, 5H), 6.89 (br. s., 1H), 6.78 (br. s., 1H), 5.00 (s, 2H), 4.16 (br. d, J=4 Hz, 1H), 3.62 (br. dd, J=4, 12 Hz, 3H), 3.28-3.42 (m, 6H), 3.12 (d, J=12 Hz, 3H), 3.05 (s, 1H), 1.58-1.72 (m, 2H), 0.93 (t, J=8 Hz, 3H). MS obsd. (ESI⁺) [(M+H)⁺]: 462.

Separation of compound of Example 2 by chiral HPLC afforded Example 2-A (faster eluting, 33 mg) and Example 2-B (slower eluting, 46 mg) as white solid with methanol 5%-40% (0.05% DEA)/CO₂ on ChiralPak OJ-3 column.

Example 2-A: ¹H NMR (400 MHz, DMSO-d₆) δ ppm: 7.27-7.39 (m, 5H), 6.89 (br. s., 1H), 6.78 (br. s., 1H), 5.00 (s, 2H), 4.16 (br. d, J=4 Hz, 1H), 3.62 (br. dd, J=4, 12 Hz, 2H), 3.28-3.42 (m, 6H), 3.12 (d, J=12 Hz, 3H), 3.05 (s, 1H), 1.58-1.72 (m, 2H), 0.93 (t, J=8 Hz, 3H). MS obsd. (ESI⁺) [(M+H)⁺]: 462.

Example 2-B: ¹H NMR (400 MHz, DMSO-d₆) δ ppm: 7.27-7.39 (m, 5H), 6.89 (br. s., 1H), 6.78 (br. s., 1H), 5.00 (s, 2H), 4.16 (br. d, J=4 Hz, 1H), 3.62 (br. dd, J=4, 12 Hz, 2H), 3.28-3.42 (m, 6H), 3.12 (d, J=12 Hz, 3H), 3.05 (s, 1H), 1.58-1.72 (m, 2H), 0.93 (t, J=8 Hz, 3H). MS obsd. (ESI⁺) [(M+H)⁺]: 462.

Example 3

6-Amino-9-benzyl-N-ethyl-8-oxo-N-propyl-2-(propylsulfonimidoyl)purine-7-carboxamide

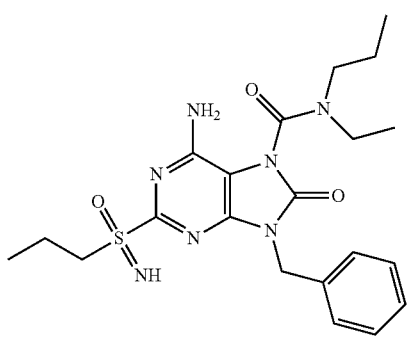

The title compound was prepared in analogy to Example 1, Method A, Step 6 by using N-ethyl-N-propyl-carbamoyl chloride (Intermediate AC) instead of N-methyl-N-propyl-carbamoyl chloride (Intermediate AA). 6-Amino-9-benzyl-N-ethyl-8-oxo-N-propyl-2-(propylsulfonimidoyl)purine-7-carboxamide (51 mg, Example 3) was obtained as a white solid. $^1$H NMR (400 MHz, DMSO-$d_6$) δ ppm: 7.27-7.39 (m, 5H), 6.85 (br. s., 2H), 4.99 (s, 2H), 4.20 (br. d, J=8.0 Hz, 1H), 3.13-3.54 (m, 4H), 1.46-1.72 (m, 4H), 1.30-1.39 (m, 1H), 1.00-1.26 (m, 6H), 0.81-0.95 (m, 5H), 0.73 (t, J=8 Hz, 1H). MS obsd. (ESI$^+$) [(M+H)$^+$]: 474.

Example 4

6-Amino-9-benzyl-7-[4-(1-piperidyl)piperidine-1-carbonyl]-2-(propylsulfonimidoyl)purin-8-one

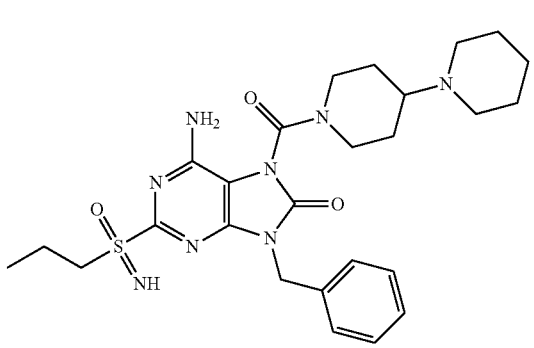

The title compound was prepared in analogy to Example 1, Method A, Step 6 by using (1,4'-bipiperidine)-1'-carbonyl chloride instead of N-methyl-N-propyl-carbamoyl chloride (Intermediate AA). 6-Amino-9-benzyl-7-[4-(1-piperidyl)piperidine-1-carbonyl]-2-(propylsulfonimidoyl)purin-8-one (55 mg, Example 4) was obtained as a white powder. $^1$H NMR (400 MHz, DMSO-$d_6$) δ ppm: 7.39-7.27 (m, 5H), 6.97 (br. s., 2H), 4.99 (s, 2H), 4.20 (br. s., 2H), 3.85 (d, J=12.5 Hz, 1H), 3.43-3.15 (m, 3H), 2.96 (t, J=12.3 Hz, 2H), 2.56 (m, 4H), 1.83 (m, 1H), 1.79-1.54 (m, 4H), 1.50 (br. s., 4H), 1.45-1.33 (m, 3H), 0.93 (t, J=7.4 Hz, 3H). MS obsd. (ESI$^+$) [(M+H)$^+$]: 541.2.

Example 5

6-Amino-9-benzyl-N-ethyl-N-(2-methoxyethyl)-8-oxo-2-(propylsulfonimidoyl)purine-7-carboxamide

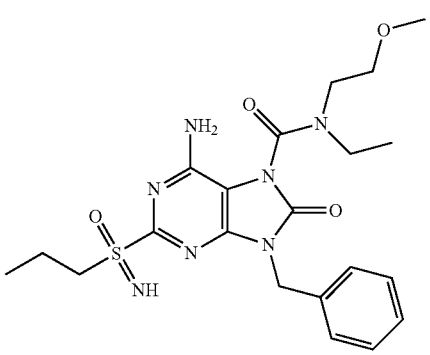

The title compound was prepared in analogy to Example 1, Method A, Step 6 by using N-ethyl-N-(2-methoxyethyl) carbamoyl chloride (Intermediate AD) instead of N-methyl-N-propyl-carbamoyl chloride (Intermediate AA). 6-Amino-9-benzyl-N-ethyl-N-(2-methoxyethyl)-8-oxo-2-(propylsulfonimidoyl)purine-7-carboxamide (34 mg, Example 5) was obtained as a white powder. $^1$H NMR (400 MHz, DMSO-$d_6$) δ ppm: 7.39-7.28 (m, 5H), 6.89 (br. s., 1H), 6.74 (br. s., 1H), 4.99 (s, 2H), 4.17 (d, J=8.1 Hz, 1H), 3.67 (br. s., 2H), 3.63-3.51 (m, 2H), 3.50-3.34 (m, 4H), 3.29 (s, 1H), 3.11 (s, 2H), 1.73-1.59 (m, 2H), 1.23-1.07 (m, 3H), 0.93 (t, J=7.5 Hz, 3H). MS obsd. (ESI$^+$) [(M+H)$^+$]: 476.3.

Example 6

6-Amino-9-benzyl-N-butyl-N-ethyl-8-oxo-2-(propylsulfonimidoyl)purine-7-carboxamide

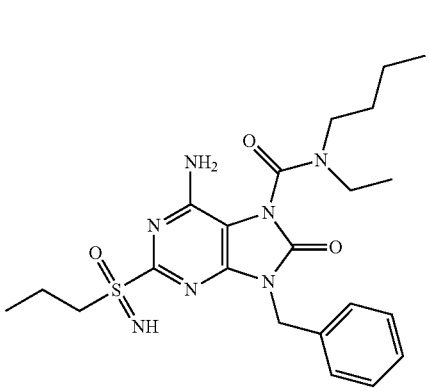

The title compound was prepared in analogy to Example 1, Method A, Step 6 by using N-butyl-N-ethyl-carbamoyl chloride (Intermediate AE) instead of N-methyl-N-propyl-carbamoyl chloride (Intermediate AA). 6-Amino-9-benzyl-N-butyl-N-ethyl-8-oxo-2-(propylsulfonimidoyl)purine-7-carboxamide (51 mg, Example 6) was obtained as a white solid. $^1$H NMR (400 MHz, DMSO-$d_6$) δ ppm: 7.27-7.39 (m, 5H), 6.85 (br. s., 2H), 4.99 (s, 2H), 4.20 (br. d, J=8.0 Hz, 1H), 3.13-3.54 (m, 4H), 1.46-1.72 (m, 4H), 1.30-1.39 (m, 1H), 1.00-1.26 (m, 6H), 0.81-0.95 (m, 5H), 0.73 (t, J=8 Hz, 1H). MS obsd. (ESI⁺) [(M+H)⁺]: 474.

Example 7

6-Amino-9-benzyl-N-(2-methoxyethyl)-8-oxo-N-propyl-2-(propylsulfonimidoyl)purine-7-carboxamide

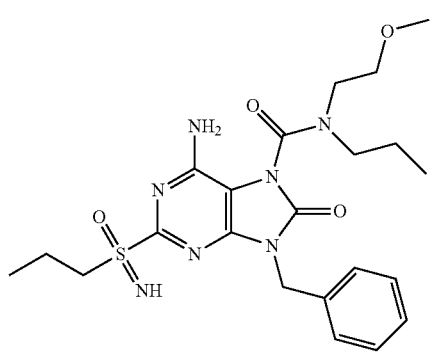

The title compound was prepared in analogy to Example 1, Method A, Step 6 by using N-ethyl-N-(2-methoxyethyl)carbamoyl chloride (Intermediate AF) instead of N-methyl-N-propyl-carbamoyl chloride (Intermediate AA). 6-amino-9-benzyl-N-(2-methoxyethyl)-8-oxo-N-propyl-2-(propylsulfonimidoyl)purine-7-carboxamide (35 mg, Example 7) was obtained as a white powder. ¹HNMR (400 MHz, DMSO-d₆) δ ppm: 7.40-7.28 (m, 5H), 6.89 (br. s., 1H), 6.75 (br. s., 1H), 5.00 (d, J=5.5 Hz, 2H), 4.24-4.16 (m, 1H), 3.77 (br. s., 1H), 3.67 (br. s., 1H), 3.62-3.53 (m, 1H), 3.42-3.27 (m, 5H), 3.23-3.02 (m, 3H), 1.66-1.38 (m, 4H), 0.96-0.70 (m, 6H). MS obsd. (ESI⁺) [(M+H)⁺]: 490.5.

Example 8

6-Amino-9-benzyl-N,N-bis(2-methoxyethyl)-8-oxo-2-(propylsulfonimidoyl)purine-7-carboxamide

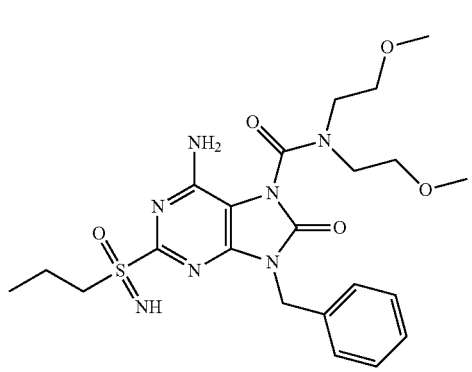

The title compound was prepared in analogy to Example 1, Method A, Step 6 by using bis(2-methoxyethyl)carbamic chloride (Intermediate AG) instead of N-methyl-N-propyl-carbamoyl chloride (Intermediate AA). 6-Amino-9-benzyl-N,N-bis(2-methoxyethyl)-8-oxo-2-(propylsulfonimidoyl)purine-7-carboxamide (35 mg, Example 8) was obtained as a white powder. ¹H NMR (400 MHz, DMSO-d₆) δ ppm: 7.40-7.28 (m, 5H), 6.83 (br. s., 2H), 4.99 (s, 2H), 3.71 (br. s., 3H), 3.52-3.27 (m, 11H), 3.09 (s, 3H), 1.73-1.59 (m, 2H), 0.93 (t, J=7.5 Hz, 3H). MS obsd. (ESI⁺) [(M+H)⁺]: 506.

Example 9

6-Amino-7-(azetidine-1-carbonyl)-9-benzyl-2-(propylsulfonimidoyl)purin-8-one

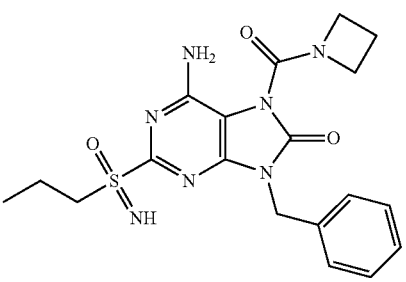

The title compound was prepared in analogy to Example 1, Method A, Step 6 by using azetidine-1-carbonyl chloride (Intermediate AH) instead of N-methyl-N-propyl-carbamoyl chloride (Intermediate AA). 6-Amino-7-(azetidine-1-carbonyl)-9-benzyl-2-(propylsulfonimidoyl)purin-8-one (120 mg, Example 9) was obtained as a white powder. ¹HNMR (400 MHz, DMSO-d₆) δ ppm: 7.02-7.43 (m, 7H), 4.99 (s, 2H), 4.31 (t, J=7.65 Hz, 2H), 4.08-4.23 (m, 3H), 3.34-3.41 (m, 2H), 2.28 (m, 2H), 1.56-1.73 (m, 2H), 0.93 (t, J=7.40 Hz, 3H). MS obsd. (ESI⁺) [(M+H)⁺]: 430.

Example 10

6-Amino-9-benzyl-N-isopropyl-N-methyl-8-oxo-2-(propylsulfonimidoyl)purine-7-carboxamide

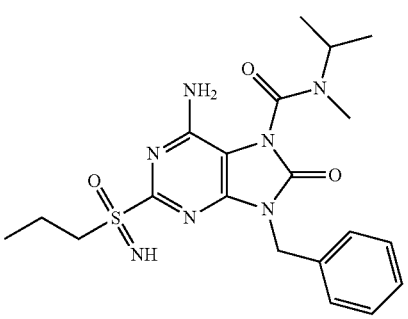

The title compound was prepared in analogy to Example 1, Method A, Step 6 by using N-isopropyl-N-methyl-carbamoyl chloride (Intermediate AI) instead of N-methyl-N-propyl-carbamoyl chloride (Intermediate AA). 6-Amino-9-benzyl-N-isopropyl-N-methyl-8-oxo-2-(propylsulfonimidoyl)purine-7-carboxamide (97 mg, Example 10) was obtained as a white solid. ¹H NMR (400 MHz, DMSO-d₆) δ ppm: 7.27-7.39 (m, 5H), 6.87 (br. s., 2H), 4.99 (s, 2H), 4.38-4.45 (m, 1H), 4.09-4.21 (m, 1H), 3.29-3.43 (m, 2H), 2.89-2.95 (m, 3H), 1.58-1.73 (m, 2H), 1.21 (br d, J=8 Hz, 6H), 0.93 (t, J=8 Hz, 3H). MS obsd. (ESI⁺) [(M+H)⁺]: 446.

Example 11

6-Amino-9-benzyl-7-(4-methylpiperazine-1-carbonyl)-2-(propylsulfonimidoyl)purin-8-one

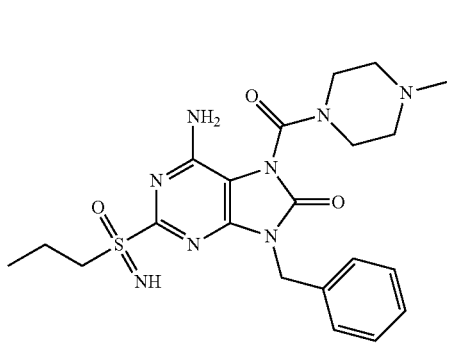

The title compound was prepared in analogy to Example 1, Method A, Step 6 by using 4-methylpiperazine-1-carbonyl chloride instead of N-methyl-N-propyl-carbamoyl chloride (Intermediate AA). 6-Amino-9-benzyl-7-(4-methylpiperazine-1-carbonyl)-2-(propylsulfonimidoyl)purin-8-one (59.5 mg, Example 11) was obtained as a yellow solid. ¹H NMR (400 MHz, DMSO-d₆) δ ppm: 7.39-7.31 (m, 5H), 6.99 (s, 2H), 4.98 (s, 2H), 4.18 (s, 1H), 3.58-3.49 (m, 6H), 2.42 (m, 4H), 2.22 (s, 3H), 1.66-1.61 (m, 2H), 0.95-0.91 (t, J=7.2 Hz, 3H). MS obsd. (ESI⁺) [(M+H)⁺]: 473.

Example 12

6-Amino-9-benzyl-N-(3-methoxypropyl)-N-methyl-8-oxo-2-(propylsulfonimidoyl)purine-7-carboxamide

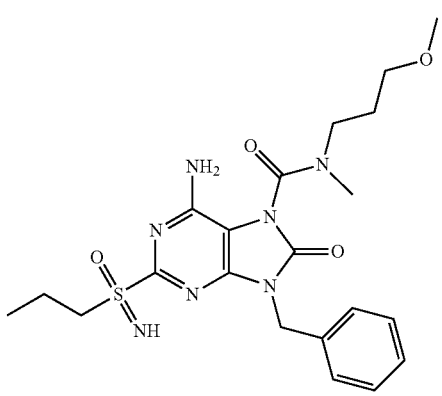

The title compound was prepared in analogy to Example 1, Method A, Step 6 by using N-(3-methoxypropyl)-N-methyl-carbamoyl chloride instead of N-methyl-N-propyl-carbamoyl chloride (Intermediate AA). 6-Amino-9-benzyl-N-(3-methoxypropyl)-N-methyl-8-oxo-2-(propylsulfonimidoyl)purine-7-carboxamide (92.2 mg, Example 12) was obtained as a white solid. ¹H NMR (400 MHz, DMSO-d₆) δ ppm: 7.23-7.45 (m, 5H), 6.94 (s., 2H), 4.93-5.08 (m, 2H), 4.19 (s, 1H), 3.30-3.62 (m, 6H), 3.25 (s, 3H), 3.02-3.10 (m, 3H), 1.74-1.90 (m, 2H), 1.55-1.77 (m, 2H), 0.98-0.82 (m, 3H). MS obsd. (ESI⁺) [(M+H)⁺]: 476.3.

Example 13

6-Amino-9-benzyl-N-isobutyl-N-methyl-8-oxo-2-(propylsulfonimidoyl)purine-7-carboxamide

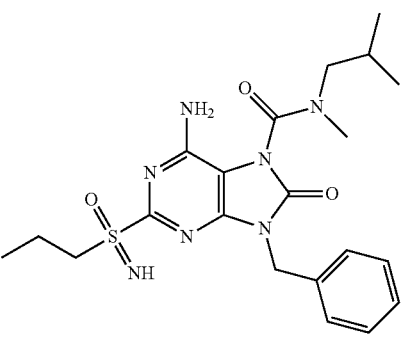

The title compound was prepared in analogy to Example 1, Method A, Step 6 by using N-isobutyl-N-methyl-carbamoyl chloride (Intermediate AL) instead of N-methyl-N-propyl-carbamoyl chloride (Intermediate AA). 6-Amino-9-benzyl-N-isobutyl-N-methyl-8-oxo-2-(propylsulfonimidoyl)purine-7-carboxamide (64 mg, Example 13) was obtained as a white solid. ¹H NMR (400 MHz, DMSO-d₆) δ ppm: 7.27-7.40 (m, 5H), 6.89 (br. s., 2H), 5.00 (s, 2H), 4.16 (br. s., 1H), 3.25-3.44 (m, 4H), 3.07 (s, 2H), 3.03 (s, 1H), 1.87-2.09 (m, 1H), 1.57-1.74 (m, 2H), 0.75-0.99 (m, 9H). MS obsd. (ESI⁺) [(M+H)⁺]: 460.

Example 14

Ethyl 2-[[6-amino-9-benzyl-8-oxo-2-(propylsulfonimidoyl)purine-7-carbonyl]-methyl-amino]acetate

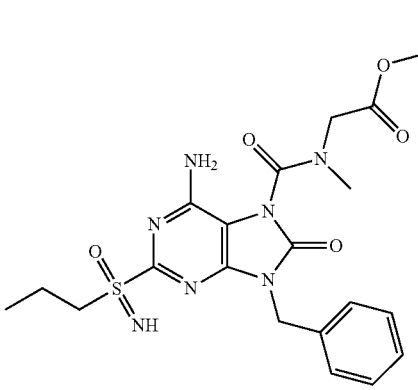

The title compound was prepared in analogy to Example 1, Method A, Step 6 by using ethyl 2-((chlorocarbonyl)(methyl)amino)acetate (Intermediate AP) instead of N-methyl-N-propyl-carbamoyl chloride (Intermediate AA). Ethyl 2-[[6-amino-9-benzyl-8-oxo-2-(propylsulfonimidoyl)purine-7-carbonyl]-methyl-amino]acetate (38 mg, Example 14) was obtained as a light yellow powder. ¹H NMR (400 MHz, DMSO-d₆) δ ppm: 7.41-7.27 (m, 5H), 6.82 (br. s., 1H), 5.04-4.95 (m, 2H), 4.35 (br. s., 1H), 4.28 (br. s., 1H), 4.23-4.16 (m, 2H), 4.08 (q, J=7.2 Hz, 1H), 3.43-3.28 (m, 3H), 3.15 (s, 2H), 3.08 (s, 1H), 1.71-1.58 (m, 2H), 1.24 (t, J=7.0 Hz, 2H), 1.12 (t, J=7.0 Hz, 1H), 0.93 (t, J=7.4 Hz, 3H). MS obsd. (ESI⁺) [(M+H)⁺]: 490.

Example 15

Ethyl 3-[[6-amino-9-benzyl-8-oxo-2-(propylsulfonimidoyl)purine-7-carbonyl]-methyl-amino]propanoate

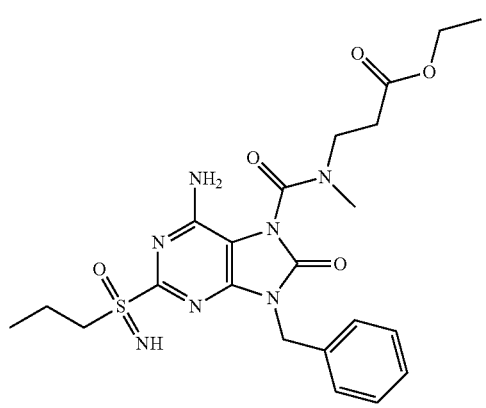

The title compound was prepared in analogy to Example 1, Method A, Step 6 by using ethyl 3-((chlorocarbonyl)(methyl)amino)propanoate instead of N-methyl-N-propyl-carbamoyl chloride (Intermediate AA). Ethyl 3-[[6-amino-9-benzyl-8-oxo-2-(propylsulfonimidoyl)purine-7-carbonyl]-methyl-amino]propanoate (35 mg, Example 15) was obtained as a white powder. $^1$H NMR (400 MHz, DMSO-d$_6$) δ ppm: 7.43-7.26 (m, 5H), 6.93 (br. s., 2H), 4.99 (s, 2H), 4.16 (s, 1H), 4.08 (q, J=7.1 Hz, 1H), 3.99 (d, J=7.0 Hz, 1H), 3.67 (br. s., 2H), 3.40-3.29 (m, 2H), 3.08 (s, 2H), 2.99 (s, 1H), 2.71 (t, J=6.4 Hz, 2H), 1.74-1.56 (m, 2H), 1.27-1.05 (m, 3H), 0.93 (t, J=7.5 Hz, 3H). MS obsd. (ESI$^+$) [(M+H)$^+$]: 504.

Example 16 tert-Butyl 3-[[6-amino-9-benzyl-8-oxo-2-(propylsulfonimidoyl)purine-7-carbonyl]-methyl-amino]propanoate

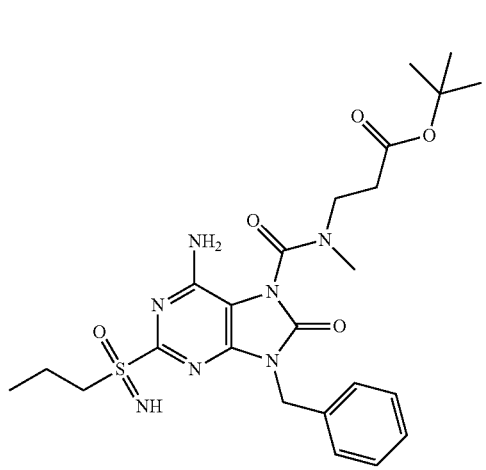

The title compound was prepared in analogy to Example 1, Method A, Step 6 by using tert-butyl 3-[chlorocarbonyl(methyl)amino]propanoate (Intermediate AR) instead of N-methyl-N-propyl-carbamoyl chloride (Intermediate AA). tert-Butyl 3-[[6-amino-9-benzyl-8-oxo-2-(propylsulfonimidoyl)purine-7-carbonyl]-methyl-amino]propanoate (60 mg, Example 16) was obtained as a white powder. $^1$H NMR (400 MHz, DMSO-d$_6$) δ ppm: 7.41-7.27 (m, 5H), 6.93 (br. s., 2H), 4.99 (s, 2H), 4.15 (s, 1H), 3.64 (br. s., 2H), 3.51-3.33 (m, 2H), 3.08 (s, 2H), 2.98 (s, 1H), 2.62 (t, J=6.9 Hz, 2H), 1.71-1.57 (m, 2H), 1.41 (s, 6H), 1.34 (s, 3H), 0.93 (t, J=7.4 Hz, 3H). MS obsd. (ESI$^+$) [(M+H)$^+$]: 532.

Example 17

Ethyl(2S)-2-[[6-amino-9-benzyl-8-oxo-2-(propylsulfonimidoyl)purine-7-carbonyl]-methyl-amino]propanoate

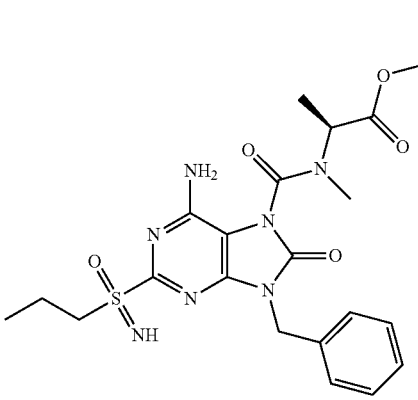

The title compound was prepared in analogy to Example 1, Method A, Step 6 by using ethyl (2S)-2-[chlorocarbonyl(methyl)amino]propanoate (Intermediate AS) instead of N-methyl-N-propyl-carbamoyl chloride (Intermediate AA). Ethyl (2S)-2-[[6-amino-9-benzyl-8-oxo-2-(propylsulfonimidoyl)purine-7-carbonyl]-methyl-amino]propanoate (34.1 mg, Example 17) was obtained as a yellow solid. $^1$H NMR (300 MHz, DMSO-d$_6$) δ ppm: 7.22-7.49 (m, 5H), 6.78 (br. s., 2H), 4.93-5.08 (m, 2H), 4.75 (br. s., 1H), 3.96-4.29 (m, 3H), 3.30-3.46 (m, 2H), 3.09 (s, 2H), 2.93 (br. s., 1H), 1.55-1.77 (m, 2H), 1.48 (d, J=7.16 Hz, 3H), 1.09-1.29 (m, 3H), 0.94 (t, J=7.44 Hz, 3H). MS obsd. (ESI$^+$) [(M+H)$^+$]: 504.2.

Example 18 tert-Butyl(2S)-2-[[6-amino-9-benzyl-8-oxo-2-(propylsulfonimidoyl)purine-7-carbonyl]-methyl-amino]-4-methyl-pentanoate

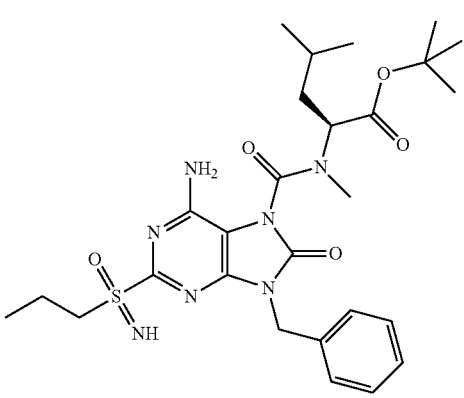

The title compound was prepared in analogy to Example 1, Method A, Step 6 by using tert-butyl (2S)-2-[chlorocarbonyl(methyl)amino]-4-methyl-pentanoate (Intermediate AT) instead of N-methyl-N-propyl-carbamoyl chloride (Intermediate AA). tert-Butyl (2S)-2-[[6-amino-9-benzyl-8-oxo-2-(propylsulfonimidoyl)purine-7-carbonyl]-methyl-amino]-4-methyl-pentanoate (22 mg, Example 18) was obtained as a white solid. $^1$H NMR (400 MHz, DMSO-d$_6$)

δ ppm: 7.42-7.27 (m, 5H), 6.78 (br. s., 2H), 5.05-4.96 (m, 2H), 4.78 (br. s., 1H), 4.33 (br. s., 1H), 3.51-3.37 (m, 2H), 3.01 (s, 3H), 1.75-1.54 (m, 4H), 1.44 (s, 8H), 1.33-1.11 (m, 2H), 0.99-0.82 (m, 9H). MS obsd. (ESI⁺) [(M+H)⁺]: 574.3.

Example 19

Isopropyl (2S)-2-[[6-amino-9-benzyl-8-oxo-2-(propylsulfonimidoyl)purine-7-carbonyl]-methyl-amino]-4-methyl-pentanoate

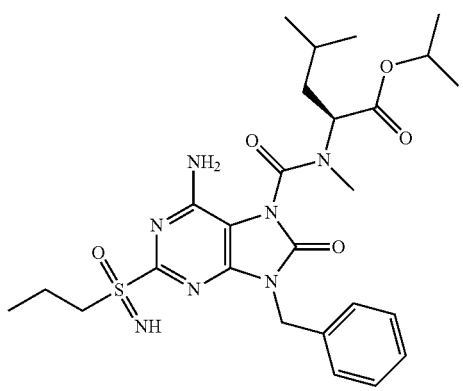

19

The title compound was prepared in analogy to Example 1, Method A, Step 6 by using isopropyl (2S)-2-[chlorocarbonyl(methyl)amino]-4-methyl-pentanoate (Intermediate AU) instead of N-methyl-N-propyl-carbamoyl chloride (Intermediate AA). Isopropyl (2S)-2-[[6-amino-9-benzyl-8-oxo-2-(propylsulfonimidoyl)purine-7-carbonyl]-methyl-amino]-4-methyl-pentanoate (43 mg, Example 19) was obtained as a white powder. ¹H NMR (400 MHz, DMSO-d₆) δ ppm: 7.43-7.27 (m, 5H), 6.75 (br. s., 2H), 5.05-4.94 (m, 3H), 4.88 (br. s., 1H), 4.19 (br. s., 1H), 3.43-3.34 (m, 2H), 3.01 (s, 3H), 1.91 (br. s., 1H), 1.77-1.56 (m, 4H), 1.25-1.16 (m, 6H), 0.99-0.83 (m, 9H). MS obsd. (ESI⁺) [(M+H)⁺]: 560.3.

Example 20

Ethyl(2S)-2-[[6-amino-9-benzyl-8-oxo-2-(propylsulfonimidoyl)purine-7-carbonyl]-methyl-amino]-3-methyl-butanoate

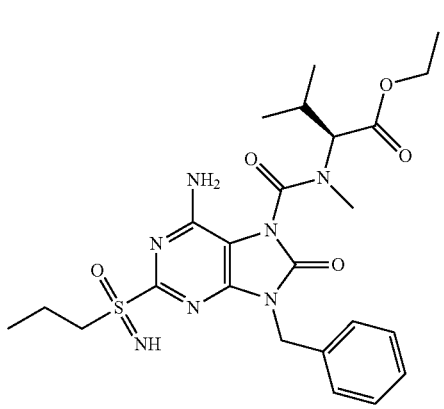

20

The title compound was prepared in analogy to Example 1, Method A, Step 6 by using ethyl (2S)-2-[chlorocarbonyl(methyl)amino]-3-methyl-butanoate (Intermediate AV) instead of N-methyl-N-propyl-carbamoyl chloride (Intermediate AA). Ethyl (2S)-2-[[6-amino-9-benzyl-8-oxo-2-(propylsulfonimidoyl)purine-7-carbonyl]-methyl-amino]-3-methyl-butanoate (51.5 mg, Example 20) was obtained as a white powder. ¹H NMR (400 MHz, DMSO-d₆) δ ppm: 7.23-7.51 (m, 5H), 6.76 (br. s., 2H), 5.01 (br. s., 2H), 4.42 (br. s., 1H), 3.97-4.26 (m, 3H), 3.34-3.45 (m, 2H), 3.12 (br. s., 3H), 2.24 (br. s., 1H), 1.65 (br. s., 2H), 1.13-1.29 (m, 3H), 0.88-1.10 (m, 9H). MS obsd. (ESI⁺) [M+H⁺]: 532.2.

Example 21

Ethyl(2S)-2-[[6-amino-9-benzyl-8-oxo-2-(propylsulfonimidoyl)purine-7-carbonyl]-methyl-amino]-4-methyl-pentanoate

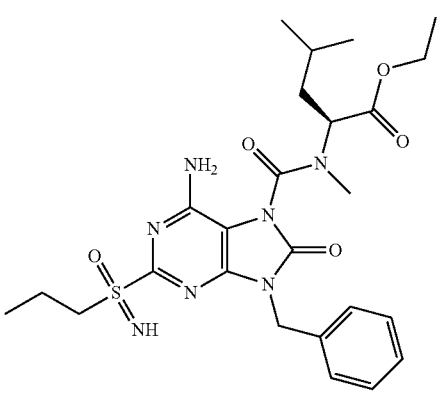

21

The title compound was prepared in analogy to Example 1, Method A, Step 6 by using ethyl (2S)-2-[chlorocarbonyl(methyl)amino]-4-methyl-pentanoate (Intermediate AW) instead of N-methyl-N-propyl-carbamoyl chloride (Intermediate AA). Ethyl (2S)-2-[[6-amino-9-benzyl-8-oxo-2-(propylsulfonimidoyl)purine-7-carbonyl]-methyl-amino]-4-methyl-pentanoate (17.3 mg, Example 21) was obtained as a white powder. ¹H NMR (400 MHz, DMSO-d₆) δ ppm: 7.26-7.45 (m, 5H), 6.73 (br. s., 2H), 4.91-5.09 (m, 3H), 4.06-4.25 (m, 3H), 3.34-3.45 (m, 2H), 3.04 (br. s., 3H), 1.93 (br. s., 1H), 1.54-1.78 (m, 4H), 1.22 (t, J=7.09 Hz, 3H), 0.77-1.01 (m, 9H). MS obsd. (ESI⁺) [(M+H)⁺]: 546.3.

Example 22

Ethyl(2S)-2-[[6-amino-9-benzyl-8-oxo-2-(propylsulfonimidoyl)purine-7-carbonyl]-methyl-amino]-3-phenyl-propanoate

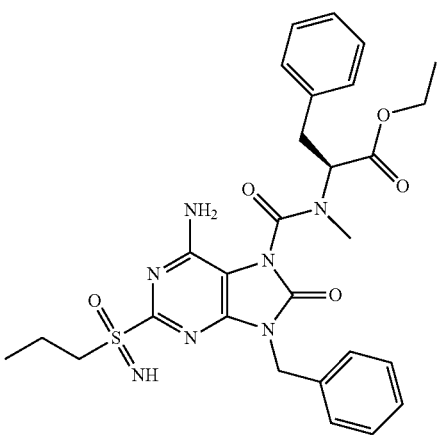

22

The title compound was prepared in analogy to Example 1, Method A, Step 6 by using ethyl (2S)-2-[chlorocarbonyl(methyl)amino]-3-phenyl-propanoate (Intermediate AX) instead of N-methyl-N-propyl-carbamoyl chloride (Intermediate AA). Ethyl (2S)-2-[[6-amino-9-benzyl-8-oxo-2-(propylsulfonimidoyl)purine-7-carbonyl]-methyl-amino]-3-phenyl-propanoate (30 mg, Example 22) was obtained as a white powder. $^1$H NMR (400 MHz, DMSO-$d_6$) δ ppm: 7.42-7.16 (m, 10H), 4.97 (s, 3H), 4.19 (q, J=7.1 Hz, 2H), 3.35-3.15 (m, 6H), 3.10-2.90 (m, 3H), 1.71-1.46 (m, 2H), 1.28-1.18 (m, 4H), 0.97-0.85 (m, 3H). MS obsd. (ESI$^+$) [(M+H)$^+$]: 580.

Example 23

Isopropyl(2S)-2-[[6-amino-9-benzyl-8-oxo-2-(propylsulfonimidoyl)purine-7-carbonyl]-methyl-amino]-3-phenyl-propanoate

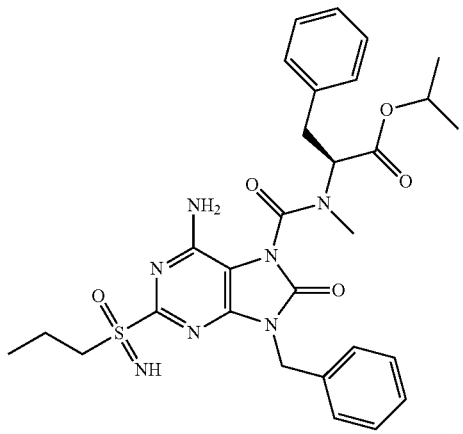

The title compound was prepared in analogy to Example 1, Method A, Step 6 by using isopropyl (2S)-2-[chlorocarbonyl(methyl)amino]-3-phenyl-propanoate (Intermediate AY) instead of N-methyl-N-propyl-carbamoyl chloride (Intermediate AA). Isopropyl (2S)-2-[[6-amino-9-benzyl-8-oxo-2-(propylsulfonimidoyl)purine-7-carbonyl]-methyl-amino]-3-phenyl-propanoate (22 mg, Example 23) was obtained as a white powder. $^1$H NMR (400 MHz, DMSO-$d_6$) δ ppm: 7.35-7.01 (m, 10H), 5.02-4.89 (m, 3H), 3.37-3.17 (m, 3H), 3.02-3.09 (m, 3H), 3.10-2.90 (m, 3H), 1.66-1.62 (m, 2H), 1.22-1.11 (m, 8H), 0.92 (t, J=7.4 Hz, 3H). MS obsd. (ESI$^+$) [(M+H)$^+$]: 594.

Example 24 tert-Butyl(2S)-2-[[6-amino-9-benzyl-8-oxo-2-(propylsulfonimidoyl)purine-7-carbonyl]-methyl-amino]-3-phenyl-propanoate

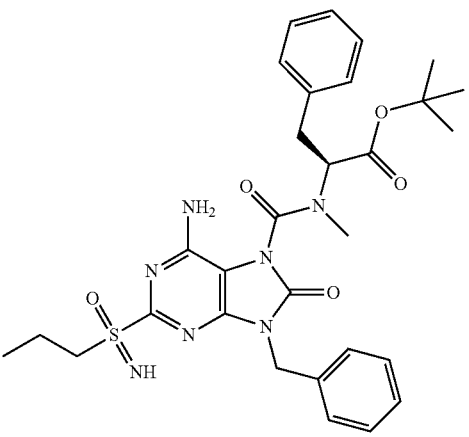

The title compound was prepared in analogy to Example 1, Method A, Step 6 by using tert-butyl (2S)-2-[chlorocarbonyl(methyl)amino]-3-phenyl-propanoate (Intermediate AZ) instead of N-methyl-N-propyl-carbamoyl chloride (Intermediate AA). tert-Butyl (2S)-2-[[6-amino-9-benzyl-8-oxo-2-(propylsulfonimidoyl)purine-7-carbonyl]-methyl-amino]-3-phenyl-propanoate (34 mg, Example 24) was obtained as a white powder. $^1$H NMR (400 MHz, DMSO-$d_6$) δ ppm: 7.42-7.16 (m, 10H), 5.03-4.90 (m, 3H), 3.68-3.24 (m, 5H), 3.24-3.09 (m, 2H), 3.01 (s, 3H), 1.68-1.57 (m, 2H), 1.43 (s, 9H), 0.99-0.85 (m, 3H). MS obsd. (ESI$^+$) [(M+H)$^+$]: 608.3.

Example 25

N-[2-[Acetyl(methyl)amino]ethyl]-6-amino-9-benzyl-N-methyl-8-oxo-2-(propylsulfonimidoyl)purine-7-carboxamide

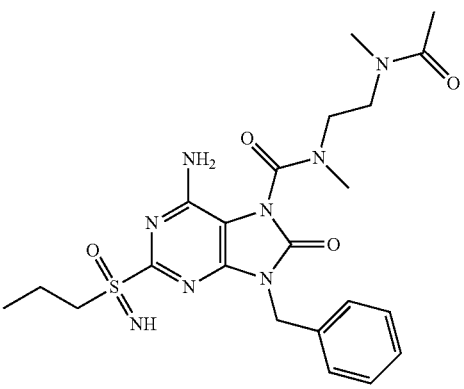

The title compound was prepared in analogy to Example 1, Method A, Step 6 by using N-[2-[acetyl(methyl)amino]ethyl]-N-methyl-carbamoyl chloride (Intermediate BA) instead of N-methyl-N-propyl-carbamoyl chloride (Intermediate AA). N-[2-[Acetyl(methyl)amino]ethyl]-6-amino-9-benzyl-N-methyl-8-oxo-2-(propylsulfonimidoyl)purine-7-carboxamide (26.1 mg, Example 25) was obtained as a white powder. $^1$H NMR (400 MHz, DMSO-$d_6$) δ ppm: 7.43-7.27 (m, 5H), 7.02 (br, 2H), 5.04-4.97 (m, 2H), 4.19-4.13 (m, 1H), 3.57 (d, J=5.5 Hz, 2H), 3.49-3.34 (m, 2H), 3.14 (s, 1H), 3.12-3.02 (m, 4H), 2.86 (d, J=7.5 Hz, 2H), 2.69-2.64 (m, 1H), 2.05 (s, 1H), 1.99 (s, 1H), 1.91-1.83 (m, 1H), 1.70-1.59 (m, 2H), 0.97-0.90 (m, 3H). MS obsd. (ESI$^+$) [(M+H)$^+$]: 503.2.

Example 26

Methyl N-[2-[[6-amino-9-benzyl-8-oxo-2-(propylsulfonimidoyl)purine-7-carbonyl]-methyl-amino]ethyl]-N-methyl-carbamate

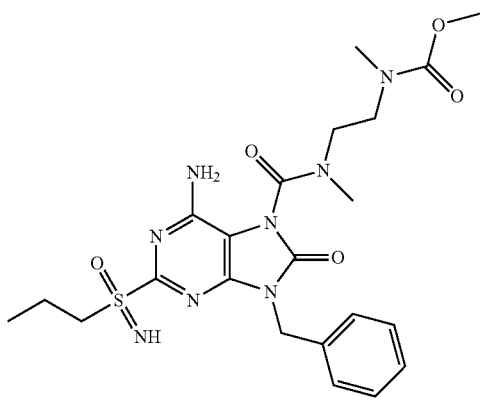

The title compound was prepared in analogy to Example 1, Method A, Step 6 by using methyl N-[2-[chlorocarbonyl(methyl)amino]ethyl]-N-methyl-carbamate (Intermediate BB) instead of N-methyl-N-propyl-carbamoyl chloride (Intermediate AA). Methyl N-[2-[[6-amino-9-benzyl-8-oxo-2-(propylsulfonimidoyl)purine-7-carbonyl]-methyl-amino]ethyl]-N-methyl-carbamate (65 mg, Example 26) was obtained as a yellow solid. $^1$H NMR (400 MHz, CDCl$_3$) δ ppm: 7.29-7.49 (m, 5H), 5.63-5.92 (m, 2H), 5.03-5.17 (m, 2H), 3.43-3.69 (m, 8H), 3.13-3.27 (m, 3H), 2.96-3.05 (m, 2H), 2.72 (br. s., 1H), 1.05 (t, J=7.40 Hz, 3H), 1.87 (dd, J=14.12, 6.96 Hz, 2H). MS obsd. (ESI) [(M+H)$^+$]: 519.2.

Example 27 tert-Butyl N-[2-[[6-amino-9-benzyl-8-oxo-2-(propylsulfonimidoyl)purine-7-carbonyl]-methyl-amino]ethyl]-N-methyl-carbamate

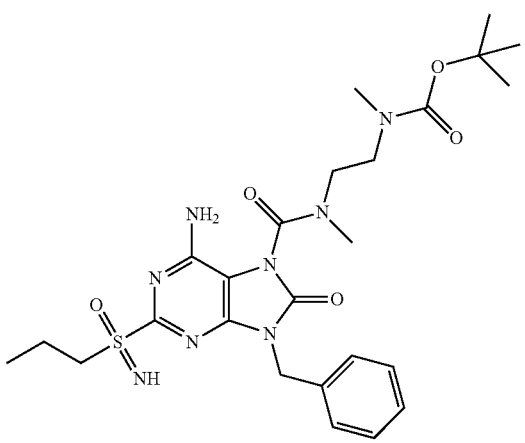

The title compound was prepared in analogy to Example 1, Method A, Step 6 by using tert-butyl N-[2-[chlorocarbonyl(methyl)amino]ethyl]-N-methyl-carbamate (Intermediate BC) instead of N-methyl-N-propyl-carbamoyl chloride (Intermediate AA). tert-Butyl N-[2-[[6-amino-9-benzyl-8-oxo-2-(propylsulfonimidoyl)purine-7-carbonyl]-methyl-amino]ethyl]-N-methyl-carbamate (32 mg, Example 27) was obtained as a white powder. $^1$H NMR (400 MHz, DMSO-d$_6$) δ ppm: 7.43-7.26 (m, 5H), 6.89 (br. s., 2H), 4.99 (d, J=5.0 Hz, 2H), 4.16 (s, 1H), 3.55 (br. s., 2H), 3.48-3.34 (m, 2H), 3.10 (s, 2H), 3.07 (s, 1H), 2.86 (d, J=12.8 Hz, 2H), 2.74 (d, J=9.5 Hz, 1H), 2.70-2.60 (m, 1H), 1.72-1.54 (m, 2H), 1.39 (s, 6H), 1.23 (s, 2H), 1.13 (s, 2H), 0.93 (t, J=7.4 Hz, 3H). MS obsd. (ESI$^+$) [(M+H)$^+$]: 562.

Example 28

Ethyl N-[2-[[6-amino-9-benzyl-8-oxo-2-(propylsulfonimidoyl)purine-7-carbonyl]-methyl-amino]ethyl]-N-methyl-carbamate

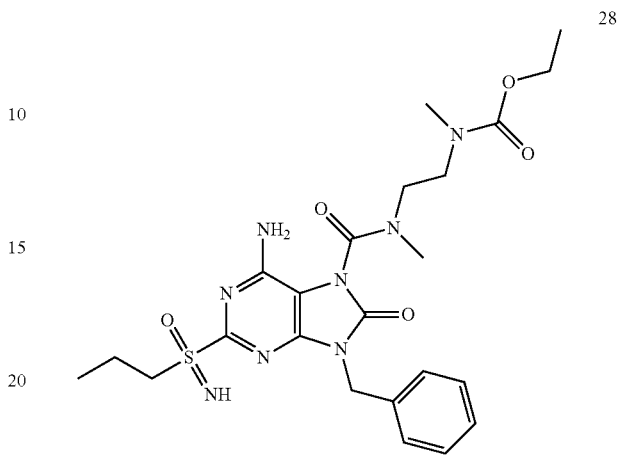

The title compound was prepared in analogy to Example 1, Method A, Step 6 by using ethyl N-[2-[chlorocarbonyl(methyl)amino]ethyl]-N-methyl-carbamate (Intermediate BD) instead of N-methyl-N-propyl-carbamoyl chloride (Intermediate AA). Ethyl N-[2-[[6-amino-9-benzyl-8-oxo-2-(propylsulfonimidoyl)purine-7-carbonyl]-methyl-amino]ethyl]-N-methyl-carbamate (87 mg, Example 28) was obtained as a yellow solid. $^1$H NMR (400 MHz, CDCl$_3$) δ ppm: 7.29-7.53 (m, 5H), 5.65-5.90 (m, 2H), 5.02-5.14 (m, 2H), 3.38-4.21 (m, 9H), 3.14-3.26 (m, 3H), 3.00 (br. s., 2H), 2.73 (s, 1H), 1.76-1.99 (m, 2H), 1.22-1.31 (m, 3H), 1.05 (s, 3H). MS obsd. (ESI$^+$) [(M+H)$^+$]: 533.2.

Example 29

2-[[6-Amino-9-benzyl-8-oxo-2-(propylsulfonimidoyl)purine-7-carbonyl]-methyl-amino]ethyl N-butyl-N-methyl-carbamate

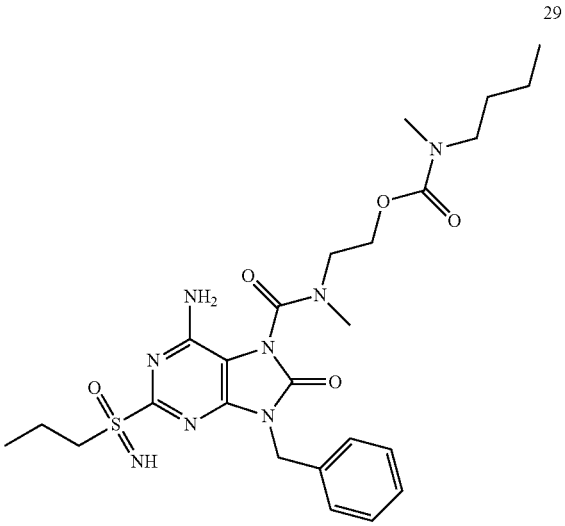 [SMILES: CCCCN(C)C(=O)OCCN(C)C(=O)n1c(=O)n(Cc2ccccc2)c2nc(S(=N)(=O)CCC)nc(N)c21]

The title compound was prepared in analogy to Example 1, Method A, Step 6 by using 2-[chlorocarbonyl(methyl)amino]ethyl N-butyl-N-methyl-carbamate (Intermediate BE) instead of N-methyl-N-propyl-carbamoyl chloride (Intermediate AA). 2-[[6-Amino-9-benzyl-8-oxo-2-(propylsulfonimidoyl)purine-7-carbonyl]-methyl-amino]ethyl N-butyl-N-methyl-carbamate (19 mg, Compound 29) was obtained as yellow solid. $^1$H NMR (400 MHz, DMSO-d$_6$) δ ppm: 7.25-7.48 (m, 5H), 6.96 (br. s., 2H), 4.99 (s, 2H), 4.06-4.36 (m, 3H), 3.59-3.83 (m, 1H), 3.33-3.49 (m, 3H), 3.07-3.21 (m, 4H), 2.79 (s, 2H), 1.65 (br. s., 2H), 1.05-1.47 (m, 6H), 0.93 (t, J=7.40 Hz, 3H), 0.70-0.87 (m, 3H). MS obsd. (ESI$^+$) [(M+H)$^+$]: 561.2.

Example 30

2-[[6-Amino-9-benzyl-8-oxo-2-(propylsulfonimidoyl)purine-7-carbonyl]-methyl-amino]ethyl pyrrolidine-1-carboxylate

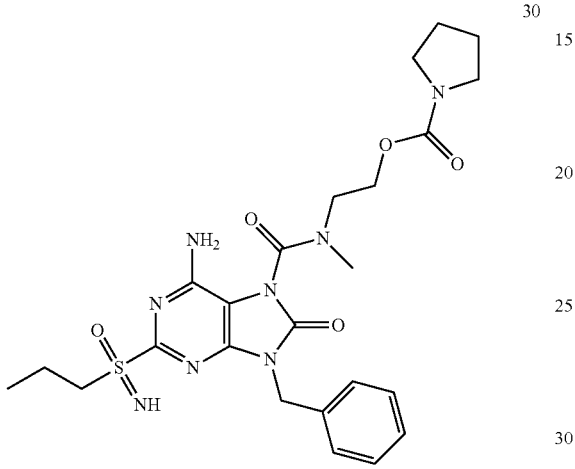

The title compound was prepared in analogy to Example 1, Method A, Step 6 by using 2-[chlorocarbonyl(methyl)amino]ethyl pyrrolidine-1-carboxylate (Intermediate BF) instead of N-methyl-N-propyl-carbamoyl chloride (Intermediate AA). 2-[[6-Amino-9-benzyl-8-oxo-2-(propylsulfonimidoyl)purine-7-carbonyl]ethyl-amino]ethyl pyrrolidine-1-carboxylate (10.0 mg, Example 30) was obtained as a yellow solid. $^1$H NMR (400 MHz, DMSO-d$_6$) δ ppm: 7.26-7.41 (m, 5H), 6.96 (br.s., 2H), 4.99 (s, 2H), 4.01-4.35 (m, 4H), 3.29-3.47 (m, 3H), 3.23 (br. s., 3H), 3.03-3.17 (m, 4H), 1.52-1.84 (m, 6H), 0.90-0.96 (m, 3H). MS obsd. (ESI$^+$) [(M+H)$^+$]: 545.2.

Example 31

2-[[6-Amino-9-benzyl-8-oxo-2-(propylsulfonimidoyl)purine-7-carbonyl]-methyl-amino]ethyl N-methyl-N-propyl-carbamate

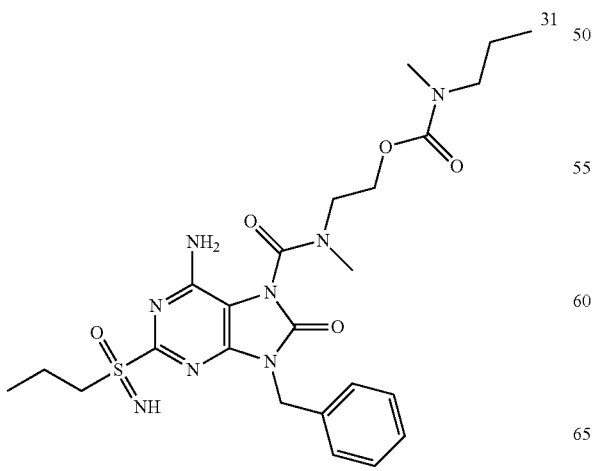

The title compound was prepared in analogy to Example 1, Method A, Step 6 by using 2-[chlorocarbonyl(methyl)amino]ethyl N-methyl-N-propyl-carbamate (Intermediate BG) instead of N-methyl-N-propyl-carbamoyl chloride (Intermediate AA). 2-[[6-Amino-9-benzyl-8-oxo-2-(propylsulfonimidoyl)purine-7-carbonyl]-methyl-amino]ethyl N-methyl-N-propyl-carbamate (3.7 mg, Example 31) was obtained as a yellow solid. $^1$H NMR (400 MHz, CD$_3$OD) δ ppm: 7.22-7.48 (m, 5H), 5.09-5.22 (m, 4H), 4.55 (s, 2H), 3.38-3.57 (m, 4H), 3.13 (s, 3H), 1.61-1.85 (m, 4H), 1.22-1.41 (m, 3H), 0.88-1.13 (m, 6H). MS obsd. (ESI$^+$) [(M+H)$^+$]: 547.2.

Example 32

2-[[6-Amino-9-benzyl-8-oxo-2-(propylsulfonimidoyl)purine-7-carbonyl]-methyl-amino]ethyl N,N-diethylcarbamate

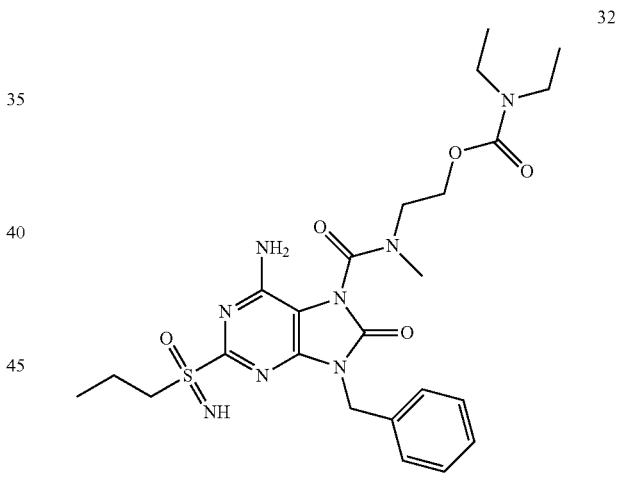

The title compound was prepared in analogy to Example 1, Method A, Step 6 by using 2-[chlorocarbonyl(methyl)amino]ethyl N,N-diethylcarbamate (Intermediate BH) instead of N-methyl-N-propyl-carbamoyl chloride (Intermediate AA). 2-[[6-Amino-9-benzyl-8-oxo-2-(propylsulfonimidoyl)purine-7-carbonyl]-methyl-amino]ethyl N,N-diethylcarbamate (21.7 mg, Example 32) was obtained as yellow solid. $^1$H NMR (400 MHz, DMSO-d$_6$) δ ppm: 7.25-7.41 (m, 5H), 6.96 (br. s., 2H), 4.99 (s, 2H), 4.08-4.36 (m, 3H), 3.70 (br, 1H), 3.33-3.46 (m, 3H), 3.01-3.24 (m, 7H), 1.55-1.74 (m, 2H), 0.86-1.05 (m, 9H). MS obsd. (ESI$^+$) [(M+H)$^+$]: 547.2.

Example 33

2-[[6-Amino-9-benzyl-8-oxo-2-(propylsulfonimidoyl)purine-7-carbonyl]-methyl-amino]ethyl ethyl carbonate

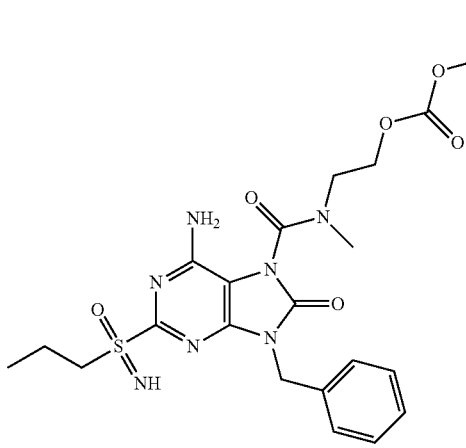

The title compound was prepared in analogy to Example 1, Method A, Step 6 by using 2-[chlorocarbonyl(methyl)amino]ethyl ethyl carbonate (Intermediate BI) instead of N-methyl-N-propyl-carbamoyl chloride (Intermediate AA). 2-[[6-Amino-9-benzyl-8-oxo-2-(propylsulfonimidoyl)purine-7-carbonyl]-methyl-amino]ethyl ethyl carbonate (46 mg, Example 33) was obtained as yellow solid. $^1$H NMR (400 MHz, DMSO-$d_6$) δ ppm: 0.82-0.99 (m, 3H), 1.02-1.28 (m, 3H), 1.56-1.76 (m, 2H), 3.05-3.18 (m, 3H), 3.35-3.48 (m, 3H), 3.73 (t, J=5.08 Hz, 2H), 4.08-4.27 (m, 3H), 4.37 (br. s., 1H), 5.00 (s, 2H), 6.76-7.11 (m, 2H), 7.22-7.45 (m, 5H). MS obsd. (ESI) [(M+H)$^+$]: 520.

Example 34-A and Example 34-B

6-Amino-N-butyl-9-[(4-chlorophenyl)methyl]-N-methyl-8-oxo-2-[S(S)-propylsulfonimidoyl]purine-7-carboxamide and 6-amino-N-butyl-9-[(4-chlorophenyl)methyl]-N-methyl-8-oxo-2-[S(S)-propylsulfonimidoyl]purine-7-carboxamide

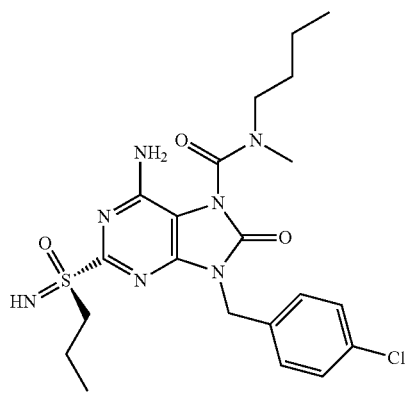

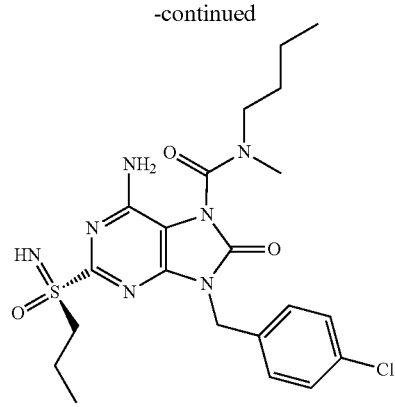

Step 1: Preparation of 4-amino-3-[(4-chlorophenyl)methyl]-2-oxo-1H-imidazole-5-carbonitrile (Compound 34a)

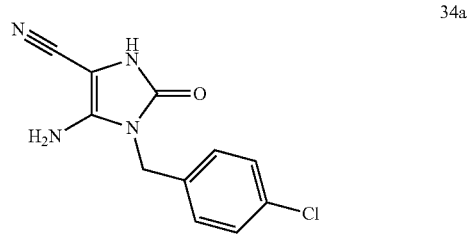

Compound 34a was prepared in analogy to Example 1, Method A, Step 1 by using 4-chlorobenzyl isocyanate instead of benzyl isocyanate. 4-Amino-3-[(4-chlorophenyl)methyl]-2-oxo-1H-imidazole-5-carbonitrile (8.0 g, Compound 34a) was obtained as a yellow solid. MS obsd. (ESI$^+$) [(M+H)$^+$]: 249.

Step 2: Preparation of 6-amino-9-[(4-chlorophenyl)methyl]-2-sulfanyl-7H-purin-8-one (Compound 34b)

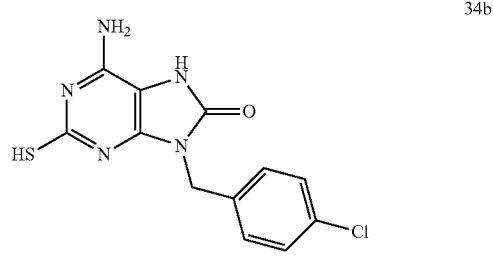

Compound 34b was prepared in analogy to Example 1, Method A, Step 2 by using 4-Amino-3-[(4-chlorophenyl)methyl]-2-oxo-1H-imidazole-5-carbonitrile (Compound 34a) instead of 4-amino-3-phenylmethyl-2-oxo-1H-imidazole-5-carbonitrile (Compound 1a). 6-Amino-9-[(4-chlorophenyl)methyl]-2-sulfanyl-7H-purin-8-one (6.4 g, Compound 34b) was obtained as a yellow solid and was used for the next step without further purification. MS obsd. (ESI$^+$) [(M+H)$^+$]: 308.

Step 3: Preparation of 6-amino-9-[(4-chlorophenyl)methyl]-2-propylsulfanyl-7H-purin-8-one (Compound 34c)

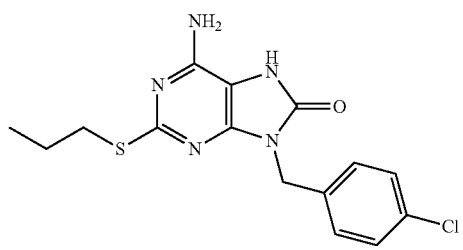

34c

Compound 34c was prepared in analogy to Example 1, Method A, Step 3 by using 6-amino-9-[(4-chlorophenyl)methyl]-2-sulfanyl-7H-purin-8-one (Compound 34b) instead of 6-amino-9-phenylmethyl-2-sulfanyl-7H-purin-8-one (Compound 1b). 6-Amino-9-[(4-chlorophenyl)methyl]-2-propylsulfanyl-7H-purin-8-one (800 mg, Compound 34c) was obtained as a white solid. MS obsd. (ESI$^+$) [(M+H)$^+$]: 350.

Step 4: Preparation of 6-amino-9-[(4-chlorophenyl)methyl]-2-propylsulfinyl-7H-purin-8-one (Compound 34d)

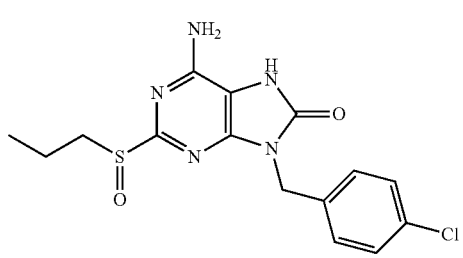

34d

Compound 34d was prepared in analogy to Example 1, Method A, Step 4 by using 6-amino-9-[(4-chlorophenyl)methyl]-2-propylsulfanyl-7H-purin-8-one (Compound 34c) instead of 6-amino-9-benzyl-2-propylsulfanyl-7H-purin-8-one (Compound 1c). 6-Amino-9-[(4-chlorophenyl)methyl]-2-propylsulfinyl-7H-purin-8-one (150 mg, Compound 34d) was obtained as a white solid. MS obsd. (ESI$^+$) [(M+H)$^+$]: 366.

Step 5: Preparation of 6-amino-9-[(4-chlorophenyl)methyl]-2-(propylsulfonimidoyl)-7H-purin-8-one (compound 34e), 6-amino-9-[(4-chlorophenyl)methyl]-2-[S(S)-propylsulfonimidoyl]-7H-purin-8-one and 6-amino-9-[(4-chlorophenyl)methyl]-2-[S(S)-propylsulfonimidoyl]-7H-purin-8-one (Compound 34e-A and Compound 34e-B)

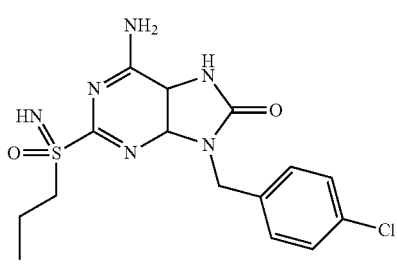

34e

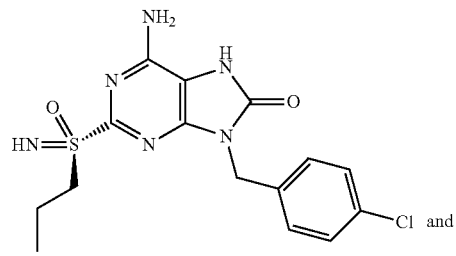

34e-A and

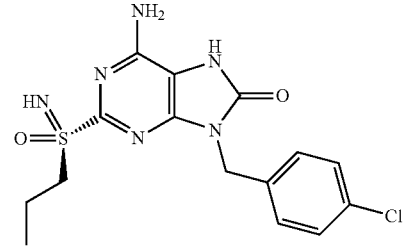

34e-B

Compound 34e was prepared in analogy to Example 1, Method A, Step 5 by using 6-amino-9-[(4-chlorophenyl)methyl]-2-propylsulfinyl-7H-purin-8-one (Compound 34d) instead of 6-amino-9-benzyl-2-(2-propylsulfinyl)-7H-purin-8-one (Compound 1d). 6-Amino-9-[(4-chlorophenyl)methyl]-2-(propylsulfonimidoyl)-7H-purin-8-one (250 mg, compound 34e) was obtained as a white solid. $^1$H NMR (400 MHz, DMSO-d$_6$) δ ppm: 10.60 (br. s, 1H), 7.32-7.42 (m, 4H), 6.98 (br. s, 2H), 4.96 (s, 2H), 4.03 (s, 1H), 3.25-3.41 (m, 2H), 1.56-1.68 (m, 2H), 0.91 (t, J=8 Hz, 3H). MS obsd. (ESI$^+$) [(M$^+$H)$^+$]: 381.

Separation of compound of Compound 34e by chiral HPLC afforded Compound 34e-A (faster eluting, 110 mg) and Compound 34e-B (slower eluting, 100 mg) as white solid with methanol 5%-40% (0.05% DEA)/CO$_2$ on ChiralPak OJ-3 column.

Compound 34e-A: $^1$H NMR (400 MHz, DMSO-d$_6$) δ ppm: 10.63 (br. s, 1H), 7.33-7.42 (m, 4H), 6.99 (br. s, 2H), 4.96 (s, 2H), 4.05 (br. s, 1H), 3.26-3.39 (m, 2H), 1.53-1.69 (m, 2H), 0.91 (t, J=7.4 Hz, 3H). MS obsd. (ESI$^+$) [(M$^+$H)$^+$]: 381.

Compound 34e-B: $^1$H NMR (400 MHz, DMSO-d$_6$) δ ppm: 10.63 (br. s, 1H), 7.33-7.42 (m, 4H), 6.99 (br. s, 2H), 4.96 (s, 2H), 4.05 (br. s, 1H), 3.26-3.40 (m, 2H), 1.54-1.69 (m, 2H), 0.91 (t, J=7.5 Hz, 3H). MS obsd. (ESI$^+$) [(M$^+$H)$^+$]: 381.

Step 6: 6-Amino-N-butyl-9-[(4-chlorophenyl)methyl]-N-methyl-8-oxo-2-[S(S)-propylsulfonimidoyl]purine-7-carboxamide and 6-amino-N-butyl-9-[(4-chlorophenyl)methyl]-N-methyl-8-oxo-2-[S(S)-propylsulfonimidoyl]purine-7-carboxamide (Example 34-A and Example 34-B)

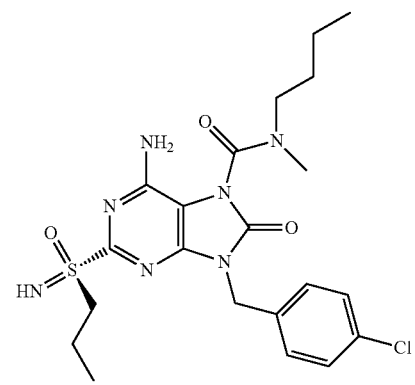

-continued

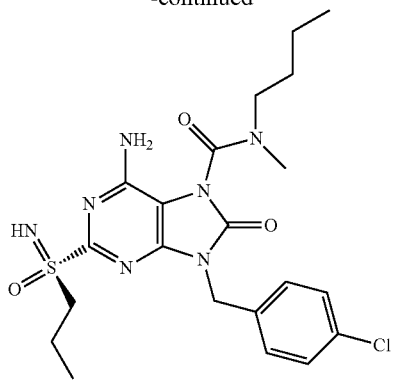

Example 34-A was prepared in analogy to Example 1, Method A, Step 6 by using Compound 34e-A and N-butyl-N-methyl-carbamoyl chloride instead of 6-amino-9-benzyl-2-(propylsulfonimidoyl)-7H-purin-8-one (Compound 1e) and N-methyl-N-propyl-carbamoyl chloride (Intermediate AA).

Example 34-A (160 mg): $^1$H NMR (400 MHz, DMSO-$d_6$) δ ppm: 7.37-7.45 (m, 4H), 6.91 (br. s., 2H), 4.99 (s, 2H), 4.17 (s, 1H), 3.28-3.40 (m, 4H), 3.05 (s, 2H), 3.02 (s, 1H), 1.49-1.70 (m, 4H), 1.15-1.37 (m, 2H), 0.89-0.94 (m, 5H), 0.76 (t, J=8 Hz, 1H). MS obsd. (ESI$^+$) [(M+H)$^+$]: 494.

Example 34-B (167 mg) was prepared in analogy to Example 34-A by using Compound 34e-B instead of Compound 34e-A.

Example 34-B: $^1$H NMR (400 MHz, DMSO-$d_6$) δ ppm: 7.36-7.45 (m, 4H), 6.91 (br. s., 2H), 4.99 (s, 2H), 4.17 (s, 1H), 3.28-3.41 (m, 4H), 3.05 (s, 2H), 3.02 (s, 1H), 1.50-1.71 (m, 4H), 1.15-1.37 (m, 2H), 0.89-0.94 (m, 5H), 0.76 (t, J=7.4 Hz, 1H). MS obsd. (ESI$^+$) [(M+H)$^+$]: 494.

Example 35

6-Amino-9-[(4-chlorophenyl)methyl]-N-ethyl-N-methyl-8-oxo-2-(propylsulfonimidoyl)purine-7-carboxamide

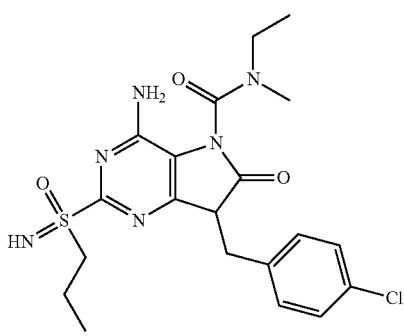

The title compound was prepared in analogy to Example 1, Method A, Step 6 by using 6-amino-9-[(4-chlorophenyl)methyl]-2-(propylsulfonimidoyl)-7H-purin-8-one (Compound 34e) and N-ethyl-N-methyl-carbamoyl chloride instead of 6-amino-9-benzyl-2-(propylsulfonimidoyl)-7H-purin-8-one (Compound 1e) and N-methyl-N-propyl-carbamoyl chloride (Intermediate AA). 6-Amino-9-[(4-chlorophenyl)methyl]-N-ethyl-N-methyl-8-oxo-2-(propylsulfonimidoyl)purine-7-carboxamide (60 mg, Example 35) was obtained as a white solid. $^1$H NMR (400 MHz, DMSO-$d_6$) δ ppm: 7.40 (s, 4H), 6.91 (br s, 2H), 4.99 (s, 2H), 4.16 (s, 1H), 3.34-3.44 (m, 4H), 3.05 (s, 2H), 3.01 (s, 1H), 1.58-1.67 (m, 2H), 1.18 (t, J=8.0 Hz, 3H), 0.92 (t, J=8.0 Hz, 3H). MS obsd. (ESI$^+$) [(M+H)$^+$]: 466.

Example 36-A and Example 36-B

6-Amino-N-methyl-8-oxo-N-propyl-2[S(S)-propylsulfonimidoyl]-9-(p-tolylmethyl)purine-7-carboxamide and 6-amino-N-methyl-8-oxo-N-propyl-2[S(R)-propylsulfonimidoyl]-9-(p-tolylmethyl)purine-7-carboxamide

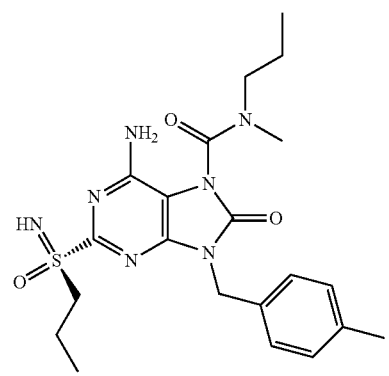

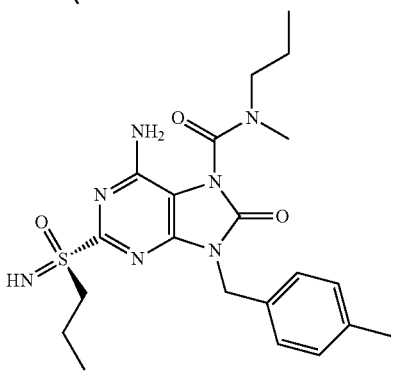

Step 1: Preparation of 6-chloro-5-nitro-2-propylsulfanyl-N-(p-tolylmethyl)pyrimidin-4-amine (Compound 36a)

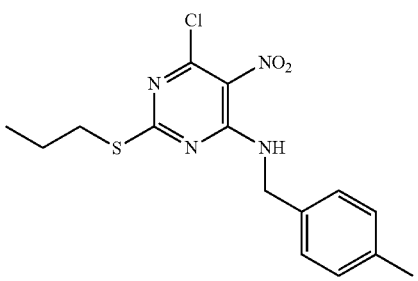

Compound 36a was prepared in analogy to Example 1, Method B, Step 1 by using p-tolylmethylamine instead of phenylmethanamine. 6-Chloro-5-nitro-2-propylsulfanyl-N-(p-tolylmethyl)pyrimidin-4-amine (3.9 g, Compound 36a) was obtained as a white solid. MS obsd. (ESI$^+$) [(M+H)$^+$]: 353.

Step 2: Preparation of 6-chloro-2-propylsulfanyl-N4-(p-tolylmethyl)pyrimidine-4,5-diamine (Compound 36b)

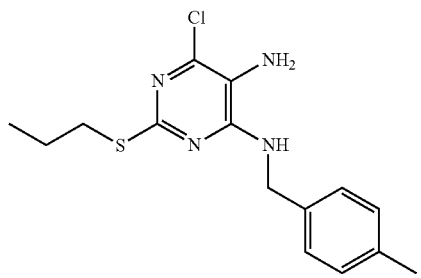

Compound 36b was prepared in analogy to Example 1, Method B, Step 2 by using 6-chloro-5-nitro-2-propylsulfanyl-N-(p-tolylmethyl)pyrimidin-4-amine (Compound 36a) instead of N-benzyl-6-chloro-5-nitro-2-propylsulfanyl-pyrimidin-4-amine (Compound 1f). 6-Chloro-2-propylsulfanyl-N4-(p-tolylmethyl)pyrimidine-4,5-diamine (2.2 g, Compound 36b) was obtained as a white solid. MS obsd. (ESI⁺) [(M+H)⁺]: 323.

Step 3: Preparation of 6-chloro-2-propylsulfanyl-9-(p-tolylmethyl)-7H-purin-8-one (Compound 36c)

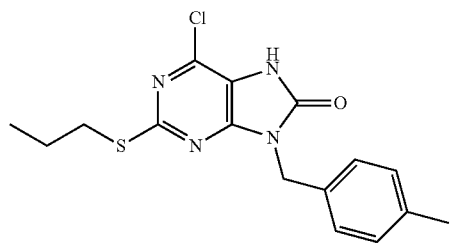

Compound 36c was prepared in analogy to Example 1, Method B, Step 3 by using 6-chloro-2-propylsulfanyl-N4-(p-tolylmethyl)pyrimidine-4,5-diamine (Compound 36b) instead of N-benzyl-6-chloro-2-(propylsulfanyl)pyrimidine-4,5-diamine (Compound 1g). 6-Chloro-2-propylsulfanyl-9-(p-tolylmethyl)-7H-purin-8-one (2.2 g, Compound 36c) was obtained as a white solid. MS obsd. (ESI⁺) [(M+H)⁺]: 349.

Step 4: Preparation of 6-[(4-methoxyphenyl)methylamino]-2-propylsulfanyl-9-(p-tolylmethyl)-7H-purin-8-one (Compound 36d)

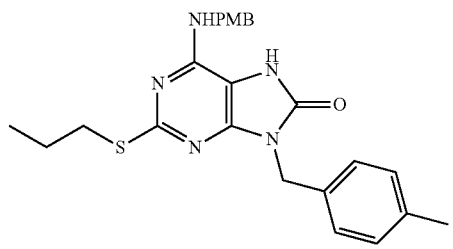

Compound 36d was prepared in analogy to Example 1, Method B, Step 4, by using 6-chloro-2-propylsulfanyl-9-(p-tolylmethyl)-7H-purin-8-one (Compound 36c) instead of 9-benzyl-6-chloro-2-propylsulfanyl-7H-purin-8-one (Compound 1h). 6-[(4-methoxyphenyl)methylamino]-2-propylsulfanyl-9-(p-tolylmethyl)-7H-purin-8-one (2.0 g, Compound 36d) was obtained as a white solid. MS obsd. (ESI⁺) [(M+H)⁺]: 450.

Step 5: Preparation of 6-amino-2-propylsulfanyl-9-(p-tolylmethyl)-7H-purin-8-one (Compound 36e)

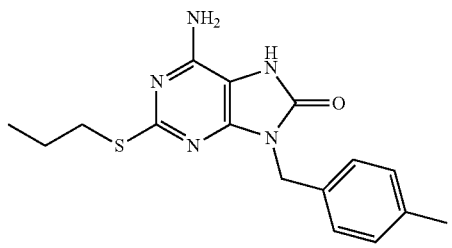

Compound 36e was prepared in analogy to Example 1, Method B, Step 5 by using 6-[(4-methoxyphenyl)methylamino]-2-propylsulfanyl-9-(p-tolylmethyl)-7H-purin-8-one (Compound 36d) instead of 6-amino-9-benzyl-2-propylsulfanyl-7H-purin-8-one (Compound 1i). 6-amino-2-propylsulfanyl-9-(p-tolylmethyl)-7H-purin-8-one (1.0 g, Compound 36e) was obtained as a white solid. MS obsd. (ESI⁺) [(M+H)⁺]: 330.

Step 6: Preparation of 6-amino-2-propylsulfinyl-9-(p-tolylmethyl)-7H-purin-8-one (Compound 36f)

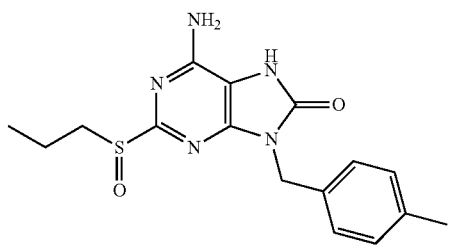

Compound 36f was prepared in analogy to Example 1, Method B, Step 6 by using 6-amino-2-propylsulfanyl-9-(p-tolylmethyl)-7H-purin-8-one (Compound 36e) instead of 6-amino-9-benzyl-2-(2-propylsulfanyl)-7H-purin-8-one (Compound 1c). 6-amino-2-propylsulfinyl-9-(p-tolylmethyl)-7H-purin-8-one (220 mg, Compound 36O was obtained as a white solid MS obsd. (ESI⁺) [(M+H)⁺]: 345.

Step 7: Preparation of 6-amino-2-(propylsulfonimidoyl)-9-(p-tolylmethyl)-7H-purin-8-one (Compound 36g)

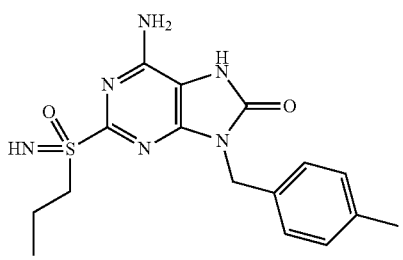

Compound 36g was prepared in analogy to Example 1, Method B, Step 7 by using 6-amino-2-propylsulfinyl-9-(p-tolylmethyl)-7H-purin-8-one (Compound 36f) instead of 6-amino-9-benzyl-2-propylsulfinyl-7H-purin-8-one (Compound 1d). 6-Amino-2-(propylsulfonimidoyl)-9-(p-tolylmethyl)-7H-purin-8-one (127 mg, Compound 36g) was obtained as a white solid. ¹H NMR (400 MHz, DMSO-d₆) δ ppm: 10.67 (br. s., 1H), 7.23 (d, J=8.0 Hz, 2H), 7.13 (d, J=8.0 Hz, 2H), 6.98 (br. s., 2H), 4.91 (s, 2H), 4.05 (s, 1H), 3.34-3.27 (m, 2H), 2.26 (s, 3H), 1.67-1.62 (m, 2H), 0.92 (t, J=8.0 Hz, 3H). MS obsd. (ESI⁺) [(M+H)⁺]: 361.

Separation of compound 36g by chiral HPLC afforded compound 36g-A (faster eluting, 50 mg) and compound 36g-B (slower eluting, 49 mg) as white solid with 30% isopropanol (0.05% DEA)/CO₂ on ChiralPak AD-3 column.

Compound 36g-A: ¹H NMR: (400 MHz, DMSO-d₆) δ ppm: 10.51 (s, 1H), 7.22 (d, J=8.0 Hz, 2H), 7.12 (d, J=8.0 Hz, 2H), 7.00 (s, 2H), 4.91 (s, 2H), 4.03 (s, 1H), 3.35-3.31 (m, 2H), 2.26 (s, 3H), 1.70-1.58 (m, 2H), 0.93 (t, J=7.40 Hz, 3H). MS obsd. (ESI⁺) [(M+H)⁺]: 361.

Compound 36g-B: ¹H NMR: (400 MHz, DMSO-d₆) δ ppm: 10.54 (s, 1H), 7.23 (d, J=8.0 Hz, 2H), 7.13 (d, J=8.0 Hz, 2H), 6.97 (s, 2H), 4.91 (s, 2H), 4.04 (s, 1H), 3.34-3.30 (m, 2H), 2.26 (s, 3H), 1.72-1.57 (m, 2H), 0.93 (t, J=7.40 Hz, 3H). MS obsd. (ESI⁺) [(M+H)⁺]: 361.

Step 8: Preparation of 6-Amino-N-methyl-8-oxo-N-propyl-2[S(S)-propylsulfonimidoyl]-9-(p-tolylmethyl)purine-7-carboxamide and 6-amino-N-methyl-8-oxo-N-propyl-2[S(R)-propylsulfonimidoyl]-9-(p-tolylmethyl)purine-7-carboxamide (Example 36-A and Example 36-B)

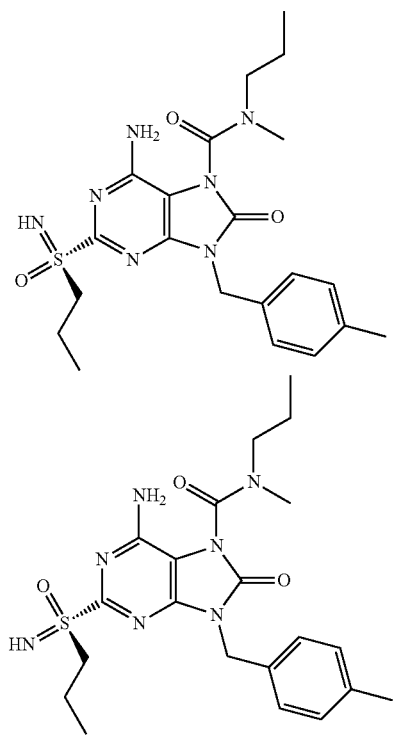

Example 36-A was prepared in analogy to Example 1, Method A, Step 6 by using Compound 36g-A instead of 6-amino-9-benzyl-2-(propylsulfonimidoyl)-7H-purin-8-one (Compound 1e). Example 36-A (108 mg) was obtained as a white solid. ¹H NMR (400 MHz, DMSO-d₆) δ ppm: 7.27 (d, J=8 Hz, 2H), 7.14 (d, J=8 Hz, 2H), 6.87 (br. s., 2H), 4.95 (s, 2H), 4.15 (s, 1H), 3.33-3.57 (m, 4H), 3.05 (s, 2H), 3.02 (s, 1H), 2.26 (s, 3H), 1.52-1.73 (m, 4H), 0.75-0.97 (m, 6H). MS obsd. (ESI⁺) [(M+H)⁺]: 460.

Example 36-B was prepared in analogy to Example 1, Method A, Step 6 by using Compound 36g-B instead of 6-amino-9-benzyl-2-(propylsulfonimidoyl)-7H-purin-8-one (compound 1e). Example 36-B (125 mg): ¹H NMR (400 MHz, DMSO-d₆) δ ppm: 7.27 (d, J=8 Hz, 2H), 7.14 (d, J=8 Hz, 2H), 6.87 (br. s., 2H), 4.95 (s, 2H), 4.15 (s, 1H), 3.33-3.57 (m, 4H), 3.05 (s, 2H), 3.02 (s, 1H), 2.26 (s, 3H), 1.52-1.73 (m, 4H), 0.75-0.97 (m, 5H). MS obsd. (ESI⁺) [(M+H)⁺]: 460.

Example 37-A and Example 37-B

6-Amino-2-[S(S)-propylsulfonimidoyl]-9-(p-tolylmethyl)-7-(pyrrolidine-1-carbonyl)purin-8-one and 6-amino-2-[S(R)-propylsulfonimidoyl]-9-(p-tolylmethyl)-7-(pyrrolidine-1-carbonyl)purin-8-one

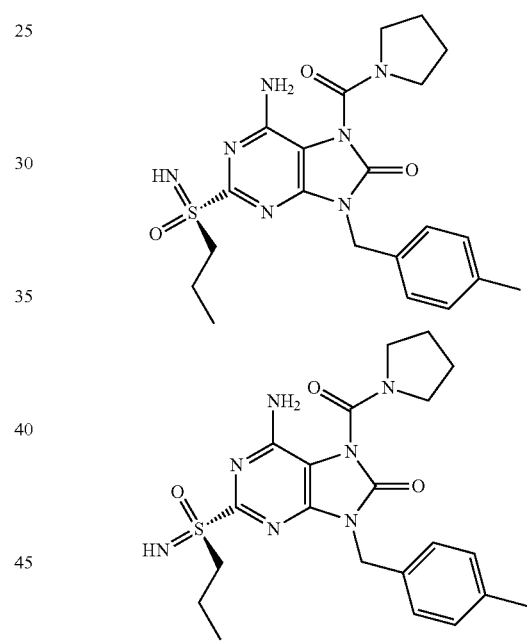

Example 37-A was prepared in analogy to Example 1, Method A, Step 6 by using Compound 36g-A and pyrrolidine-1-carbonyl chloride instead of 6-amino-9-benzyl-2-(propylsulfonimidoyl)-7H-purin-8-one (Compound 1e) and N-methyl-N-propyl-carbamoyl chloride (Intermediate AA).

Example 37-A (390 mg) was obtained as a white solid. ¹H NMR (400 MHz, DMSO-d₆) δ ppm: 7.31-7.11 (m, 4H), 7.04 (s, 2H), 4.95 (s, 2H), 4.15 (s, 1H), 3.65-3.47 (m, 4H), 3.37 (m, 2H), 2.27 (s, 3H), 1.97-1.81 (m, 4H), 1.71-1.59 (m, 2H), 0.94 (t, J=7.4 Hz, 3H). MS obsd. (ESI⁺) [(M+H)⁺]: 458.2.

Example 37-B (125 mg) was prepared in analogy to Example 37-A by using Compound 36g-B instead of Compound 36g-A. ¹H NMR (400 MHz, DMSO-d₆) δ ppm: 7.28-7.14 (m, 4H), 7.04 (s, 2H), 4.95 (s, 2H), 4.15 (s, 1H), 3.65-3.47 (m, 4H), 3.37 (m, 2H), 2.27 (s, 3H), 1.93-1.84 (m, 4H), 1.65-1.60 (m, 2H), 0.95 (t, J=7.4 Hz, 3H). MS obsd. (ESI⁺) [(M+H)⁺]: 458.3.

Example 38-A and Example 38-B

6-Amino-N-(2-methoxyethyl)-N-methyl-8-oxo-2-[S(S)-propylsulfonimidoyl]-(p-tolylmethyl)purine-7-carboxamide and 6-amino-N-(2-methoxyethyl)-N-methyl-8-oxo-2-[S(R)-propylsulfonimidoyl]-9-(p-tolylmethyl)purine-7-carboxamide

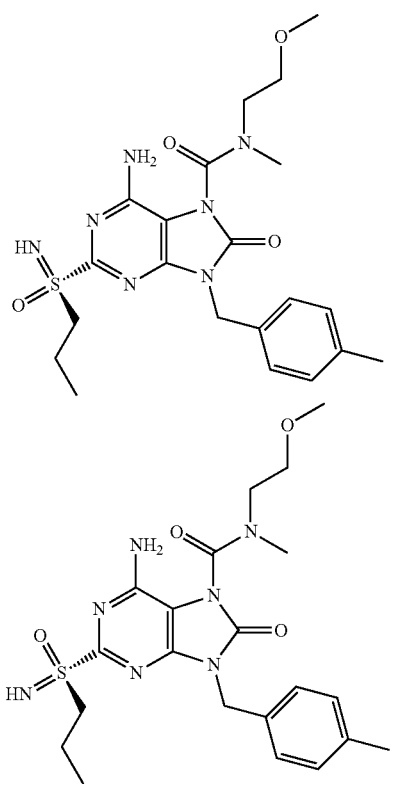

Example 38-A was prepared in analogy to Example 1, Method A, Step 6 by using Compound 36g-A and N-(2-methoxyethyl)-N-methyl-carbamoyl chloride (Intermediate AB) instead of 6-amino-9-benzyl-2-(propylsulfonimidoyl)-7H-purin-8-one (Compound 1e) and N-methyl-N-propyl-carbamoyl chloride (Intermediate AA).

Example 38-A (57.8 mg) was obtained as a white solid. $^1$H NMR (400 MHz, DMSO-d$_6$) δ ppm: 7.26 (d, J=7.6 Hz, 2H), 7.14 (d, J=7.6 Hz, 2H), 6.89-6.78 (m, 2H), 4.95 (s, 2H), 4.18 (s, 1H), 3.62-3.58 (m, 2H), 3.43-3.37 (m, 2H), 3.30-3.10 (m, 3H), 3.09-3.08 (m, 3H), 3.08-3.05 (m, 2H), 2.27 (s, 3H), 1.77-1.54 (m, 2H), 0.95 (t, J=7.4 Hz, 3H). MS obsd. (ESI$^+$) [(M+H)$^+$]: 476.3.

Example 38-B (46.6 mg) was prepared in analogy to Example 38-A by using Compound 36g-B instead of Compound 36g-A. $^1$H NMR (400 MHz, DMSO-d$_6$) δ ppm: 7.26 (d, J=7.6 Hz, 2H), 7.14 (d, J=7.6 Hz, 2H), 6.89-6.78 (m, 2H), 4.95 (s, 2H), 4.18 (s, 1H), 3.62-3.58 (m, 2H), 3.43-3.37 (m, 2H), 3.30-3.10 (m, 3H), 3.09-3.08 (m, 3H), 3.08-3.05 (m, 2H), 2.27 (s, 3H), 1.77-1.54 (m, 2H), 0.95 (t, J=7.4 Hz, 3H). MS obsd. (ESI$^+$) [(M+H)$^+$]: 476.3.

Example 39

6-Amino-N-ethyl-N-methyl-8-oxo-2-(propylsulfonimidoyl)-9-(p-tolylmethyl)purine-7-carboxamide

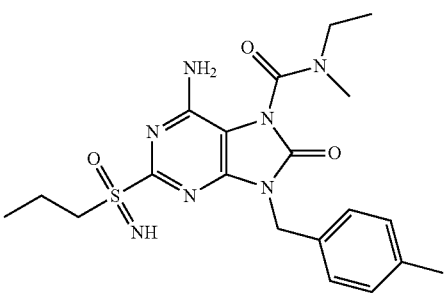

The title compound was prepared in analogy to Example 1, Method A, Step 6 by using N-ethyl-N-methyl-carbamoyl chloride and 6-amino-2-(propylsulfonimidoyl)-9-(p-tolylmethyl)-7H-purin-8-one (Compound 36g) instead of N-methyl-N-propyl-carbamoyl chloride (Intermediate AA) and 6-amino-9-benzyl-2-(propylsulfonimidoyl)-7H-purin-8-one (Compound 1e). 6-Amino-N-ethyl-N-methyl-8-oxo-2-(propylsulfonimidoyl)-9-(p-tolylmethyl)purine-7-carboxamide (141.8 mg, Example 39) was obtained as a light yellow solid. $^1$H NMR (400 MHz, DMSO-d$_6$) δ ppm: 7.26 (d, J=7.9 Hz, 2H), 7.15 (d, J=7.9 Hz, 2H), 6.89 (s, 2H), 4.95 (s, 2H), 4.24-4.07 (m, 1H), 3.52-3.35 (m, 4H), 3.10-2.95 (m, 3H), 2.26 (s, 3H), 1.77-1.55 (m, 2H), 1.24-1.10 (m, 3H), 0.95 (t, J=7.4 Hz, 3H). MS obsd. (ESI$^+$) [(M+H)$^+$]: 446.1.

Example 40

6-Amino-N-butyl-N-methyl-8-oxo-2-(propylsulfonimidoyl)-9-(p-tolylmethyl)purine-7-carboxamide

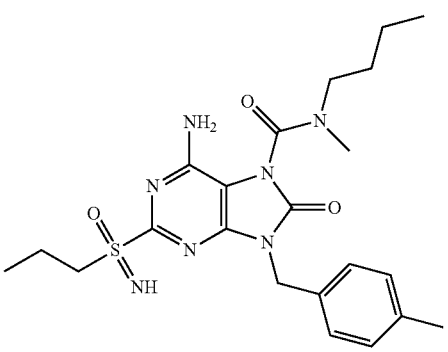

The title compound was prepared in analogy to Example 1, Method A, Step 6 by using 6-amino-2-(propylsulfonimidoyl)-9-(p-tolylmethyl)-7H-purin-8-one (Compound 36g) and N-butyl-N-methyl-carbamoyl chloride instead of 6-amino-9-benzyl-2-(propylsulfonimidoyl)-7H-purin-8-one (Compound 1e) and N-methyl-N-propyl-carbamoyl chloride (Intermediate AA). 6-Amino-N-butyl-N-methyl-8-oxo-2-(propylsulfonimidoyl)-9-(p-tolylmethyl)purine-7-carboxamide (32 mg, Example 40) was obtained as a white solid. $^1$H NMR (400 MHz, DMSO-d$_6$) δ ppm: 7.28-7.14 (m, 4H), 6.88 (s, 2H), 4.95 (s, 2H), 4.16 (s, 1H), 3.41-3.36 (m, 2H), 3.10-2.99 (m, 3H), 2.53-2.51 (m, 2H), 2.27 (s, 3H), 1.71-1.63 (m, 2H), 1.62-1.51 (m, 2H), 1.42-1.26 (m, 2H), 0.97-0.74 (m, 6H). MS obsd. (ESI$^+$) [(M+H)$^+$]: 474.3

Example 41-A and Example 41-B

6-Amino-9-[(4-chlorophenyl)methyl]-2-[S(R)-ethylsulfonimidoyl]-N-methyl-8-oxo-N-propyl-purine-7-carboxamide (Example 41-A) and 6-Amino-9-[(4-chlorophenyl)methyl]-2-[S(S)-ethylsulfonimidoyl]-N-methyl-8-oxo-N-propyl-purine-7-carboxamide (Example 41-B)

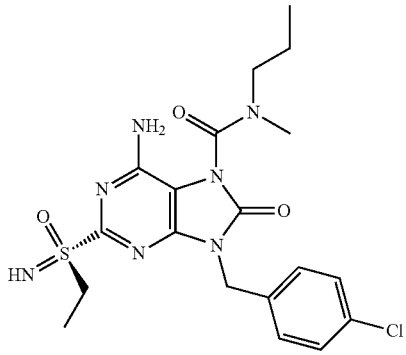

41-A

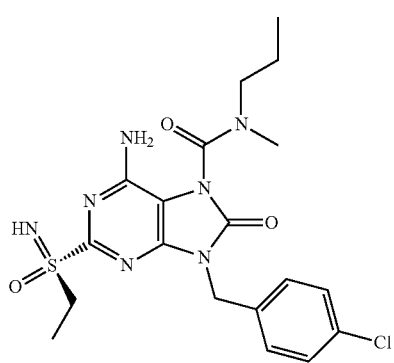

41-B

Step 1: Preparation of 6-amino-9-[(4-chlorophenyl)methyl]-2-ethylsulfanyl-7H-purin-8-one (Compound 41a)

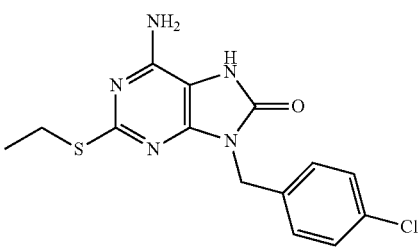

41a

Compound 41a was prepared in analogy to Example 1, Method A, Step 3 by using iodoethane and 6-amino-9-[(4-chlorophenyl)methyl]-2-sulfanyl-7H-purin-8-one (Compound 34b) instead of bromopropane and 6-amino-9-phenylmethyl-2-sulfanyl-7H-purin-8-one (Compound 1b). 6-Amino-9-[(4-chlorophenyl)methyl]-2-ethylsulfanyl-7H-purin-8-one (2.5 g, Compound 41a) was obtained as a white solid. MS obsd. (ESI$^+$) [(M+H)$^+$]: 336.

Step 2: Preparation of 6-amino-9-(4-chlorobenzyl)-2-ethylsulfinyl-7H-purin-8-one (Compound 41b)

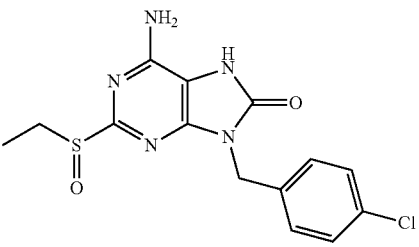

41b

Compound 41b was prepared in analogy to Example 1, Method A, Step 4 by using 6-amino-9-[(4-chlorophenyl)methyl]-2-ethyl sulfanyl-7H-purin-8-one (Compound 41a) instead of 6-amino-9-benzyl-2-propylsulfanyl-7H-purin-8-one (Compound 1c). 6-Amino-9-(4-chlorobenzyl)-2-ethylsulfinyl-7H-purin-8-one (1.94 g, Compound 41b) was obtained as a white solid. MS obsd. (ESI$^+$) [(M+H)$^+$]: 352.

Step 3: Preparation of 6-amino-9-[(4-chlorophenyl)methyl]-2-(ethylsulfonimidoyl)-7H-purin-8-one (Compound 41c)

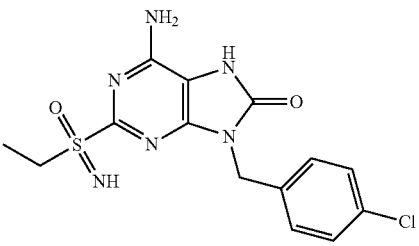

41c

Compound 41c was prepared in analogy to Example 1, Method A, Step 5 by using 6-amino-9-(4-chlorobenzyl)-2-ethylsulfinyl-7H-purin-8-one (Compound 41b) instead of 6-amino-9-benzyl-2-(2-methylsulfinyl)-7H-purin-8-one (Compound 1d). 6-Amino-9-[(4-chlorophenyl)methyl]-2-(ethylsulfonimidoyl)-7H-purin-8-one (217 mg, Example 41c) was obtained as a white solid. $^1$H NMR (400 MHz, DMSO-d$_6$) δ ppm: 10.61 (s, 1H), 7.42-7.35 (m, 4H), 6.98 (s, 2H), 4.96 (s, 2H), 4.05 (s, 1H), 3.42-3.37 (m, 2H), 1.16 (t, J=7.4 Hz, 3H). MS obsd. (ESI$^+$) [(M+H)$^+$]: 367.0.

Separation of compound of Compound 41c by chiral HPLC afforded Compound 41c-A (faster eluting, 31.8 mg)

and Compound 41c-B (slower eluting, 10 mg) as white solid with methanol 5%-40% (0.05% DEA)/CO$_2$ on ChiralPak IC-3 column.

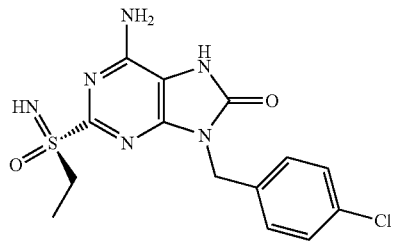
41c-A

Compound 41c-A: $^1$H NMR (400 MHz, DMSO-d$_6$) δ ppm: 10.76 (s, 1H), 7.45-7.33 (m, 4H), 7.01 (s, 2H), 4.96 (s, 2H), 4.03 (s, 1H), 3.40-3.34 (m, 2H), 1.17 (t, J=7.4 Hz, 3H). MS obsd. (ESI$^+$) [(M+H)$^+$]: 367.0.

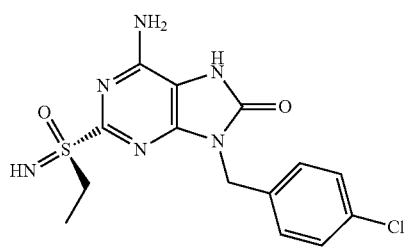
41c-B

Compound 41c-B: $^1$H NMR (400 MHz, DMSO-d$_6$) δ ppm: 10.70 (s, 1H), 7.46-7.28 (m, 4H), 7.01 (s, 2H), 4.96 (s, 2H), 4.03 (s, 1H), 3.44-3.36 (m, 2H), 1.17 (t, J=7.4 Hz, 3H). MS obsd. (ESI$^+$) [(M+H)$^+$]: 367.0.

Step 4: 6-Amino-9-[(4-chlorophenyl)methyl]-2-[S(R)-ethylsulfonimidoyl]-N-methyl-8-oxo-N-propyl-purine-7-carboxamide (Example 41-A) and 6-amino-9-[(4-chlorophenyl)methyl]-2-[S(S)-ethyl-sulfonimidoyl]-N-methyl-8-oxo-N-propyl-purine-7-carboxamide (Example 41-B)

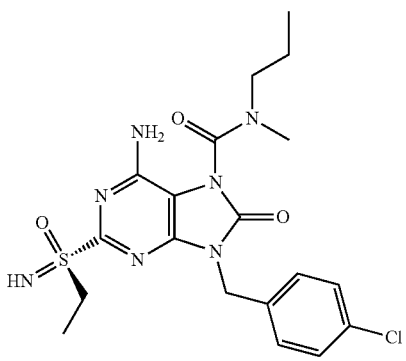
41-A

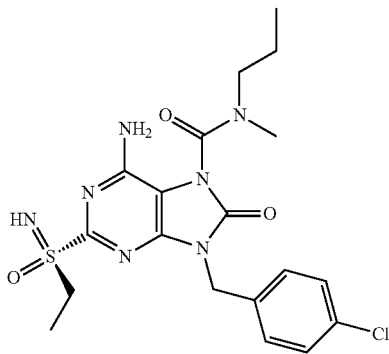
41-B

Example 41-A was prepared in analogy to Example 1, Method A, Step 6 by using Compound 41c-B instead of 6-amino-9-benzyl-2-(propylsulfonimidoyl)-7H-purin-8-one (Compound 1e). 6-Amino-9-[(4-chlorophenyl)methyl]-2-[S(R)-ethylsulfonimidoyl]-N-methyl-8-oxo-N-propyl-purine-7-carboxamide (Example 41-A, 78 mg) was obtained as a white solid. $^1$H NMR (400 MHz, DMSO-d$_6$) δ ppm: 7.43-7.41 (m, 4H), 6.90 (s, 2H), 5.00 (s, 2H), 4.19 (s, 1H), 3.46-3.39 (m, 2H), 3.39-3.38 (m, 2H), 3.09-2.99 (m, 3H), 1.69-1.52 (m, 2H), 1.19 (t, J=7.28 Hz, 3H), 0.95-0.66 (m, 3H). MS obsd. (ESI$^+$) [(M+H)$^+$]: 466.1.

Example 41-B (125 mg) was prepared in analogy to Example 1, Method A, Step 6 by using Compound 41c-A instead of 6-amino-9-benzyl-2-(propylsulfonimidoyl)-7H-purin-8-one (Compound 1e). 6-Amino-9-[(4-chlorophenyl)methyl]-2-[S(S)-ethylsulfonimidoyl]-N-methyl-8-oxo-N-propyl-purine-7-carboxamide (Example 41-B, 38 mg) was obtained as a white solid. $^1$H NMR (400 MHz, DMSO-d$_6$) δ ppm: 7.43-7.41 (m, 4H), 6.90 (s, 2H), 5.00 (s, 2H), 4.20 (s, 1H), 3.46-3.41 (m, 2H), 3.40-3.39 (m, 2H), 3.10-3.00 (m, 3H), 1.69-1.50 (m, 2H), 1.24-1.12 (m, 3H), 0.93-0.73 (m, 3H). (MS obsd. (ESI$^+$) [(M+H)$^+$]: 466.2.

The stereochemistry of Example 41-B was determined by single crystal X-ray diffraction shown in FIG. 1.

Example 42-A and Example 42-B

6-Amino-9-[(4-chlorophenyl)methyl]-N-ethyl-2[S(S)-ethylsulfonimidoyl]-N-methyl-8-oxo-purine-7-carboxamide (Example 42-A) and 6-Amino-9-[(4-chlorophenyl)methyl]-N-ethyl-2-[S(R)-ethylsulfonimidoyl]-N-methyl-8-oxo-purine-7-carboxamide (Example 42-B)

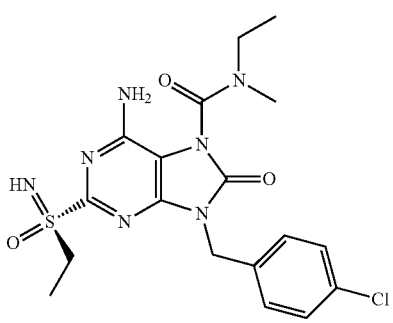
42-A

-continued

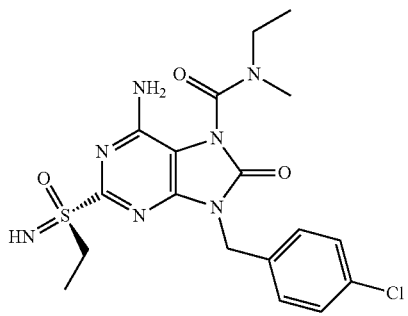

42-B

Example 42-A was prepared in analogy to Example 1, Method A, step 6 by using Compound 41c-A and N-ethyl-N-methyl-carbamoyl chloride instead of 6-amino-9-benzyl-2-(propylsulfonimidoyl)-7H-purin-8-one (Compound 1e) and N-methyl-N-propyl-carbamoyl chloride (Intermediate AA). 6-Amino-9-[(4-chlorophenyl)methyl]-N-ethyl-2[S(S)-ethylsulfonimidoyl]-N-methyl-8-oxo-purine-7-carboxamide (Example 42-A, 40 mg) was obtained as a white solid. $^1$H NMR (400 MHz, DMSO-$d_6$) δ ppm: 7.43-7.41 (m, 4H), 6.90 (s, 2H), 4.99 (s, 2H), 4.18 (s, 1H), 3.48-3.40 (m, 2H), 3.39 (s, 2H), 3.05-3.01 (m, 3H), 1.20-1.14 (m, 6H). MS obsd. (ESI$^+$) [(M+H)$^+$]: 452.2.

Example 42-B was prepared in analogy to Example 1, Method A, Step 6 by using Compound 41c-B and N-ethyl-N-methyl-carbamoyl chloride instead of 6-amino-9-benzyl-2-(propylsulfonimidoyl)-7H-purin-8-one (Compound 1e) and N-methyl-N-propyl-carbamoyl chloride (Intermediate AA). 6-Amino-9-[(4-chlorophenyl)methyl]-N-ethyl-2-[S(R)-ethylsulfonimidoyl]-N-methyl-8-oxo-purine-7-carboxamide (Example 42-B, 38 mg) was obtained as a white solid. $^1$H NMR (400 MHz, DMSO-$d_6$) δ ppm: 7.43-7.41 (m, 4H), 6.91 (s, 2H), 4.98 (s, 2H), 4.19 (s, 1H), 3.48-3.40 (m, 2H), 3.39 (s, 2H), 3.09-2.97 (m, 3H), 1.23-1.11 (m, 6H). MS obsd. (ESI$^+$) [(M+H)$^+$]: 452.2.

Figure 2:
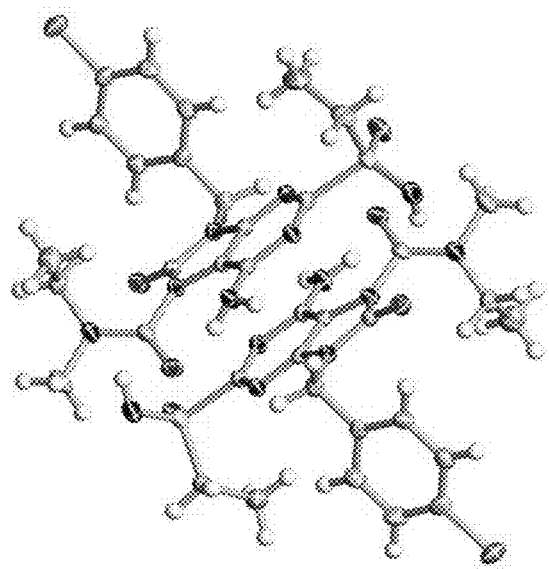
FIG. 2 Single crystal X-ray diffraction of Example 42-A.

The stereochemistry of Example 42-A was determined by single crystal X-ray diffraction shown in FIG. 2.

Example 43-A and Example 43-B

6-Amino-2-[S(R)-ethylsulfonimidoyl]-N-methyl-8-oxo-N-propyl-9-(p-tolylmethyl)purine-7-carboxamide (Example 43-A) and 6-Amino-2-[S(S)-ethylsulfonimidoyl]-N-methyl-8-oxo-N-propyl-9-(p-tolylmethyl)purine-7-carboxamide (Example 43-B)

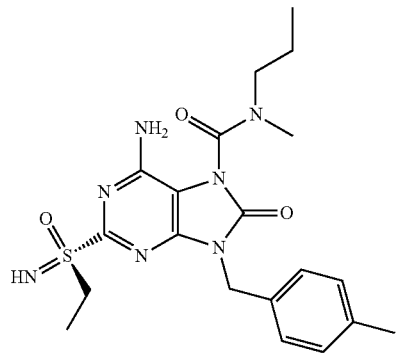

43-A

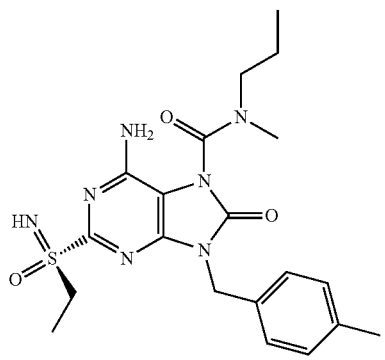

43-B

Step 1: Preparation of 4-amino-2-oxo-3-(p-tolylmethyl)-1H-imidazole-5-carbonitrile (Compound 43a)

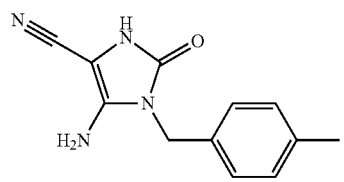

43a

Compound 43a was prepared in analogy to Example 1, Method A, Step 1 by using 4-methylbenzyl isocyanate instead of benzyl isocyanate. 4-Amino-2-oxo-3-(p-tolylmethyl)-1H-imidazole-5-carbonitrile (26.6 g, Compound 43a) was obtained as a grey solid and used directly for next step without further purification. MS obsd. (ESI$^+$) [(M+H)$^+$]: 229.2.

Step 2: Preparation of 6-amino-9-(p-tolylmethyl)-2-sulfanyl-7H-purin-8-one (Compound 43b)

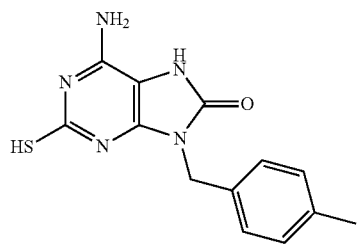

43b

Compound 43b was prepared in analogy to Example 1, Method A, Step 2 by using of 4-amino-2-oxo-3-(p-tolylmethyl)-1H-imidazole-5-carbonitrile (compound 43a) instead of 4-amino-3-benzyl-2-oxo-1H-imidazole-5-carbonitrile (Compound 1a). 6-Amino-9-(p-tolylmethyl)-2-sulfanyl-7H-purin-8-one (20.0 g, Compound 43b) was obtained as a yellow solid. MS obsd. (ESI$^+$) [(M+H)$^+$]: 288.

Step 3: Preparation of 6-amino-2-ethylsulfanyl-9-(p-tolylmethyl)-7H-purin-8-one (Compound 43c)

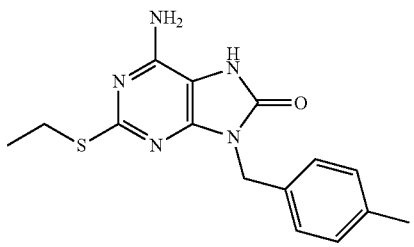

43c

Compound 43c was prepared in analogy to Example 1, Method A, Step 3 by using 6-amino-9-(p-tolylmethyl)-2-sulfanyl-7H-purin-8-one (Compound 43b) and iodoethane instead of 6-amino-9-benzyl-2-sulfanyl-7H-purin-8-one (Compound 1b) and bromopropane. 6-Amino-2-ethylsulfanyl-9-(p-tolylmethyl)-7H-purin-8-one (13 g, Compound 43c) was obtained as a yellow solid. MS obsd. (ESI$^+$) [(M+H)$^+$]: 316.

Step 4: Preparation of 6-amino-2-ethylsulfinyl-9-(p-tolylmethyl)-7H-purin-8-one (Compound 43d)

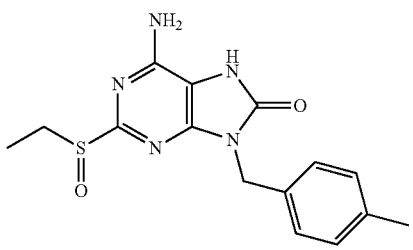

43d

Compound 43d was prepared in analogy to Example 1, Method A, Step 4 by using 6-amino-2-ethylsulfanyl-9-(mtolylmethyl)-7H-purin-8-one (Compound 43c) instead of 6-amino-9-benzyl-2-methylsulfanyl-7H-purin-8-one (Compound 1c). 6-Amino-2-ethylsulfinyl-9-(p-tolylmethyl)-7H-purin-8-one6 (3.5 g, Compound 43d) was obtained as a yellow solid. MS obsd. (ESI$^+$) [(M+H)$^+$]: 332.

Step 5: Preparation of 6-amino-2-(ethylsulfonimidoyl)-9-(p-tolylmethyl)-7H-purin-8-one (Compound 43e)

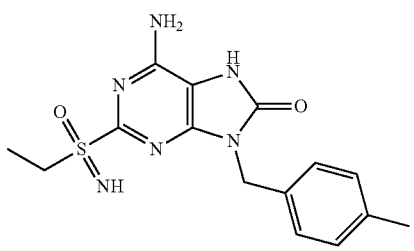

43e

Compound 43e was prepared in analogy to Example 1, Method A, Step 5 by using 6-amino-2-ethyl sulfinyl-9-(p-tolylmethyl)-7H-purin-8-one (Compound 43d) instead of 6-amino-9-benzyl-2-methylsulfinyl-7H-purin-8-one (Compound 1d). 6-Amino-2-(ethylsulfonimidoyl)-9-(p-tolylmethyl)-7H-purin-8-one (530 mg, Compound 43e) was obtained as a yellow solid. $^1$H NMR (400 MHz, DMSO-d$_6$) δ ppm: 10.53 (s, 1H), 7.24 (d, J=8.03 Hz, 2H), 7.13 (d, J=8.03 Hz, 2H), 6.94 (br. s., 2H), 4.91 (s, 2H), 4.03 (s, 1H), 3.36-3.41 (m, 2H), 2.26 (s, 3H), 1.18 (t, J=7.28 Hz, 3H). MS obsd. (ESI$^+$) [(M+H)$^+$]: 347.

Separation of compound of Compound 43e by chiral HPLC afforded Compound 43e-A (faster eluting, 56.8 mg) and Compound 43e-B (slower eluting, 56.7 mg) as white solid with methanol 5%-40% (0.05% DEA)/CO$_2$ on ChiralPak AD-3 column.

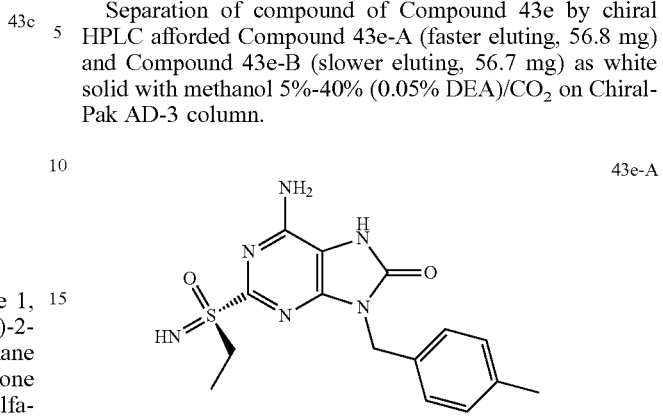

Compound 43e-A: $^1$H NMR (400 MHz, DMSO-d$_6$) δ ppm: 10.52 (br. s., 1H), 7.23 (d, J=8.0 Hz, 2H), 7.13 (d, J=7.9 Hz, 2H), 6.94 (br. s., 2H), 4.90 (s, 2H), 4.03 (s, 1H), 3.42-3.33 (m, 2H), 2.25 (s, 3H), 1.17 (t, J=7.3 Hz, 3H). MS obsd. (ESI$^+$) [(M+H)$^+$]: 347.

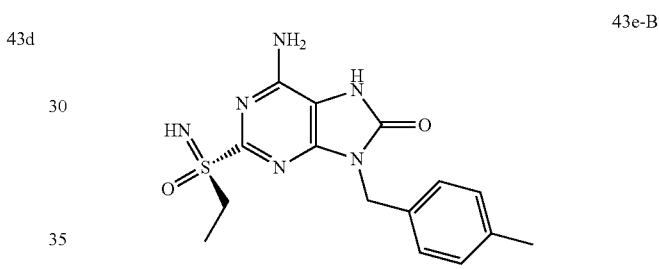

Compound 43e-B: $^1$H NMR (400 MHz, DMSO-d$_6$) δ ppm: 10.56 (br. s., 1H), 7.23 (d, J=8.0 Hz, 2H), 7.13 (d, J=8.0 Hz, 2H), 6.95 (br. s., 2H), 4.90 (s, 2H) 4.03 (s, 1H), 3.44-3.29 (m, 2H), 2.25 (s, 3H), 1.17 (t, J=7.3 Hz, 3H). MS obsd. (ESI$^+$) [(M+H)$^+$]: 347.

Step 6: Preparation of 6-Amino-2-[S(R)-ethylsulfonimidoyl]-N-methyl-8-oxo-N-propyl-9-(p-tolylmethyl)purine-7-carboxamide (Example 43-A) and 6-Amino-2-[S(S)-ethylsulfonimidoyl]-N-methyl-8-oxo-N-propyl-9-(p-tolylmethyl)purine-7-carboxamide (Example 43-B)

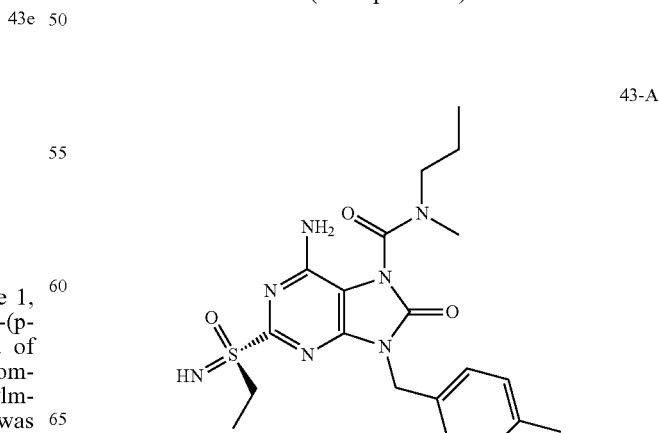

43-A

-continued

43-B

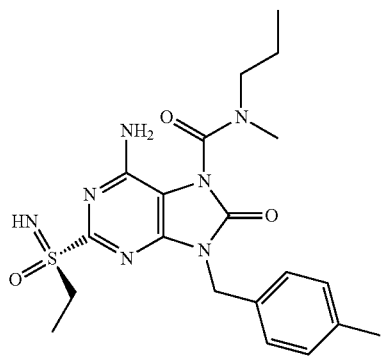

Example 43-A was prepared in analogy to Example 1, Method A, Step 6 by using Compound 43e-A instead of 6-amino-9-benzyl-2-(propylsulfonimidoyl)-7H-purin-8-one (Compound 1e). 6-Amino-2-[S(R)-ethylsulfonimidoyl]-N-methyl-8-oxo-N-propyl-9-(p-tolylmethyl)purine-7-carboxamide (Example 43-A, 58.1 mg, faster eluting, isopropanol from 5% to 40% (0.05% DEA)/$CO_2$ on ChiralPak AD-3 column) was obtained as a white solid. $^1$H NMR (400 MHz, DMSO-$d_6$) δ ppm: 7.28 (d, J=7.8 Hz, 2H), 7.15 (d, J=7.8 Hz, 2H), 6.88 (br. s., 2H), 5.03-4.87 (m, 2H), 4.19 (s, 1H), 3.61-3.36 (m, 4H), 3.11-2.96 (m, 3H), 2.26 (s, 3H), 1.72-1.45 (m, 2H), 1.20 (t, J=7.2 Hz, 3H), 0.97-0.65 (m, 3H). MS obsd. (ESI$^+$) [(M+H)$^+$]: 446.

Example 43-B was prepared in analogy to Example 1, Method A, Step 6 by using Compound 43e-B instead of 6-amino-9-benzyl-2-(propylsulfonimidoyl)-7H-purin-8-one (Compound 1e). 6-Amino-2-[S(S)-ethylsulfonimidoyl]-N-methyl-8-oxo-N-propyl-9-(p-tolylmethyl)purine-7-carboxamide (Example 43-B, 40.1 mg, slower eluting, isopropanol from 5% to 40% (0.05% DEA)/$CO_2$ on ChiralPak AD-3 column) was obtained as a white solid: $^1$H NMR (400 MHz, DMSO-$d_6$) δ ppm: 7.28 (d, J=7.5 Hz, 2H), 7.15 (d, J=7.5 Hz, 2H), 6.89 (br. s., 2H), 5.03-4.86 (m, 2H), 4.19 (s, 1H), 3.49-3.37 (m, 4H), 3.08-3.00 (m, 3H), 2.27 (s, 3H), 1.70-1.48 (m, 2H), 1.20 (t, J=7.2 Hz, 3H), 0.95-0.71 (m, 3H). MS obsd. (ESI$^+$) [(M+H)$^+$]: 446.3.

Figure 3:
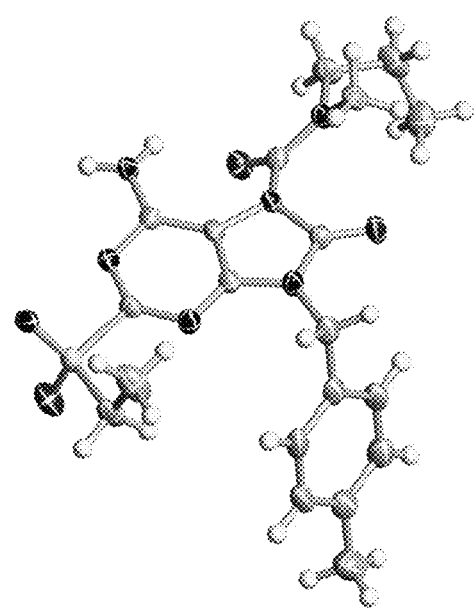
FIG. 3 Single crystal X-ray diffraction of Example 43-B.

The stereochemistry of Example 43-B was determined by single crystal X-ray diffraction shown in FIG. 3.

Example 44-A and Example 44-B

6-Amino-N-ethyl-2[S(S)-ethylsulfonimidoyl]-N-methyl-8-oxo-9-(p-tolylmethyl)purine-7-carboxamide (Example 44-A) and 6-Amino-N-ethyl-2-[S(R)-ethylsulfonimidoyl]-N-methyl-8-oxo-9-(p-tolylmethyl)purine-7-carboxamide (Example 44-B)

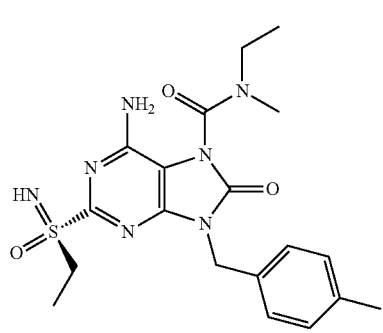

44-A

-continued

44-B

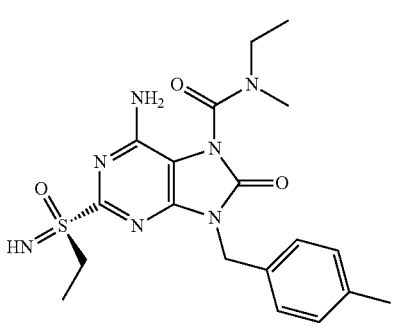

Example 44-A was prepared in analogy to Example 1, Method A, Step 6 by using Compound 43e-B and N-ethyl-N-methyl-carbamoyl chloride instead of 6-amino-9-benzyl-2-(propylsulfonimidoyl)-7H-purin-8-one (Compound 1e) and N-methyl-N-propyl-carbamoyl chloride (Intermediate AA). 6-Amino-N-ethyl-2[S(S)-ethylsulfonimidoyl]-N-methyl-8-oxo-9-(p-tolylmethyl)purine-7-carboxamide (Example 44-A, 73.1 mg) was obtained as a white solid. $^1$H NMR (400 MHz, DMSO-$d_6$) δ ppm: 7.28 (d, J=7.8 Hz, 2H), 7.15 (d, J=7.8 Hz, 2H), 6.90 (br. s., 2H), 4.95 (s, 2H), 4.19 (br. s., 1H), 3.48-3.39 (m, 4H), 3.06-3.00 (m, 3H), 2.27 (s, 3H), 1.29-1.04 (m, 6H). MS obsd. (ESI$^+$) [(M+H)$^+$]: 432.

Example 44-B was prepared in analogy to Example 1, Method A, Step 6 by using Compound 43e-A and N-ethyl-N-methyl-carbamoyl chloride instead of 6-amino-9-benzyl-2-(propylsulfonimidoyl)-7H-purin-8-one (Compound 1e) and N-methyl-N-propyl-carbamoyl chloride (Intermediate AA). 6-Amino-N-ethyl-2-[S(R)-ethylsulfonimidoyl]-N-methyl-8-oxo-9-(p-tolylmethyl)purine-7-carboxamide (Example 44-B, 46.7 mg) was obtained as a white solid: $^1$H NMR (400 MHz, DMSO-$d_6$) δ ppm: 7.28 (d, J=7.9 Hz, 2H), 7.15 (d, J=7.9 Hz, 2H), 6.90 (br. s., 2H), 4.95 (s, 2H), 4.19 (br. s., 1H), 3.50-3.39 (m, 4H), 3.10-2.96 (m, 3H), 2.27 (s, 3H), 1.27-1.10 (m, 6H). MS obsd. (ESI$^+$) [(M+H)$^+$]: 432.

Example 45-A and Example 45-B

6-Amino-2-[S(R)ethylsulfonimidoyl]-9-[(4-fluorophenyl)methyl]-N-methyl-8-oxo-N-propyl-purine-7-carboxamide and 6-Amino-2-[S(S)ethylsulfonimidoyl]-9-[(4-fluorophenyl)methyl]-N-methyl-8-oxo-N-propyl-purine-7-carboxamide

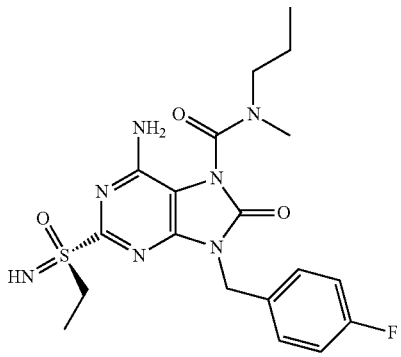

-continued

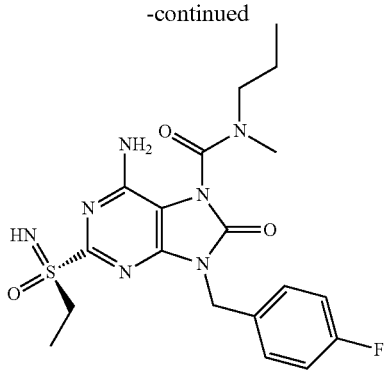

Step 1: Preparation of 4-amino-3-[(4-fluorophenyl)methyl]-2-oxo-1H-imidazole-5-carbonitrile (Compound 45a)

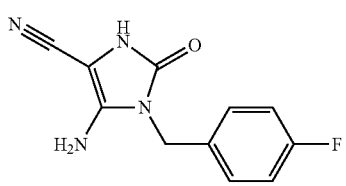

45a

Compound 45a was prepared in analogy to Example 1, Method A, Step 1 by using 4-fluorobenzyl isocyanate instead of benzyl isocyanate. 4-Amino-3-[(4-fluorophenyl)methyl]-2-oxo-1H-imidazole-5-carbonitrile (48 g, Compound 45a) was obtained as a light yellow solid and was used directly for next step without further purification. MS obsd. (ESI⁺) [(M+H)⁺]: 233.

Step 2: Preparation of 6-amino-9-[(4-fluorophenyl)methyl]-2-sulfanyl-7H-purin-8-one (Compound 45b)

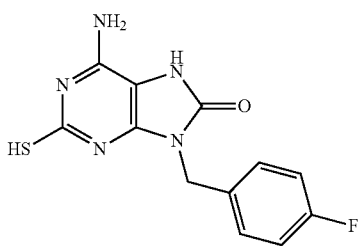

45b

Compound 45b was prepared in analogy to Example 1, Method A, Step 2 by using of 4-amino-3-[(4-fluorophenyl)methyl]-2-oxo-1H-imidazole-5-carbonitrile (Compound 45a) instead of 4-amino-3-phenylmethyl-2-oxo-1H-imidazole-5-carbonitrile (Compound 1a). 6-Amino-9-[(4-fluorophenyl)methyl]-2-sulfanyl-7H-purin-8-one (32.0 g, Compound 45b) was obtained as a yellow solid. MS obsd. (ESI⁺) [(M+H)⁺]: 292.

Step 3: Preparation of 6-amino-2-ethylsulfanyl-9-[(4-fluorophenyl)methyl]-7H-purin-8-one (Compound 45c)

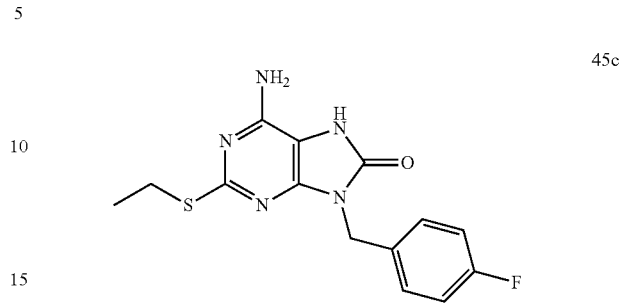

45c

Compound 45c was prepared in analogy to Example 1, Method A, Step 3 by using 6-amino-9-[(4-fluorophenyl)methyl]-2-sulfanyl-7H-purin-8-one (Compound 45b) and iodoethane instead of 6-amino-9-benzyl-2-sulfanyl-7H-purin-8-one (Compound 1b) and bromopropane. 6-Amino-2-ethylsulfanyl-9-[(4-fluorophenyl)methyl]-7H-purin-8-one (5.6 g, Compound 45c) was obtained as a yellow solid. MS obsd. (ESI⁺) [(M+H)⁺]: 320.

Step 5: Preparation of 6-amino-2-ethylsulfinyl-9-[(4-fluorophenyl)methyl]-7H-purin-8-one (Compound 45d)

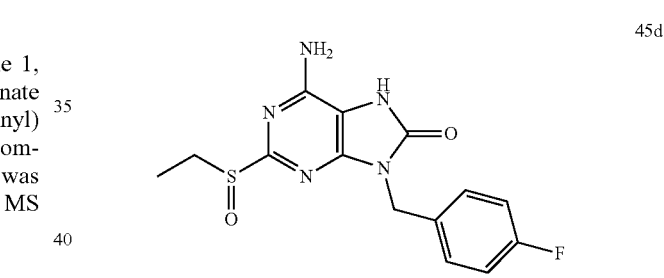

45d

Compound 45d was prepared in analogy to Example 1, Method A, Step 4 by using 6-amino-2-ethylsulfanyl-9-[(4-fluorophenyl)methyl]-7H-purin-8-one (Compound 45c) instead of 6-amino-9-benzyl-2-propylsulfanyl-7H-purin-8-one (Compound 1c). 6-Amino-2-ethylsulfinyl-9-[(4-fluorophenyl)methyl]-7H-purin-8-one (4.8 g, Compound 45d) was obtained as a yellow solid. MS obsd. (ESI⁺) [(M+H)⁺]: 332.

Step 6: Preparation of 6-amino-2-(ethylsulfonimidoyl)-9-[(4-fluorophenyl)methyl]-7H-purin-8-one (Compound 45e)

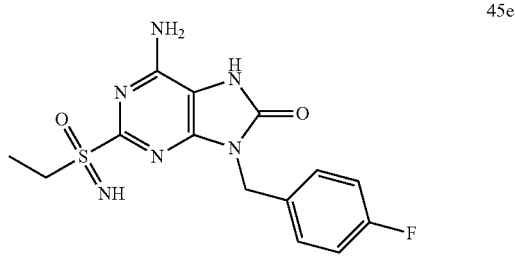 [SMILES: CCS(=N)(=O)c1nc(N)c2[nH]c(=O)n(Cc3ccc(F)cc3)c2n1]

45e

Compound 45e was prepared in analogy to Example 1, Method A, Step 5 by using 6-amino-2-ethylsulfinyl-9-[(4-fluorophenyl)methyl]-7H-purin-8-one (Compound 45d) instead of 6-amino-9-benzyl-2-propylsulfinyl-7H-purin-8-one (Compound 1d). 6-Amino-2-(ethylsulfonimidoyl)-9-[(4-fluorophenyl)methyl]-7H-purin-8-one (2.9 g, Compound 45e) was obtained as a yellow solid. $^1$H NMR (400 MHz, DMSO-d$_6$) δ ppm: 10.57 (br. s., 1H), 7.40 (dd, J=8.5, 5.5 Hz, 2H), 7.16 (t, J=8.9 Hz, 2H), 6.97 (br. s., 2H), 4.94 (s, 2H), 4.07 (s, 1H), 3.43-3.36 (m, 2H), 1.17 (t, J=7.4 Hz, 3H). MS obsd. (ESI$^+$) [(M+H)$^+$]: 351.

Separation of compound 45e by chiral HPLC afforded Compound 45e-A (faster eluting, 85.4 mg) and Compound 45e-B (slower eluting, 36.4 mg) as white solid with methanol 5%-40% (0.05% DEA)/CO$_2$ on ChiralPak AD-3 column.

Compound 45e-A: $^1$H NMR (400 MHz, DMSO-d$_6$) δ ppm: 10.53 (br. s., 1H), 7.41 (dd, J=8.5, 5.5 Hz, 2H), 7.17 (t, J=8.9 Hz, 2H), 6.98 (br. s., 2H), 4.95 (s, 2H), 4.07 (s, 1H), 3.45-3.36 (m, 2H), 1.17 (t, J=7.3 Hz, 3H). MS obsd. (ESI$^+$) [(M+H)$^+$]: 351.

Compound 45e-B: $^1$H NMR (400 MHz, DMSO-d$_6$) ppm: 10.53 (br. s., 1H), 7.41 (dd, J=8.5, 5.5 Hz, 2H), 7.17 (t, J=8.9 Hz, 2H), 6.98 (br. s., 2H), 4.95 (s, 2H), 4.07 (s, 1H), 3.44-3.37 (m, 2H) 1.17 (t, J=7.3 Hz, 3H). MS obsd. (ESI$^+$) [(M+H)$^+$]: 351.

Step 7: Preparation of 6-amino-2-(ethylsulfonimidoyl)-9-[(4-fluorophenyl)methyl]-N-methyl-8-oxo-N-propyl-purine-7-carboxamide (Example 45), 6-Amino-2-[S(R)ethylsulfonimidoyl]-9-[(4-fluorophenyl)methyl]-N-methyl-8-oxo-N-propyl-purine-7-carboxamide and 6-Amino-2-[S(S)ethylsulfonimidoyl]-9-[(4-fluorophenyl)methyl]-N-methyl-8-oxo-N-propyl-purine-7-carboxamide (Example 45-A and Example 45-B)

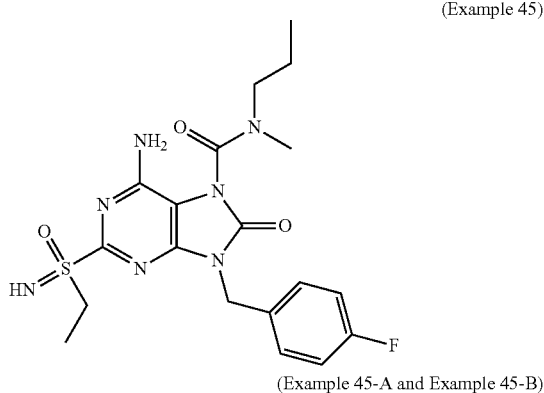

(Example 45)

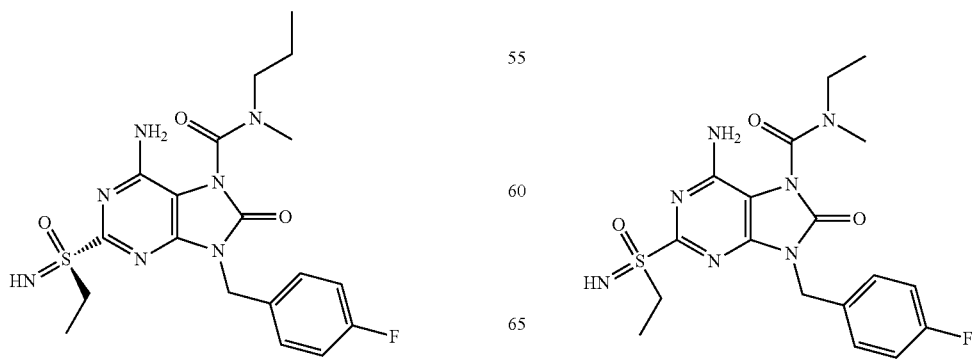

(Example 45-A and Example 45-B)

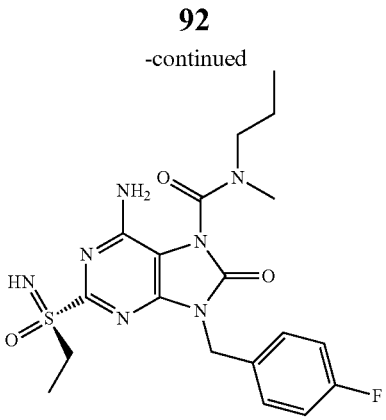

Example 45 was prepared in analogy to Example 1, Method A, Step 6 by using 6-amino-2-(ethylsulfonimidoyl)-9-[(4-fluorophenyl)methyl]-7H-purin-8-one (Compound 45e) instead of 6-amino-9-benzyl-2-(propylsulfonimidoyl)-7H-purin-8-one (Compound 1e). 6-Amino-2-(ethylsulfonimidoyl)-9-[(4-fluorophenyl)methyl]-N-methyl-8-oxo-N-propyl-purine-7-carboxamide (162.4 mg, Example 45) was obtained as a white solid.

Separation of compound of Example 45 by chiral HPLC afforded Example 45-A (faster eluting, 85.3 mg) and Example 45-B (slower eluting, 52 mg) as white solid with methanol 5%-40% (0.05% DEA)/CO$_2$ on ChiralPak AD-3 column Example 45-A: $^1$H NMR (400 MHz, DMSO-d$_6$) δ ppm: 7.53-7.38 (m, 2H), 7.18 (t, J=8.9 Hz, 2H), 6.90 (br. s., 2H), 4.99 (s, 2H), 4.21 (s, 1H), 3.48-3.37 (m, 4H), 3.10-3.01 (m, 3H), 1.69-1.49 (m, 2H), 1.25-1.14 (m, 3H), 0.94-0.72 (m, 3H). MS obsd. (ESI$^+$) [(M+H)$^+$]: 450.

Example 45-B: $^1$H NMR (400 MHz, DMSO-d$_6$) δ ppm: 7.54-7.38 (m, 2H), 7.18 (t, J=8.9 Hz, 2H), 7.01-6.72 (m, 2H), 4.99 (s, 2H), 4.21 (s, 1H), 3.46-3.38 (m, 4H), 3.10-3.01 (m, 3H), 1.76-1.50 (m, 2H), 1.25-1.16 (m, 3H), 0.99-0.69 (m, 3H). MS obsd. (ESI$^+$) [(M+H)$^+$]: 450.

Example 46-A and Example 46-B

6-Amino-N-ethyl-2-(ethylsulfonimidoyl)-9-[(4-fluorophenyl)methyl]-N-methyl-8-oxo-purine-7-carboxamide (Example 46), 6-amino-N-ethyl-2-[S(S)-(ethylsulfonimidoyl)]-9-[(4-fluorophenyl)methyl]-N-methyl-8-oxo-purine-7-carboxamide and 6-amino-N-ethyl-2-[S(R)-(ethylsulfonimidoyl)]-9-[(4-fluorophenyl)methyl]-N-methyl-8-oxo-purine-7-carboxamide (Example 46-A and Example 46-B)

-continued (Example 46-A and Example 46-B)

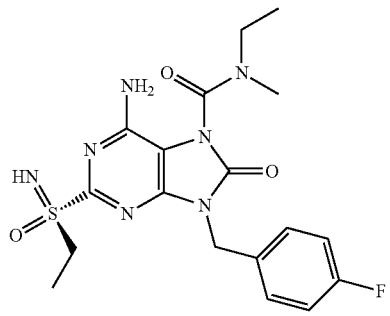

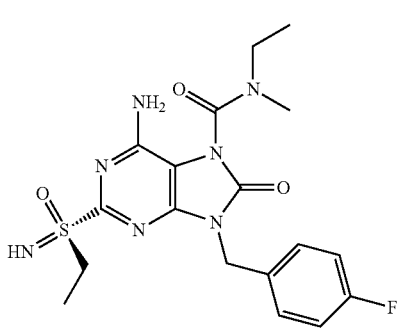

Example 46 was prepared in analogy to Example 1, Method A, Step 6 by using 6-amino-2-(ethylsulfonimidoyl)-9-[(4-fluorophenyl)methyl]-7H-purin-8-one (Compound 45e) and N-ethyl-N-methyl carbamoyl chloride instead of 6-amino-9-benzyl-2-(propyl sulfonimidoyl)-7H-purin-8-one (Compound 1e) and N-methyl-N-propyl-carbamoyl chloride (Intermediate AA). 6-Amino-N-ethyl-2-(ethylsulfonimidoyl)-9-[(4-fluorophenyl)methyl]-N-methyl-8-oxo-purine-7-carboxamide (51 mg, Example 46) was obtained as a white solid. $^1$H NMR (400 MHz, DMSO-$d_6$) δ ppm: 7.46-7.43 (m, 2H), 7.20-7.15 (m, 2H), 6.90 (br. s., 2H), 4.98 (s, 2H), 4.18 (s, 1H), 3.47-3.32 (m, 4H), 3.05-3.01 (m, 3H), 1.21-1.14 (m, 6H). MS obsd. (ESI$^+$) [(M+H)$^+$]: 436.

Separation of compound of Example 46 by chiral HPLC afforded Example 46-A (faster eluting, 72 mg) and Example 46-B (slower eluting, 45 mg) as white solid with methanol 5%-40% (0.05% DEA)/CO$_2$ on ChiralPak AD-3 column Example 46-A: $^1$H NMR (400 MHz, DMSO-$d_6$) δ ppm: 7.46-7.43 (m, 2H), 7.20-7.16 (m, 2H), 6.90 (br. s., 2H), 4.98 (s, 2H), 4.18 (s, 1H), 3.47-3.32 (m, 4H), 3.05-3.01 (m, 3H), 1.21-1.14 (m, 6H). MS obsd. (ESI$^+$) [(M+H)$^+$]: 436.

Example 46-B: $^1$H NMR (400 MHz, DMSO-$d_6$) δ ppm: 7.46-7.43 (m, 2H), 7.20-7.14 (m, 2H), 6.92 (br. s., 2H), 4.98 (s, 2H), 4.20 (br. s., 1H), 3.47-3.32 (m, 4H), 3.05-3.01 (m, 3H), 1.23-1.19 (m, 6H). MS obsd. (ESI$^+$) [(M+H)$^+$]: 436.

Example 47-A and Example 47-B

6-Amino-9-[(4-bromophenyl)methyl]-2-(ethylsulfonimidoyl)-N-methyl-8-oxo-N-propyl-purine-7-carboxamide (Example 47), 6-amino-2-[S(R)-ethylsulfonimidoyl]-9-[(4-bromophenyl)methyl]-N-methyl-8-oxo-N-propyl-purine-7-carboxamide and 6-amino-2-[S(S)-ethylsulfonimidoyl]-9-[(4-bromophenyl)methyl]-N-methyl-8-oxo-N-propyl-purine-7-carboxamide (Example 47)

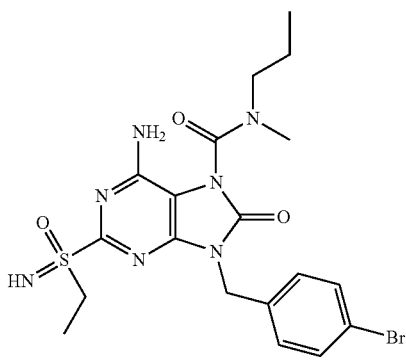

(Example 47-A and Example 47-B)

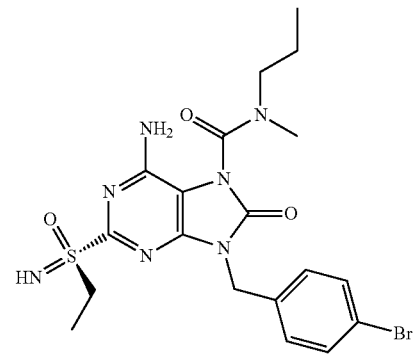

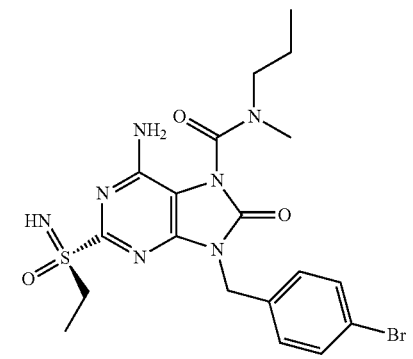

Step 1: Preparation of 4-amino-3-[(4-bromophenyl)methyl]-2-oxo-1H-imidazole-5-carbonitrile (Compound 47a)

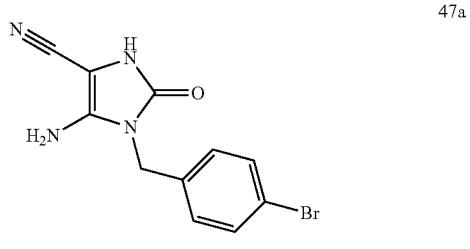 [SMILES: N#Cc1[nH]c(=O)n(Cc2ccc(Br)cc2)c1N]

Compound 47a was prepared in analogy to Example 1, Method A, Step 1 by using 4-bromobenzyl isocyanate instead of benzyl isocyanate. 4-Amino-3-[(4-bromophenyl)methyl]-2-oxo-1H-imidazole-5-carbonitrile (500 mg, Compound 47a) was obtained as a light yellow solid and was used directly for next step without further purification. $^1$H NMR (400 MHz, DMSO-$d_6$) δ ppm: 9.94 (S, 1H), 7.55-7.53 (d, J=8.0 Hz, 2H), 7.20-7.18 (d, J=8.0 Hz, 2H), 6.52 (br. s., 2H), 4.74 (s, 2H). MS obsd. (ESI$^+$) [(M+H)$^+$]: 293.

Step 2: Preparation of 6-amino-9-[(4-bromophenyl)methyl]-2-sulfanyl-7H-purin-8-one (Compound 47b)

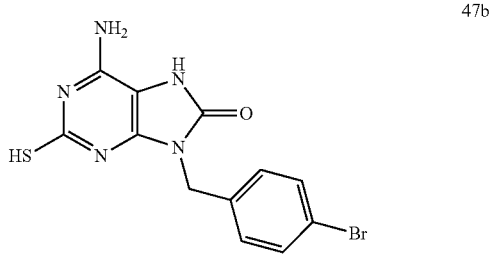

Compound 47b was prepared in analogy to Example 1, Method A, Step 2 by using of 4-amino-3-[(4-bromophenyl)methyl]-2-oxo-1H-imidazole-5-carbonitrile (Compound 47a) instead of 4-amino-3-phenylmethyl-2-oxo-1H-imidazole-5-carbonitrile (Compound 1a). 6-Amino-9-[(4-bromophenyl)methyl]-2-sulfanyl-7H-purin-8-one (300 mg, Compound 47b) was obtained as a yellow solid. MS obsd. (ESI$^+$) [(M+H)$^+$]: 352.

Step 3: Preparation of 6-amino-2-ethylsulfanyl-9-[(4-bromophenyl)methyl]-7H-purin-8-one (Compound 47c)

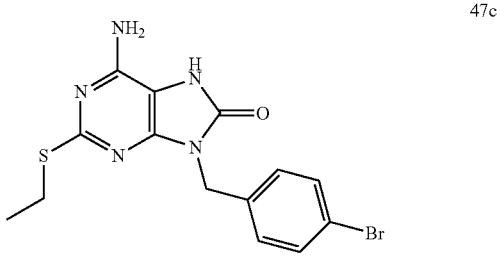 [SMILES: CCSc1nc(N)c2[nH]c(=O)n(Cc3ccc(Br)cc3)c2n1]

Compound 47c was prepared in analogy to Example 1, Method A, Step 3 by using 6-amino-9-[(4-bromophenyl)methyl]-2-sulfanyl-7H-purin-8-one (Compound 45b) and iodoethane instead of 6-amino-9-benzyl-2-sulfanyl-7H-purin-8-one (Compound 1b) and bromopropane. 6-Amino-2-ethylsulfanyl-9-[(4-bromophenyl)methyl]-7H-purin-8-one (5.6 g, Compound 47c) was obtained as a yellow solid. MS obsd. (ESI$^+$) [(M+H)$^+$]: 380.

Step 4: Preparation of 6-amino-9-[(4-bromophenyl)methyl]-2-ethylsulfinyl-7H-purin-8-one (Compound 47d)

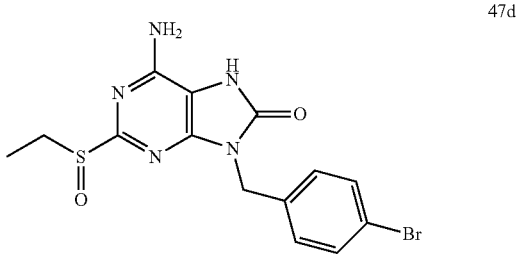 [SMILES: CCS(=O)c1nc(N)c2[nH]c(=O)n(Cc3ccc(Br)cc3)c2n1]

Compound 47d was prepared in analogy to Example 1, Method B, Step 6 by using 6-amino-9-[(4-bromophenyl)methyl]-2-ethylsulfanyl-7H-purin-8-one (Compound 47c) instead of 6-amino-9-benzyl-2-(2-propylsulfanyl)-7H-purin-8-one (Compound 1c). 6-Amino-9-[(4-bromophenyl)methyl]-2-ethylsulfinyl-7H-purin-8-one (3.2 g, Compound 47d) was obtained as a white solid. MS obsd. (ESI$^+$) [(M+H)$^+$]: 396.

Step 5: Preparation of 6-amino-9-[(4-bromophenyl)methyl]-2-(ethylsulfonimidoyl)-7H-purin-8-one (Compound 47e)

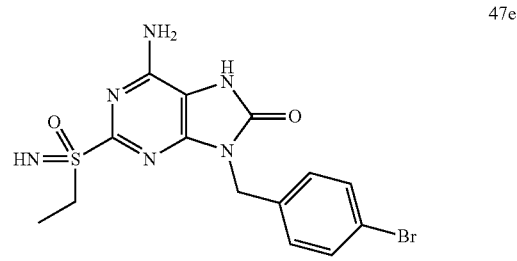 [SMILES: CCS(=N)(=O)c1nc(N)c2[nH]c(=O)n(Cc3ccc(Br)cc3)c2n1]

Compound 47e was prepared in analogy to Example 1, Method B, Step 7 by using 6-amino-9-[(4-bromophenyl)methyl]-2-ethylsulfinyl-7H-purin-8-one (Compound 47d) instead of 6-amino-9-benzyl-2-propylsulfinyl-7H-purin-8-one (Compound 1d). 6-Amino-9-[(4-bromophenyl)methyl]-2-(ethylsulfonimidoyl)-7H-purin-8-one (4.0 g, Compound 47e) was obtained as a white solid. MS obsd. (ESI$^+$) [(M+H)$^+$]: 411.

Compound 47e-A and Compound 47e-B

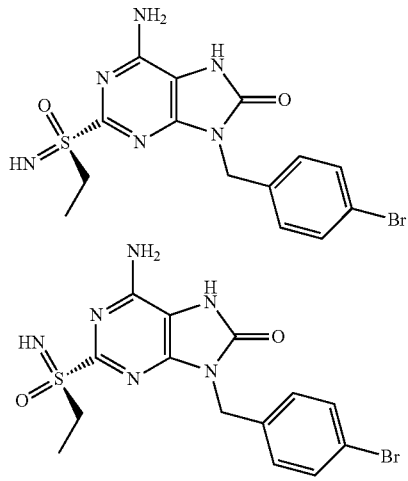

Separation of compound of Compound 47e by chiral HPLC afforded Compound 47e-A (faster eluting, 112 mg) and Compound 47e-B (slower eluting, 99 mg) as white solid with methanol 5%-40% (0.05% DEA)/CO$_2$ on ChiralPak AD-3 column.

Compound 47e-A: $^1$H NMR (400 MHz, DMSO-d$_6$) ppm: 10.58 (br. s., 1H), 7.52-7.54 (d, J=8.0, 2H), 7.31-7.29 (t, J=8.0 Hz, 2H), 6.54 (br. s., 2H), 4.93 (s, 2H), 4.05 (s, 1H), 3.42-3.31 (m, 2H), 1.15 (t, J=7.3 Hz, 3H). MS obsd. (ESI$^+$) [(M+H)$^+$]: 411.

Compound 47e-B: $^1$H NMR (400 MHz, DMSO-d$_6$) δ ppm: 10.58 (br. s., 1H), 7.54-7.52 (d, J=8.0, 2H), 7.31-7.29 (t, J=8.0 Hz, 2H), 6.98 (br. s., 2H), 4.93 (s, 2H), 4.06 (s, 1H), 3.40-3.37 (m, 2H), 1.15 (t, J=7.3 Hz, 3H). MS obsd. (ESI$^+$) [(M+H)$^+$]: 411.

Step 6: Preparation of 6-amino-9-[(4-bromophenyl) methyl]-2-(ethylsulfonimidoyl)-N-methyl-8-oxo-N-propyl-purine-7-carboxamide (Example 47), 6-amino-9-[(4-bromophenyl)methyl]-2-[S(R)-ethyl-sulfonimidoyl]-N-methyl-8-oxo-N-propyl-purine-7-carboxamide and 6-amino-9-[(4-bromophenyl) methyl]-2-[S(S)-ethylsulfonimidoyl]-N-methyl-8-oxo-N-propyl-purine-7-carboxamide (Example 47-A and Example 47-B)

(Example 47)

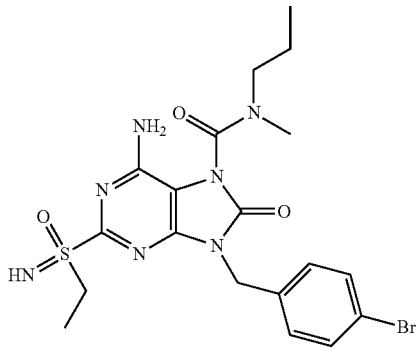

(Example 47-A and Example 47-B)

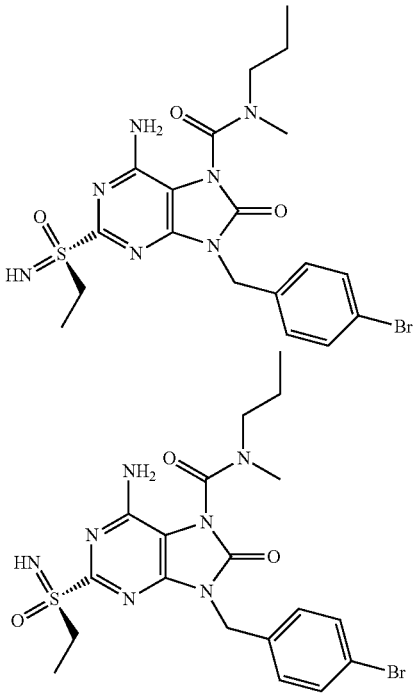

Example 47 was prepared in analogy to Example 1, Method A, Step 6 by using 6-amino-9-[(4-bromophenyl) methyl]-2-(ethylsulfonimidoyl)-7H-purin-8-one (Compound 47e) instead of 6-amino-9-benzyl-2-(propylsulfonimidoyl)-7H-purin-8-one (Compound 1e). 6-Amino-9-[(4-bromophenyl)methyl]-2-(ethylsulfonimidoyl)-N-methyl-8-oxo-N-propyl-purine-7-carboxamide (570 mg, Example 47) was obtained as a white solid. $^1$H NMR (400 MHz, DMSO-d$_6$) δ ppm: 7.56-7.53 (m, 2H), 7.36-7.34 (m, 2H), 6.92 (br. s., 2H), 4.97 (s, 2H), 4.18 (s, 1H), 3.45-3.38 (m, 4H), 3.05-3.02 (m, 3H), 1.65-1.56 (m, 2H), 1.19 (t, J=8.0 Hz, 3H), 0.93-0.75 (m, 3H). MS obsd. (ESI$^+$) [(M+H)$^+$]: 510.

Separation of compound of Example 47 by chiral HPLC afforded Example 47-A (faster eluting, 260 mg) and Example 47-B (slower eluting, 266 mg) as white solid with methanol 5%-40% (0.05% DEA)/CO$_2$ on ChiralPak AD-3 column Example 47-A: $^1$H NMR (400 MHz, DMSO-d$_6$) δ ppm: 7.56-7.54 (d, J=8.0 Hz, 2H), 7.36-7.33 (d, J=8.0 Hz, 2H), 6.90 (br. s., 2H), 4.97 (s, 2H), 4.21 (s, 1H), 3.46-3.41 (m, 4H), 3.05-3.02 (m, 3H), 1.65-1.54 (m, 2H), 1.24-1.16 (m, 3H), 0.93-0.75 (m, 3H). MS obsd. (ESI$^+$) [(M+H)$^+$]: 510.

Example 47-B: $^1$H NMR (400 MHz, DMSO-d$_6$) δ ppm: 7.54-7.53 (d, J=8.0 Hz, 2H), 7.36-7.33 (d, J=8.0 Hz, 2H), 6.90 (br. s., 2H), 4.97 (s, 2H), 4.21 (s, 1H), 3.46-3.41 (m, 4H), 3.06-3.02 (m, 3H), 1.65-1.54 (m, 2H), 1.20-1.16 (m, 3H), 0.93-0.75 (m, 3H). MS obsd. (ESI$^+$) [(M+H)$^+$]: 510.

Example 48-A and Example 48-B

6-Amino-9-[(4-bromophenyl)methyl]-N-ethyl-2-(ethylsulfonimidoyl)-N-methyl-8-oxo-purine-7-carboxamide (Example 48), 6-amino-9-[(4-bromophenyl)methyl]-N-ethyl-2-[S(S)-(ethylsulfonimidoyl)]-N-methyl-8-oxo-purine-7-carboxamide and 6-amino-9-[(4-bromophenyl)methyl]-N-ethyl-2-[S(R)-(ethylsulfonimidoyl)]-N-methyl-8-oxo-purine-7-carboxamide (Example 48-A and Example 48-B)

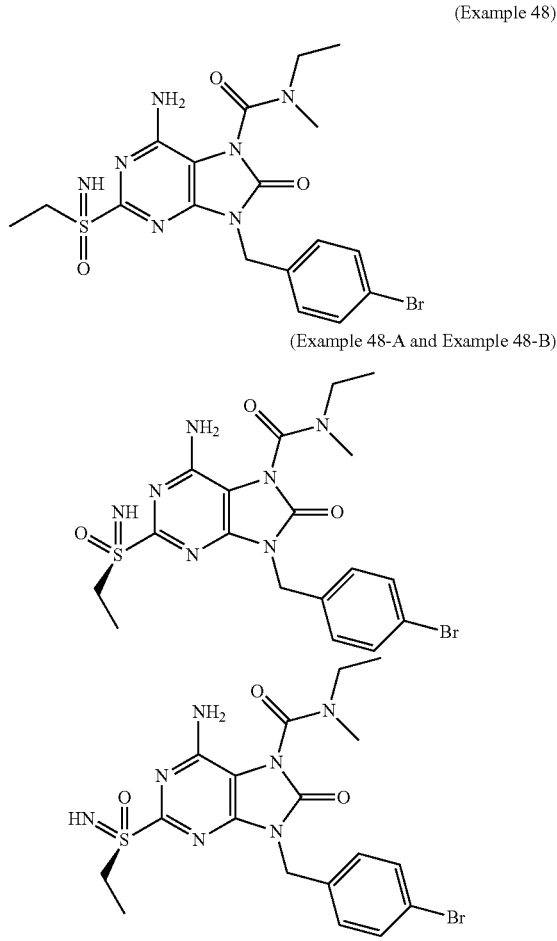

(Example 48)

(Example 48-A and Example 48-B)

Example 48 was prepared in analogy to Example 1, Method A, Step 6 by using 6-amino-9-[(4-bromophenyl)methyl]-2-(ethylsulfonimidoyl)-7H-purin-8-one (Compound 47e) and N-ethyl-N-methyl-carbamoyl chloride instead of 6-amino-9-benzyl-2-(propyl sulfonimidoyl)-7H-purin-8-one (Compound 1e) and N-methyl-N-propyl-carbamoyl chloride (Intermediate AA). 6-Amino-9-[(4-bromophenyl)methyl]-2-(ethylsulfonimidoyl)-N-methyl-8-oxo-N-propyl-purine-7-carboxamide (469 mg, Example 48) was obtained as a white solid. $^1$H NMR (400 MHz, DMSO-$d_6$) δ ppm: 7.56-7.54 (d, J=8.0 Hz, 2H), 7.36-7.34 (d, J=8.0 Hz, 2H), 6.98 (br. s., 2H), 4.97 (s, 2H), 3.53-3.46 (m, 4H), 3.05-3.01 (m, 3H), 1.22-1.16 (m, 6H). MS obsd. (ESI$^+$) [(M+H)$^+$]: 496.

Separation of compound of Example 48 by chiral HPLC afforded Example 48-A (faster eluting, 198 mg) and Example 48-B (slower eluting, 202 mg) as white solid with methanol 5%-40% (0.05% DEA)/CO$_2$ on ChiralPak AD-3 column.

Example 48-A: $^1$H NMR (400 MHz, DMSO-$d_6$) δ ppm: 7.56-7.54 (d, J=8.0 Hz, 2H), 7.36-7.34 (d, J=8.0 Hz, 2H), 6.92 (br. s., 2H), 4.97 (s, 2H), 4.19-4.18 (m, 1H), 3.46-3.41 (m, 4H), 3.05-3.01 (m, 3H), 1.20-1.14 (m, 6H). MS obsd. (ESI$^+$) [(M+H)$^+$]: 496.

Example 48-B: $^1$H NMR (400 MHz, DMSO-$d_6$) δ ppm: 7.56-7.54 (d, J=8.0 Hz, 2H), 7.36-7.34 (d, J=8.0 Hz, 2H), 6.92 (br. s., 2H), 4.97 (s, 2H), 4.24 (br. s., 1H), 3.58-3.41 (m, 4H), 3.05-3.01 (m, 3H), 1.26-1.01 (m, 6H). MS obsd. (ESI$^+$) [(M+H)$^+$]: 496.

Example 49

Activity of Compounds and Examples in HEK293-hTLR-7 Assay

HEK293-Blue-hTLR-7 Cells Assay:

A stable HEK293-Blue-hTLR-7 cell line was purchased from InvivoGen (Cat.#: hkb-htlr7, San Diego, Calif., USA). These cells were designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was regulated by the NF-κB promoter upon stimulation of human TLR7 for 20 hrs. The cell culture supernatant SEAP reporter activity was determined using QUANTI-Blue™ kit (Cat.#: rep-qbl, Invivogen, San Diego, Calif., USA) at a wavelength of 640 nm, a detection medium that turns purple or blue in the presence of alkaline phosphatase.

HEK293-Blue-hTLR7 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (V/V) heat-inactivated fetal bovine serum for 24 hrs. Then the HEK293-Blue-hTLR-7 cells were incubated with addition of 20 μL test compound in a serial dilution in the presence of final DMSO at 1% and perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620~655 nm using a spectrophotometer. The signalling pathway that TLR7 activation leads to downstream NF-κB activation has been widely accepted, and therefore similar reporter assay was also widely used for evaluating TLR7 agonist (Tsuneyasu Kaisho and Takashi Tanaka, Trends in Immunology, Volume 29, Issue 7, July 2008, Pages 329.sci; Hiroaki Hemmi et al, Nature Immunology 3, 196-200 (2002)).

The Compounds and Examples of the present invention were tested in HEK293-hTLR-7 assay for their TLR7 agonism activity as described herein and results are listed in Table 1. The Examples of prodrugs were found to have EC$_{50}$ of about 2.1 μM to about 1000 μM, the Compounds of active forms were found to have EC$_{50}$ less than 0.2 μM. The calculated ratio of EC$_{50(prodrug)}$/EC$_{50(active\ form)}$ were within the range from 32 to about 7600.

TABLE 1

Activity of Examples and Compounds of present invention in HEK293-hTLR-7 assay

| Prodrug | HEK293-hTLR-7 EC$_{50}$ (Prodrug, μM) | Corresponding Active Form | HEK293-hTLR-7 EC$_{50}$ (Active form, μM) | Ratio (EC$_{50(prodrug)}$/EC$_{50(active form)}$) |
|---|---|---|---|---|
| Example 1 | 50.4 | Compound 1e | 0.065 | 775.4 |
| Example 1-A | 42.5 | Compound 1e-A | 0.067 | 634.3 |
| Example 1-B | 27 | Compound 1e-B | 0.086 | 314.0 |
| Example 2 | 32 | Compound 1e | 0.065 | 372.1 |
| Example 2-A | 3.7 | Compound 1e-B | 0.086 | 43.0 |
| Example 2-B | 4.4 | Compound 1e-A | 0.067 | 65.7 |
| Example 3 | 15.1 | Compound 1e | 0.065 | 232.3 |
| Example 4 | 23 | Compound 1e | 0.065 | 353.8 |
| Example 5 | 41 | Compound 1e | 0.065 | 630.8 |
| Example 6 | 82.3 | Compound 1e | 0.065 | 1266.2 |
| Example 7 | 19.9 | Compound 1e | 0.065 | 306.2 |
| Example 8 | 2.1 | Compound 1e | 0.065 | 32.3 |
| Example 9 | 19.2 | Compound 1e | 0.065 | 295.4 |
| Example 10 | 68.5 | Compound 1e | 0.065 | 1053.8 |
| Example 11 | 5.6 | Compound 1e | 0.065 | 86.2 |
| Example 12 | 43.9 | Compound 1e | 0.065 | 675.4 |
| Example 13 | 67 | Compound 1e | 0.065 | 1030.8 |
| Example 14 | 2.4 | Compound 1e | 0.065 | 36.9 |
| Example 15 | 494 | Compound 1e | 0.065 | 7600 |
| Example 16 | 32.1 | Compound 1e | 0.065 | 493.8 |
| Example 25 | 24.2 | Compound 1e | 0.065 | 372.3 |
| Example 26 | 13.4 | Compound 1e | 0.065 | 206.2 |
| Example 27 | 31.7 | Compound 1e | 0.065 | 487.7 |
| Example 28 | 6.9 | Compound 1e | 0.065 | 106.2 |
| Example 29 | 48.8 | Compound 1e | 0.065 | 750.8 |
| Example 32 | 22.5 | Compound 1e | 0.065 | 346.2 |
| Example 34-A | 6.0 | Compound 34e-A | 0.014 | 428.6 |
| Example 34-B | 6.36 | Compound 34e-B | 0.011 | 578.2 |
| Example 36-A | 31.8 | Compound 36g-A | 0.019 | 1673.7 |
| Example 37-A | 26.6 | Compound 36g-A | 0.019 | 1400 |
| Example 37-B | 47.4 | Compound 36g-B | 0.022 | 2154.5 |
| Example 38-A | 26.2 | Compound 36g-A | 0.019 | 1378.9 |
| Example 38-B | 19.5 | Compound 36g-B | 0.022 | 886.4 |
| Example 39 | 4.3 | Compound 36g | 0.027 | 159.3 |
| Example 40 | 52.8 | Compound 36g | 0.027 | 1955.6 |
| Example 41 | 36 | Compound 41c | 0.053 | 679.2 |
| Example 41-A | 44.1 | Compound 41c-B | 0.085 | 518.8 |
| Example 41-B | 32.1 | Compound 41c-A | 0.071 | 452.1 |
| Example 42-A | 40.5 | Compound 41c-A | 0.071 | 570.4 |
| Example 42-B | 49.2 | Compound 41c-B | 0.085 | 578.8 |
| Example 43-A | 110 | Compound 43e-A | 0.11 | 1000 |
| Example 43-B | 78.4 | Compound 43e-B | 0.035 | 2240 |
| Example 44-A | 65.4 | Compound 43e-B | 0.035 | 1868.6 |
| Example 44-B | 96.7 | Compound 43e-A | 0.11 | 879.1 |
| Example 45-A | 153 | Compound 45e-B or Compound 45e-A | 0.26 or 0.39 | 588 or 392 |
| Example 45-B | >1000 | Compound 45e-B or Compound 45e-A | 0.26 or 0.39 | >3846 or >2564 |
| Example 46-A | 45.5 | Compound 45e-A or Compound 45e-B | 0.26 or 0.39 | 175 or 116.7 |
| Example 46-B | 45.7 | Compound 45e-B or Compound 45e-A | 0.26 or 0.39 | 175.7 or 117.2 |
| Example 47-A | 10.9 | Compound 47e-A or Compound 47e-B | 0.021 or 0.025 | 519.0 or 436 |
| Example 47-B | 13.1 | Compound 47e-A or Compound 47e-B | 0.021 or 0.025 | 623.8 or 524 |
| Example 48-A | 18.3 | Compound 47e-A or Compound 47e-B | 0.021 or 0.025 | 871.4 or 732 |
| Example 48-B | 20.8 | Compound 47e-A or Compound 47e-B | 0.021 or 0.025 | 990.5 or 832 |

Example 50

Metabolism of Prodrugs of Compound of Formula (I)

A study was undertaken to evaluate the metabolic conversion of prodrugs, compound of formula (I), to its corresponding active form. The compounds of formula (I), if served as prodrugs, can be metabolized to the active compound or other compounds of the invention in the body. Human liver microsomes are often used to assess the degree of metabolic conversion of prodrugs in the body of animal or human.

Materials

NADPH cofactor system including β-Nicotinamide adenine dinucleotide phosphate (NADP), isocitric acid and isocitric dehydrogenase were purchased from Sigma-Aldrich Co. (St. Louis, Mo., USA). Human liver microsomes (Cat No. 452117, Lot No. 38290) were obtained from Corning (Woburn, Mass., USA). Mouse liver microsomes (Cat No. M1000, Lot No. 1310028) were obtained from Xenotech.

Working Solution of the Compounds and Other Solution

Compounds were dissolved in DMSO to make 10 mM stock solutions. 10 μL of the stock solution was diluted with acetonitrile (990 μL) to get a 100 μM working solution.

Incubation

Microsomes were preincubated with test compound for 10 min at 37° C. in 100 mM potassium phosphate buffer with pH 7.4. The reactions were initiated by adding NADPH regenerating system to give a final incubation volume of 200 μL and shaken in a water bath at 37° C. Incubation mixtures consisted of liver microsomes (0.5 mg microsomal protein/mL), substrates (1.0 μM), and NADP (1 mM), isocitric dehydrogenase (1 unit/mL), isocitric acid (6 mM).

Preparation of Samples for Analysis

At 30 min, reaction was quenched by adding 600 μL cold acetonitrile (including 100 ng/mL tolbutamide and 100 ng/mL labetalol as internal standard). The samples were centrifuged at 4000 rpm for 20 minutes and the resultant supernatants were subjected to LC-MS/MS analysis.

The samples for calibration curve were prepared as followed. Dispense 100 μL/well liver microsomes and 98 μL/well NADPH regenerating system solution to 96-well plate. Add 600 μL quenching solution first, and then followed by 2 μL Standard curve and QC working solution.

Bioanalysis

The compounds were quantified on an API4000 LC-MC/MC instrument in the ESI-Positive MRM mode.

A study was undertaken to evaluate the metabolic conversion of prodrugs (1 μM), Example 1, Example 1-A, Example 1-B, Example 2, Example 2-A, Example 2-B, Example 3, Example 4, Example 5, Example 6, Example 7, Example 8, Example 9, Example 10, Example 11, Example 12, Example 13, Example 14, Example 15, Example 16, Example 17, Example 21, Example 22, Example 23, Example 25, Example 26, Example 27, Example 28 Example 29, Example 30, Example 31, Example 32, Example 33, Example 34-A, Example 34-B, Example 36-A, Example 36-B, Example 37-A, Example 37-B, Example 38-A, Example 38-B, Example 39, Example 40, Example 41, Example 41-A, Example 41-B, Example 42, Example 42-A, Example 42-B, Example 43, Example 43-A, Example 43-B, Example 44, Example 44-A, Example 44-B and Example 45-A, Example 46-A, Example 46-B, Example 47-A, Example 47-B, Example 48-A, Example 48-B to the corresponding active forms, Compound 1e, Compound 1e-A, Compound 1e-B, Compound 34e-A, Compound 34e-B, Compound 36g-A, Compound 36g-B, Compound 36g, Compound 41c, Compound 41c-B, Compound 41c-A, Compound 43e, Compound 43e-A, Compound 43e-B, Compound 45e-A, Compound 45e-B, Compound 47e-A, and Compound 47e-B in the presence of human liver microsomes. Results were summarized and shown in Table 2.

TABLE 2

Metabolic conversion of prodrugs in human liver microsomes

| Example No. | Corresponding Metabolized Product (active form) | Metabolized product concentration in human liver microsomes (μM) |
| --- | --- | --- |
| Example 1 | Compound 1e | 0.0214 |
| Example 1-A | Compound 1e-A | 0.018 |
| Example 1-B | Compound 1e-B | 0.022 |
| Example 2 | Compound 1e | 0.028 |
| Example 2-A | Compound 1e-B | 0.036 |
| Example 2-B | Compound 1e-A | 0.029 |
| Example 3 | Compound 1e | 0.12 |
| Example 5 | Compound 1e | 0.078 |
| Example 6 | Compound 1e | 0.074 |
| Example 7 | Compound 1e | 0.15 |
| Example 8 | Compound 1e | 0.043 |
| Example 9 | Compound 1e | 0.002 |
| Example 10 | Compound 1e | 0.005 |
| Example 11 | Compound 1e | 0.001 |
| Example 12 | Compound 1e | 0.018 |
| Example 13 | Compound 1e | 0.04 |
| Example 14 | Compound 1e | 0.026 |
| Example 15 | Compound 1e | 0.002 |
| Example 16 | Compound 1e | 0.024 |
| Example 17 | Compound 1e | 0.075 |
| Example 21 | Compound 1e | 0.48 |
| Example 22 | Compound 1e | 0.42 |
| Example 23 | Compound 1e | 0.42 |
| Example 25 | Compound 1e | 0.018 |
| Example 26 | Compound 1e | 0.042 |
| Example 27 | Compound 1e | 0.11 |
| Example 28 | Compound 1e | 0.084 |
| Example 29 | Compound 1e | 0.009 |
| Example 31 | Compound 1e | 0.005 |
| Example 32 | Compound 1e | 0.013 |
| Example 33 | Compound 1e | 0.59 |
| Example 34-A | Compound 34e-A | 0.2 |
| Example 34-B | Compound 34e-B | 0.088 |
| Example 36-A | Compound 36g-A | 0.02 |
| Example 36-B | Compound 36g-B | 0.019 |
| Example 37-A | Compound 36g-A | 0.004 |
| Example 37-B | Compound 36g-B | 0.002 |
| Example 38-A | Compound 36g-A | 0.026 |
| Example 38-B | Compound 36g-B | 0.034 |
| Example 40 | Compound 36g | 0.032 |
| Example 41-A | Compound 41c-B | 0.38 |
| Example 41-B | Compound 41c-A | 0.36 |
| Example 42-A | Compound 41c-A | 0.14 |
| Example 42-B | Compound 41c-B | 0.004 |
| Example 43-A | Compound 43e-A | 0.014 |
| Example 43-B | Compound 43e-B | 0.016 |
| Example 44-A | Compound 43e-B | 0.002 |
| Example 44-B | Compound 43e-A | 0.002 |
| Example 45-A | Compound 45e-B or Compound 45e-A | 0.41 |
| Example 46-A | Compound 45e-A or Compound 45e-B | 0.039 |
| Example 46-B | Compound 45e-B or Compound 45e-A | 0.18 |
| Example 47-A | Compound 47e-A or Compound 47e-B | 0.36 |
| Example 47-B | Compound 47e-B or Compound 47e-A | 0.41 |
| Example 48-A | Compound 47e-A or Compound 47e-B | 0.11 |
| Example 48-B | Compound 47e-B or Compound 47e-A | 0.053 |

Example 51

In Vivo Antiviral Efficacy of Example 43-A in AAV-HBV Mouse Model

Animal Model 4-6 week old male C57BL/6 mice, specific pathogen free, were purchased from Shanghai Laboratory Animal Center of Chinese Academy of Sciences (SLAC) and housed in an animal care facility in individually ventilated cages under controlled temperature and light conditions following the Institutional Animal Care guidelines. AAV-HBV virus was purchased from Beijing FivePlus Molecular Medicine Institute (Beijing, China). The recombinant virus carries 1.3 copies of the HBV genome packaged into AAV serotype 8 (AAV8) capsids. C57BL/6 mice were injected with 200 μL of the recombinant virus diluted in saline buffer through tail vein. On day 14, the mice were bled to measure HBV surface antigen (HBsAg) and HBV genomic DNA in the serum, and animals were then randomized into groups according to these HBV biomarkers.

Measurement of HBV Biomarkers

Serum HBsAg and HBeAg were measured using CLIA kits (Autobio Diagnostics Co., Ltd., Zhengzhou, China) according to the manufacturer's instructions. The lower limit of detection for HBsAg was 0.05 IU/mL. Serum dilution of 500-fold was used to obtain values within the linear range of the standard curve.

Serum HBV DNA was extracted using a MagNA Pure 96 DNA and Viral NA Small Volume Kit (Roche) following the manufacturer's instructions. The DNA samples were analyzed by real-time quantitative PCR (qPCR) using a HBV-specific primer and probe set for specific amplification and detection of a 128 bp HBV genome region from the nucleotide 2969 to 3096. The sequences of the primers and probe are:

```
Forward primer:
AAGAAAAACCCCGCCTGTAA;

Reverse primer:
CCTGTTCTGACTACTGCCTCTCC;

HBV-Probe:
5'TAMRA-CCTGATGTGATGTTCTCCATGTTCAGC-BHQ2-3'.
```

Anti-HBs in the serum was tested using Anti-HBs CLIA kits (Autobio Diagnostics Co., Ltd., Zhengzhou, China) and mouse anti-IgG conjugated with Biotin (0.5 mg/mL) from a Mabtech B Elispot kit. The anti-IgG Biotin was diluted in PBS with a final concentration of 1 μg/mL. 25 μL of mouse anti-IgG were mixed with serum samples in wells of the plate in the Anti-HBs CLIA kit for 1-hour incubation. Then wash the plate and add Streptavidin-HRP for 1-hour incubation at room temperature. After repeating the washing step, mix substrate A and B from the CLIA kit and add 50 μL of the mixture in each well. After 5-min incubation at room temperature, the plate was read on an Envision Plate Reader (PerkinElmer) to measure luminecence.

Study Design and Results

The mouse model with high level expression of both HBV DNA and HBsAg was generated by injecting C57BL/6 mice with a recombinant adeno-associated virus (AAV) carrying a replicable HBV genome (AAV-HBV). With long-lasting HBV viremia and fully competent immune system, the AAV-HBV mouse model was utilized to evaluate the antiviral efficacy of the TLR7 agonists following the study design as shown in Table 3.

TABLE 3

In vivo efficacy test of Example 43-A in AAV-HBV mouse model

| Animal group | Test article | Dose (mg/kg) | Route | Frequency | Treatment |
|---|---|---|---|---|---|
| 1 | Vehicle | 0 | PO | QOD | 42 days |
| 2 | Example | 10 | PO | QOD | 42 days |
| 3 | 43-A | 10 | PO | QW | 42 days |

Specifically, groups 2 and 3 were orally dosed with Example 43-A at 10 mg/kg every other day (QOD) and once weekly (QW), respectively, and the control group 1 received only Vehicle. At the dosing volume of 10 mL/kg, Example 43-A (1 mg/mL) was formulated as an inclusion complex with 2% Klucel LF, 0.5% TPGS, 0.09% Methylparabens, 0.01% Propylparabens in water. The animals were treated for a total of 42 days, and were submandibularly bled twice per week for serum collection throughout the study. The serum samples were subjected to analysis of HBV biomarkers.

Figure 4:
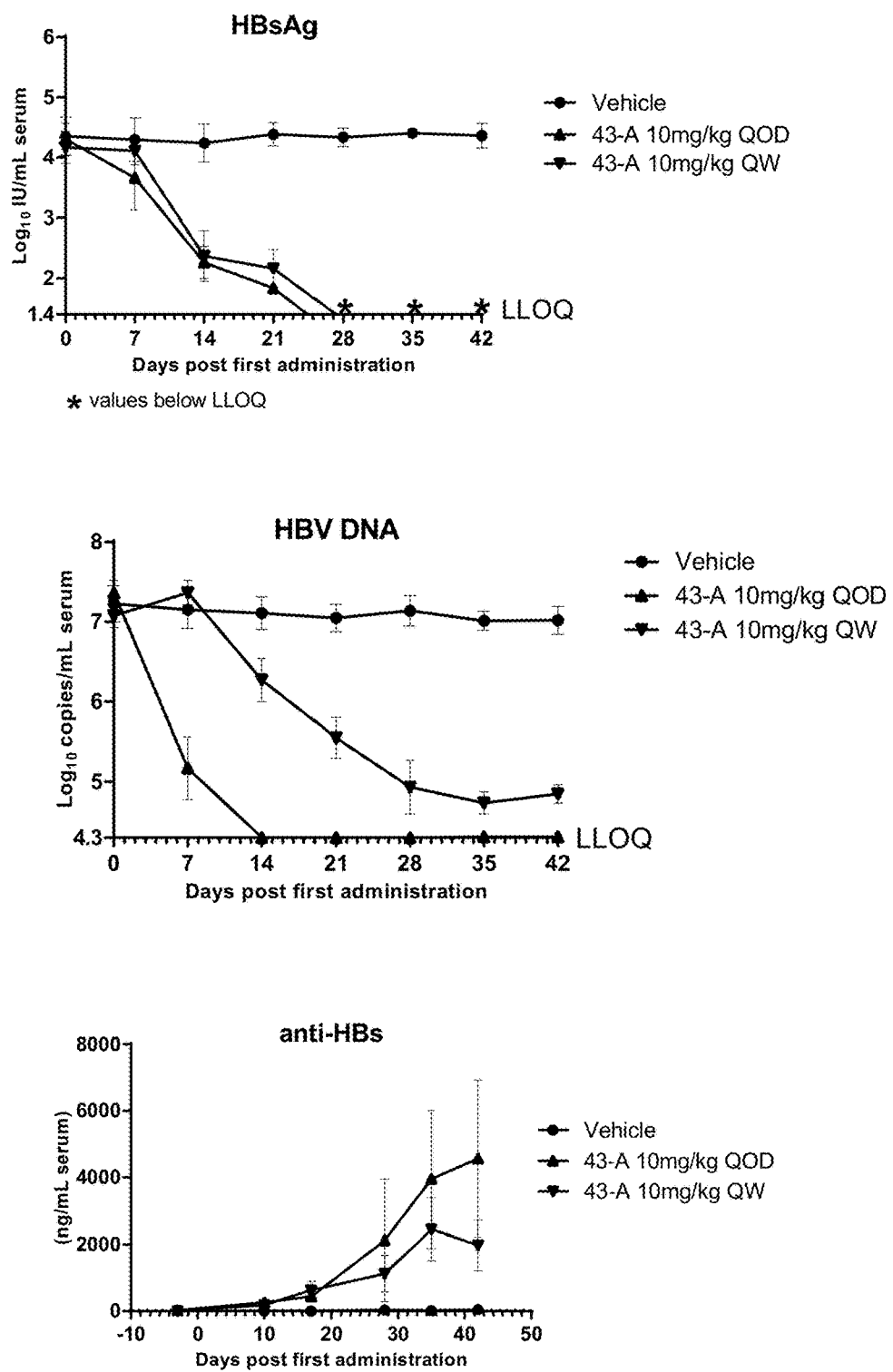
FIG. 4 shows the HBV DNA, HBsAg, and anti-HBs antibody level of the AAV-HBV infected mice treated with Vehicle, Example 43-A at 10 mg/kg QOD and QW for 42 days. The results are presented as mean±SEM. LLOQ: lower limit of quantification.

As shown in FIG. 4, the treatment of Example 43-A at 10 mg/kg QOD resulted in a dramatic reduction in HBV DNA (>3 log) and HBsAg (>2.8 log). At the end of the 42-day treatment, the levels of these viral markers became undetectable and below the lower limit of quantification (LLOQ). Even with the less frequent QW dosing, Example 43-A significantly reduced both HBV DNA (>2 log) and HBsAg (>2.8 log). Moreover, the treatment of Example 43-A at 10 mg/kg, regardless of QOD and QW dosing, induced a considerable level of anti-HBsAg antibody. In conclusion, Example 43-A demonstrated good in vivo anti-HBV activity by reducing HBV viral markers and promoting the production of HBV-specific antibody.

Example 52

In Vivo Antiviral Efficacy of Example 41-A in AAV-HBV Mouse Model

The antiviral efficacy of Example 41-A was evaluated in the same AAV-HBV model following the study design in Table 4 with the same methods to measure HBV biomarkers as described in Example 51.

TABLE 4

In vivo efficacy test of Example 41-A in AAV-HBV mouse model

| Animal group | Test article | Dose (mg/kg) | Route | Frequency | Treatment |
|---|---|---|---|---|---|
| 1 | Vehicle | 0 | PO | QOD | 42 days |
| 2 | Example 41-A | 1 | PO | QOD | 42 days |
| 3 | | 3 | PO | QOD | 42 days |
| 4 | | 10 | PO | QOD | 42 days |
| 5 | | 10 | PO | QW | 42 days |

Specifically, groups 2, 3 and 4 were orally dosed with Example 41-A at 1, 3 and 10 mg/kg QOD respectively. Group 5 was treated with 10 mg/kg QW, while group 1 with only Vehicle. At the dosing volume of 10 mL/kg, Example 41-A (0.1, 0.3, and 1 mg/mL) was formulated as an inclusion complex with 2% Klucel LF, 0.5% TPGS, 0.09% Methylparabens, 0.01% Propylparabens in water. The animals were treated for a total of 42 days, and were submandibularly bled twice per week for serum collection throughout the study. The serum samples were subjected to analysis of HBV biomarkers.

Figure 5:
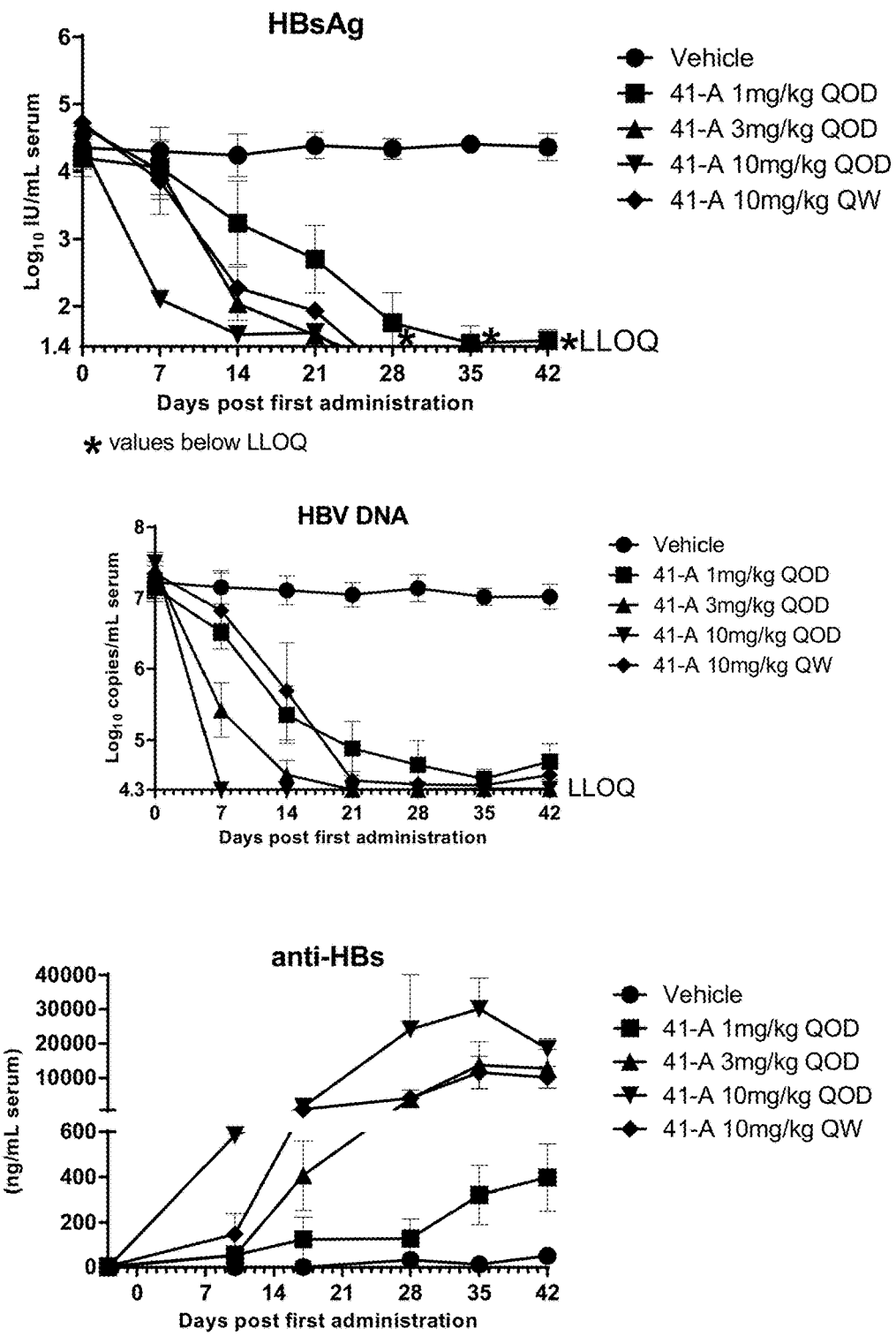
FIG. 5 shows the HBV DNA, HBsAg, and anti-HBs antibody levels of AAV-HBV infected mice treated with Vehicle, Example 41-A at 1, 3, 10 mg/kg QOD, and 10 mg/kg QW for 42 days. The results are presented as mean±SEM. LLOQ: lower limit of quantification.

As shown in FIG. 5, the treatment of Example 41-A at 1, 3, 10 mg/kg QOD dose-dependently reduced HBV DNA and HBsAg. All three doses managed to reduce these viral markers below or close to the LLOQ at the end of the 42-day treatment. Even with the less frequent QW dosing, Example 41-A at 10 mg/kg also reduced HBV DNA and HBsAg to undetectable levels at the treatment end. Moreover, Example 41-A induced significantly higher levels of antibody against-HbsAg than Vehicle post treatment. In conclusion, Example 41-A demonstrated good in vivo anti-HBV activity by reducing HBV viral markers and promoting the production of HBV-specific antibody.

Example 53

In Vivo Antiviral of Example 42-A Efficacy in AAV-HBV Mouse Model

The antiviral efficacy of Example 42-A was evaluated in the same AAV-HBV model following the study design in Table 5 with the same methods to measure HBV biomarkers as described in Example 51.

TABLE 5

In vivo efficacy test of Example 42-A in AAV-HBV mouse model

| Animal group | Test article | Dose (mg/kg) | Route | Frequency | Treatment |
|---|---|---|---|---|---|
| 1 | Vehicle | 0 | PO | QOD | 42 days |
| 2 | Example 42-A | 1 | PO | QOD | 42 days |
| 3 |  | 3 | PO | QOD | 42 days |
| 4 |  | 10 | PO | QOD | 42 days |

Specifically, groups 2, 3, and 4 were orally dosed with Example 42-A at 1, 3, and 10 mg/kg QOD respectively, while group 1 with only Vehicle. At the dosing volume of 10 mL/kg, Example 42-A (0.1, 0.3, and 1 mg/mL) was formulated as an inclusion complex with 2% Klucel LF, 0.5% TPGS, 0.09% Methylparabens, 0.01% Propylparabens in water. The animals were treated for a total of 42 days, and were submandibularly bled twice per week for serum collection throughout the study. The serum samples were subjected to analysis of HBV biomarkers.

Figure 6:
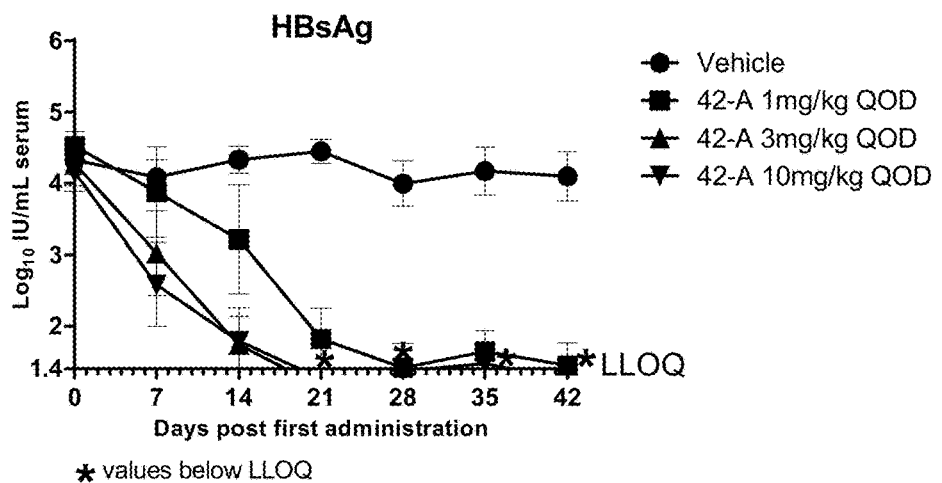
FIG. 6 shows the HBV DNA, HBsAg, and anti-HBs antibody levels of AAV-HBV infected mice treated with Vehicle, Example 42-A at 1, 3, and 10 mg/kg QOD for 42 days. The results are presented as mean±SEM. LLOQ: lower limit of quantification.
Figure 6:
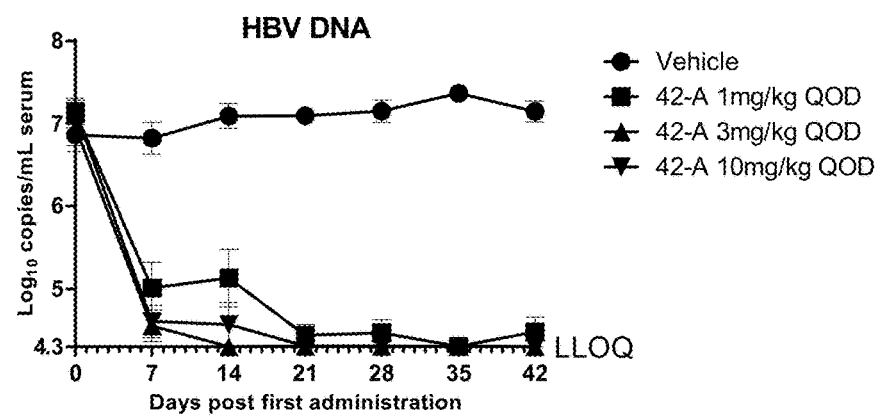
Figure 6:
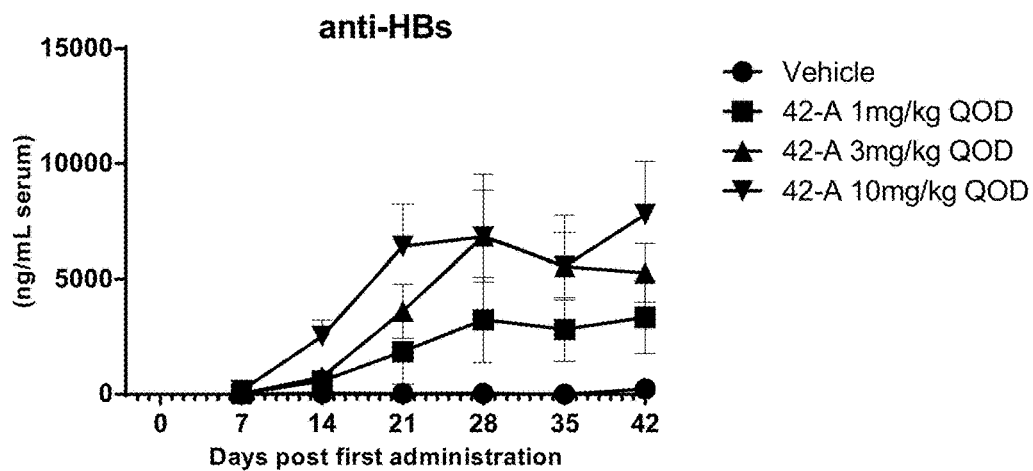

As shown in FIG. 6, the treatment of Example 42-A at 1, 3, 10 mg/kg QOD were all effective to reduce HBV DNA and HBsAg. While the higher doses led to faster clearance of HBV DNA and HBsAg, all three doses managed to reduce these viral markers below or close to the LLOQ at the end of the 42-day treatment. All the groups treated with Example 42-A developed significantly higher levels of anti-HBsAg antibody. In conclusion, Example 42-A demonstrated good in vivo anti-HBV activity by reducing HBV viral markers and promoting the production of HBV-specific antibody.

Example 54

In Vivo Antiviral Efficacy of Example 41-B in AAV-HBV Mouse Model

The antiviral efficacy of Example 41-B was evaluated in the same AAV-HBV model following the study design in Table 6 with the same methods to measure HBV biomarkers as described in Example 51.

TABLE 6

In vivo efficacy test of Example 41-B in AAV-HBV mouse model

| Animal group | Test article | Dose (mg/kg) | Route | Frequency | Treatment |
|---|---|---|---|---|---|
| 1 | Vehicle | 0 | PO | QOD | 42 days |
| 2 | Example 41-B | 1 | PO | QOD | 42 days |
| 3 |  | 3 | PO | QOD | 42 days |
| 4 |  | 10 | PO | QOD | 42 days |

Specifically, groups 2, 3, and 4 were orally dosed with Example 41-B at 1, 3, and 10 mg/kg QOD, respectively, while group 1 with only Vehicle. At the dosing volume of 10 mL/kg, Example 41-B (0.1, 0.3, and 1 mg/mL) was formulated as an inclusion complex with 2% Klucel LF, 0.5% TPGS, 0.09% Methylparabens, 0.01% Propylparabens in water. The animals were treated for a total of 42 days, and were submandibularly bled twice per week for serum collection throughout the study. The serum samples were subjected to analysis of HBV biomarkers.

Figure 7:
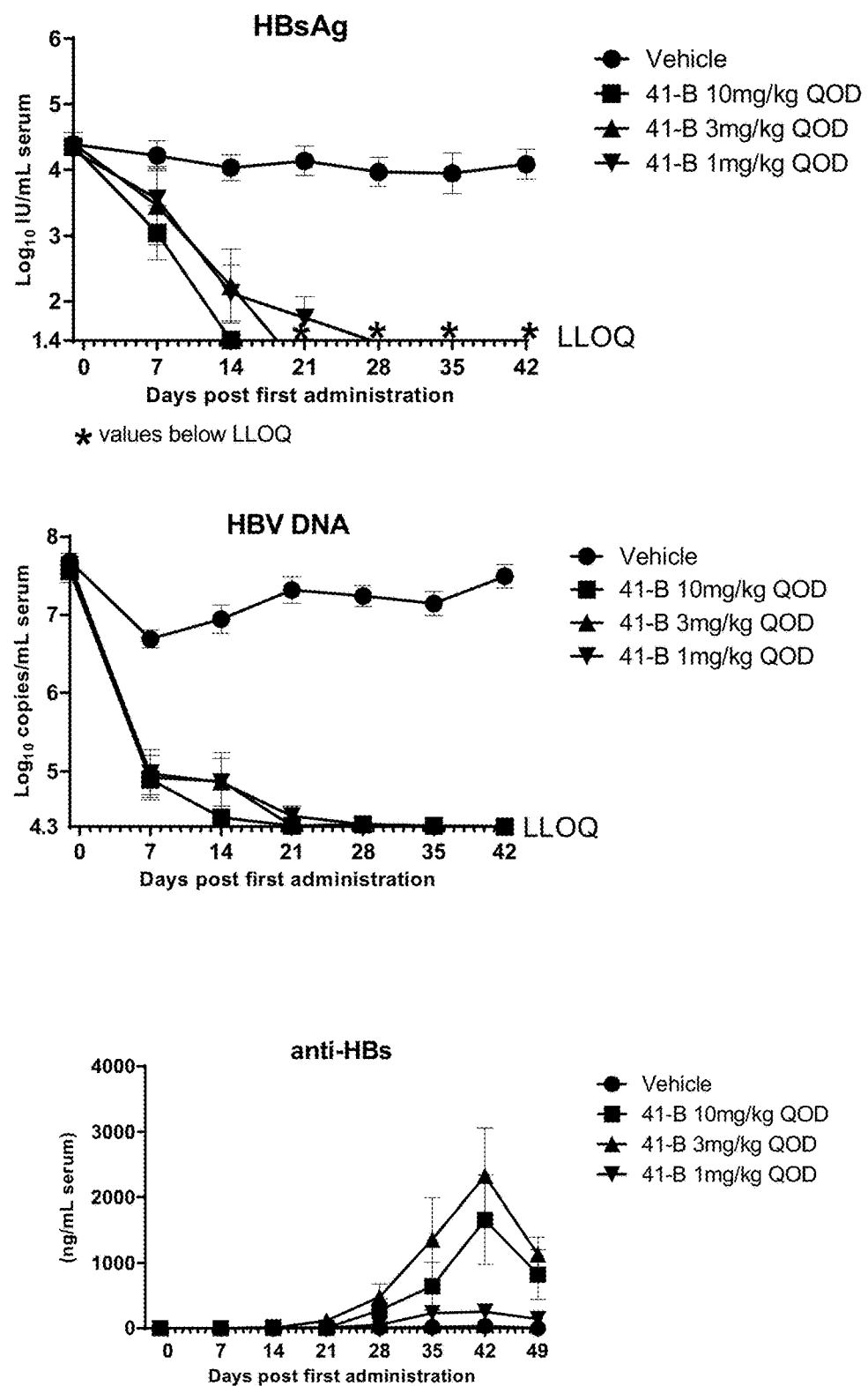
FIG. 7 shows the HBV DNA, HBsAg, and anti-HBs antibody levels of AAV-HBV infected mice treated with Vehicle, Example 41-B at 1, 3, and 10 mg/kg QOD for 42 days. The results are presented as mean±SEM. LLOQ: lower limit of quantification.

As shown in FIG. 7, the treatment of Example 41-B at 1, 3, 10 mg/kg QOD were all effective to reduce HBV DNA and HBsAg. All three doses managed to reduce these viral markers below the LLOQ at the end of the 42-day treatment. All the groups treated with Example 41-B also developed high levels of anti-HBsAg antibody than the Vehicle group. In conclusion, Example 41-B demonstrated in vivo anti-HBV activity by reducing HBV viral markers and promoting the production of HBV-specific antibody.

Example 55

Single Dose PK Study in Male Wister-Han Rats

The single dose PK in Male Wister-Han Rats was performed to assess pharmacokinetic properties of tested compounds. Two groups of animals were dosed via Gavage (POE) of the respective compound. Blood samples (approximately 20 μL) were collected via Jugular vein or an alternate site at 15 min, 30 min, 1 H, 2 h, 4 h, 7 h and 24 h post-dose groups. Blood samples were placed into tubes containing EDTA-K2 anticoagulant and centrifuged at 5000 rpm for 6 min at 4° C. to separate plasma from the samples. After centrifugation, the resulting plasma was transferred to clean tubes for bioanalysis of both prodrug and active form on LC/MS/MS. In the groups that prodrug were dosed, the concentration of prodrugs in the plasma samples was under the detection limit. The "tested compound" in Table 8 was used as the internal standard for testing the metabolite (active form) of "dose compound" in vivo. The pharmacokinetic parameters were calculated using non-compartmental module of WinNonlin® Professional 6.2. The peak concentration ($C_{max}$) was recorded directly from experimental observations. The area under the plasma concentration-time curve ($AUC_{0-t}$) was calculated using the linear trapezoidal rule up to the last detectable concentration.

$C_{max}$ and $AUC_{0-last}$ are two critical PK parameters related to the in vivo efficacy of the tested compound. Compounds with higher $C_{max}$ and $AUC_{0-last}$ will lead to the better in vivo efficacy. Results of PK parameters following oral administration of active forms and competitor compounds are given in Table 7. The PK parameters of prodrugs are tabulated in Table 8.

Following oral administration of prodrugs, the active forms were observed in plasma and therefore tested. The exemplified prodrugs of present invention (Example 41-B, 42-A, 42-B, 43-A, 45-A and 45-B) surprisingly showed much improved $C_{max}$ (5-175 folds increase) and $AUC_{0-last}$ (2.5-56 folds increase) comparing with reference compounds (GS9620, S-2 and S-3) and compounds mentioned in present invention (Compound 41c-A, 41c-B and 43e-A) which are all active forms. The results clearly demonstrated the unexpected superiority of prodrugs over active forms on PK parameters which led to better in vivo efficacy.

TABLE 7

The mean plasma concentration and PK parameters of active forms after 5 mg/kg oral dosing

| Time (h) | Dose compound | | | |
|---|---|---|---|---|
| | GS9620 | S-2 | S-3 | Compound 41c-A |
| | Mean plasma concentration (nM) | | | |
| 0.25 | 56.3 | 9.49 | 8.89 | 16.75 |
| 0.5 | 33.2 | 16.74 | 9.99 | 27.48 |
| 1 | 83.4 | 19.33 | 10.16 | 32.33 |
| 2 | 136 | 24.89 | 8.40 | 27.34 |
| 4 | 16.7 | 47.55 | 11.54 | 27.38 |
| 8* | 9.49 | 52.72 | 8.17 | 18.02 |
| 24 | ND | 4.90 | ND | 5.60 |
| $C_{max}$ (nM) | 164 | 52.72 | 11.54 | 32.33 |
| $AUC_{0-last}$ (nM · h) | 316 | 748 | 95 | 242.5 |

| Time (h) | Dose compound | | | |
|---|---|---|---|---|
| | Compound 41c-B | Compound 43e-A | Compound 45e-A | Compound 45e-B |
| | Mean plasma concentration (nM) | | | |
| 0.25 | 3.41 | 12.60 | 64.6 | 42.8 |
| 0.5 | 0.75 | 15.22 | 80.0 | 52.2 |
| 1 | 2.04 | 13.01 | 58.1 | 37.6 |
| 2 | 5.46 | 11.98 | 42.5 | 24.2 |
| 4 | 2.52 | 8.20 | 77.8 | 53.9 |
| 8* | 1.21 | 6.31 | 34.6 | 29 |
| 24 | ND | ND | 8.6 | 5.7 |
| $C_{max}$ (nM) | 5.46 | 15.22 | 80.0 | 53.9 |
| $AUC_{0-last}$ (nM · h) | 55.8 | 77 | 767 | 568 |

*7 hrs for Compound 41c-A, Compound 41c-B and Compound 43e-A

TABLE 8

PK parameters of prodrugs after 5 mg/kg oral dosing

| Dose compound | Tested compound | $C_{max}$ (nM) | $AUC_{0-last}$ (nM · h) |
|---|---|---|---|
| Example 41-B | Compound 41c-A | 1315 | 3658 |
| Example 42-A | Compound 41c-A | 1742 | 4867 |
| Example 42-B | Compound 41c-B | 956 | 3148 |
| Example 43-A | Compound 43e-A | 77 | 229 |
| Example 45-A | Compound 45e-B | 922 | 1914 |
| Example 45-B | Compound 45e-A | 1436 | 2619 |

Example 56

LYSA Solubility Study

LYSA study is used to determine the aqueous solubility of tested compounds. Samples were prepared in duplicate from 10 mM DMSO stock solution. After evaporation of DMSO with a centrifugal vacuum evaporator, the compounds were dissolved in 0.05M phosphate buffer (pH 6.5), stirred for one hour and shaken for two hours. After one night, the solutions were filtered using a microtiter filter plate. Then the filtrate and its 1/10 dilution were analyzed by HPLC-UV. In addition, a four-point calibration curve was prepared from the 10 mM stock solutions and used for the solubility determination of the compounds. The results were in μg/mL. In case the percentage of sample measured in solution after evaporation divided by the calculated maximum of sample amount was bigger than 80%, the solubility was reported as bigger than this value.

Results of LYSA were shown in Table 9. It was clear that the solubility of active forms were surprisingly improved by 10 to over 200 folds when converted to various prodrugs.

TABLE 9

Solubility data of particular compounds

| Prodrugs | LYSA of Prodrugs (μg/mL) | Corresponding Active Forms | LYSA of Active Forms (μg/mL) |
|---|---|---|---|
| Example 1 | 290 | Compound 1e | 21 |
| Example 1-A | 315 | Compound 1e-A | 56 |
| Example 1-B | 200 | Compound 1e-B | 50 |
| Example 2 | 615 | Compound 1e | 21 |
| Example 2-A | >600 | Compound 1e-B | 50 |
| Example 2-B | >590 | Compound 1e-A | 56 |
| Example 3 | 240 | Compound 1e | 21 |
| Example 4 | 695 | Compound 1e | 21 |
| Example 5 | >595 | Compound 1e | 21 |
| Example 6 | 140 | Compound 1e | 21 |
| Example 7 | 615 | Compound 1e | 21 |
| Example 8 | 620 | Compound 1e | 21 |
| Example 9 | >520 | Compound 1e | 21 |
| Example 10 | 120 | Compound 1e | 21 |
| Example 11 | >618 | Compound 1e | 21 |
| Example 12 | 120 | Compound 1e | 21 |
| Example 13 | 155 | Compound 1e | 21 |
| Example 14 | 225 | Compound 1e | 21 |
| Example 15 | 405 | Compound 1e | 21 |
| Example 16 | 205 | Compound 1e | 21 |
| Example 17 | 190 | Compound 1e | 21 |
| Example 25 | >670 | Compound 1e | 21 |
| Example 26 | >690 | Compound 1e | 21 |
| Example 27 | >380 | Compound 1e | 21 |
| Example 28 | 695 | Compound 1e | 21 |
| Example 29 | 395 | Compound 1e | 21 |
| Example 32 | 125 | Compound 1e | 21 |
| Example 36-A | 168 | Compound 36g-A | 6 |
| Example 36-B | 209 | Compound 36g-B | 11 |
| Example 41-A | 260 | Compound 41c-B | 5 |
| Example 41-B | 250 | Compound 41c-A | 1 |
| Example 42-A | 225 | Compound 41c-A | 1 |
| Example 42-B | 335 | Compound 41c-B | 5 |
| Example 43-A | 203 | Compound 43e-A | 13 |
| Example 43-B | 170 | Compound 43e-B | 13 |
| Example 45 | 172 | Compound 45e | 152 |
| Example 45-A | >560 | Compound 45e-A or Compound 45e-B | 90 or 115 |
| Example 45-B | 420 | Compound 45e-B Or Compound 45e-A | 115 or 90 |
| Example 46-A | 205 | Compound 45e-A Or Compound 45e-B | 90 or 115 |
| Example 46-B | >580 | Compound 45e-B Or Compound 45e-A | 115 or 90 |
| Example 47-A | 154 | Compound 47e-A or Compound 47e-B | <1.0 or <1.0 |
| Example 47-B | 128 | Compound 47e-B or Compound 47e-A | <1.0 or <1.0 |
| Example 48-A | 305 | Compound 47e-A or Compound 47e-B | <1.0 or <1.0 |
| Example 48-B | 275 | Compound 47e-B or Compound 47e-A | <1.0 or <1.0 |

Example 57

Portal Vein Study

The objective of this study was to understand whether prodrug remains unchanged as it was absorbed through the intestine into the portal circulation and demonstrate the primary site of conversion.

Surgical Procedure for Portal Vein Cannulation (PVC) and Carotid Artery Cannulation (CAC)

Surgery was performed under pentobarbital/isoflurane anesthesia. Briefly, after disinfecting the abdominal area with betadine and 70% isopropyl alcohol, a small abdominal mid-line incision was made. The cecum was pulled out and mesenteric vein was identified and isolated for about 5 mm vessel. A loose ligature was placed proximally and distal end of the vein was ligated. Make a small incision (just enough to allow the insertion of the catheter) on isolated vein and insert the PU catheter towards liver for appropriate length. The catheter was secured in place by tying the loose ligature around the cannulated vessel. The cecum was replaced into abdominal cavity. A hole was made in the right abdominal wall to make the end of catheter pass freely. The catheter was secured by suture on the abdominal wall. The abdominal muscle incision was closed with suture. A small incision was made in the scapular area to serve as the exit site of the catheter. The catheter was subcutaneously tunneled and exteriorized through the scapular incision. A fixed suture was placed in the scapular region. The patency of the catheter was checked and then exteriorized from the subcutaneous space to the dorsal neck region. After gently wiping the area, the abdominal cavity was sutured. The left carotid artery was then cannulated by inserting a PESO catheter. Both the exteriorized catheters were tied firmly on the dorsal neck region and fixed. The animals was then allowed to recover in its cage and used for study at least 3 days after surgery. All catheters were flushed once daily with heparinized saline to maintain patency.

Oral PK Study in PVC/CAC Dual Cannulated Rat

Animals were fasted overnight (n=3) and administered vial oral gavage (10 mg/kg, 10 mL/kg). Blood samples (60 μL) were collected simultaneously from the portal and carotid artery catheters at 0.083, 0.25, 0.5, 1, 2, 4, 7, 24 h. All blood samples will be transferred into microcentrifuge tubes containing 2 μL of $K_2EDTA$ (0.5M) as anti-coagulant and placed on wet ice. Then blood samples will be processed for plasma by centrifugation at approximately 4° C., 3000 g within half an hour of collection. Plasma samples will be stored in polypropylene tubes, quick frozen over dry ice and kept at −70±10° C. until LC/MS/MS analysis.

Pharmacokinetic parameters (mean±SD, n=3) of prodrugs and active forms in portal and carotid samples following oral administration of prodrugs (10 mg/kg) in portal vein cannulated rat were detected and analyzed. The test results of Example 1-B, 41-A, 41-B, 42-A and 43-A were summarized below.

TABLE 10

Pharmacokinetic parameters of Example 41-A and its corresponding active form Compound 41c-B in portal and carotid samples following oral administration of Example 41-A (10 mg/kg) in portal vein cannulated rat

| | Prodrug Example 41-A Corresponding Active Form Compound 41c-B | | | |
|---|---|---|---|---|
| | Portal sampling | | Carotid sampling | |
| PK parameter | prodrug | active form | prodrug | active form |
| $T_{max}$ (h) | 0.14 | 0.4 | 0.19 | 0.42 |
| $C_{max}$ (nM) | 9703 | 2223 | 210 | 2185 |
| $AUC_{0-2}$ (nM · h) | 2188 | 2246 | 114 | 2108 |
| $AUC_{active}/AUC_{total}$ | 51% | | 95% | |

TABLE 11

Pharmacokinetic parameters of Example 43-A and its corresponding active form Compound 43e-A in portal and carotid samples following oral administration of Example 43-A (10 mg/kg) in portal vein cannulated rat

| | Prodrug Example 43-A Corresponding Active Form Compound 43e-A | | | |
|---|---|---|---|---|
| | Portal sampling | | Carotid sampling | |
| PK parameter | prodrug | active form | prodrug | active form |
| $T_{max}$ (h) | 0.28 | 0.33 | 0.22 | 0.28 |
| $C_{max}$ (nM) | 4110 | 818 | 191 | 691 |
| $AUC_{0-2}$ (nM · h) | 2067 | 679 | 124 | 564 |
| $AUC_{active}/AUC_{total}$ | 25% | | 82% | |

TABLE 12

Pharmacokinetic parameters of Example 1-B and its corresponding active form Compound 1e-A in portal and systemic samples following oral administration of Example 1-B (10 mg/kg) in portal vein cannulated rat

| | Prodrug Example 1-B Corresponding Active Form Compound 1e-A | | | |
|---|---|---|---|---|
| | Portal sampling | | Carotid sampling | |
| PK parameter | prodrug | active form | prodrug | active form |
| $T_{max}$ (h) | 0.083 | 0.25 | 0.083 | 0.5 |
| $C_{max}$ (nM) | 670 | 192 | 70 | 174 |
| $AUC_{0-2}$ (nM · h) | 266 | 164 | 40 | 184 |
| $AUC_{active}/AUC_{total}$ | 38% | | 82% | |

TABLE 13

Pharmacokinetic parameters of Example 42-A and its corresponding active form Compound 41c-A in portal and carotid samples following oral administration of Example 42-A (10 mg/kg) in portal vein cannulated rat

| | Prodrug Example 42-A Corresponding Active Form Compound 41c-A | | | |
|---|---|---|---|---|
| | Portal sampling | | Carotid sampling | |
| PK parameter | prodrug | active form | prodrug | active form |
| $T_{max}$ (h) | 0.19 | 0.42 | 0.22 | 0.36 |
| $C_{max}$ (nM) | 8917 | 3162 | 286 | 3326 |
| $AUC_{0-2}$ (nM · h) | 3461 | 3199 | 286 | 3326 |
| $AUC_{active}/AUC_{total}$ | 48% | | 96% | |

TABLE 14

Pharmacokinetic parameters of Example 41-B and its corresponding active form Compound 41c-A in portal and carotid samples following oral administration of Example 41-B (10 mg/kg) in portal vein cannulated rat

| | Prodrug Example 41-B Corresponding Active Form Compound 41c-A | | | |
|---|---|---|---|---|
| | Portal sampling | | Carotid sampling | |
| PK parameter | prodrug | active form | prodrug | active form |
| $T_{max}$ (h) | 0.19 | 0.5 | 0.25 | 0.5 |
| $C_{max}$ (nM) | 7068 | 3315 | 29.6 | 3432 |
| $AUC_{0-2}$ (nM · h) | 1444 | 3211 | 22.5 | 3301 |
| $AUC_{active}/AUC_{total}$ | | 69% | | 99% |

Based on the above results, it was concluded that the primary site of conversion of prodrug was liver rather than intestine, because $AUC_{active}/AUC_{total}$ was higher in sampling from carotid artery compared to $AUC_{active}/AUC_{total}$ in sampling from portal vein.

The invention claimed is:

1. A compound of formula (I),

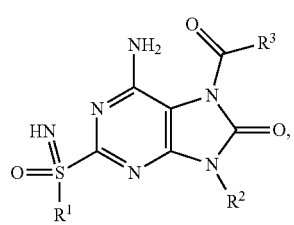

(I)

wherein
R[1] is $C_{1-6}$alkyl;
R[2] is benzyl, said benzyl being unsubstituted or substituted by one, two or three substituents independently selected from halogen and $C_{1-6}$alkyl;
R[3] is —NR[4]R[5], wherein
R[4] is $C_{1-6}$alkyl or $C_{1-6}$alkoxy$C_{1-6}$alkyl; and
R[5] is $(C_{1-6}alkyl)_2NCOOC_{1-6}$alkyl, $C_{1-6}$alkoxy$C_{1-6}$alkyl, $C_{1-6}$alkoxycarbonyl($C_{1-6}$alkyl)amino$C_{1-6}$alkyl, $C_{1-6}$alkoxycarbonyl(phenyl)$C_{1-6}$alkyl, $C_{1-6}$alkoxycarbonyl$C_{1-6}$alkyl, $C_{1-6}$alkoxycarbonyloxy$C_{1-6}$alkyl, $C_{1-6}$alkyl, $C_{1-6}$alkylcarbonyl($C_{1-6}$alkyl)amino$C_{1-6}$alkyl or pyrrolidinylcarbamoyloxy$C_{1-6}$alkyl; or
R[4] and R[5] together with the nitrogen they are attached to form a heterocyclyl;
or a pharmaceutically acceptable salt, enantiomer or diastereomer thereof;
with the proviso that
6-amino-9-benzyl-2-(propylsulfonimidoyl)-7-(pyrrolidine-1-carbonyl)purin-8-one;
6-amino-9-benzyl-7-(piperidine-1-carbonyl)-2-(propylsulfonimidoyl)purin-8-one;
6-amino-9-benzyl-7-(morpholine-4-carbonyl)-2-(propylsulfonimidoyl)purin-8-one;
6-amino-9-benzyl-7-(3,3-dimethylpyrrolidine-1-carbonyl)-2-(propylsulfonimidoyl)purin-8-one;
ethyl 1-[6-amino-9-benzyl-8-oxo-2-(propylsulfonimidoyl)purine-7-carbonyl]pyrrolidine-2-carboxylate;
6-amino-7-(2-azaspiro[3.3]heptane-2-carbonyl)-9-benzyl-2-(propylsulfonimidoyl)purin-8-one;
6-amino-9-benzyl-7-(2-oxa-6-azaspiro[3.3]heptane-6-carbonyl)-2-(propylsulfonimidoyl)purin-8-one;
6-amino-9-benzyl-7-(3,3-difluoropyrrolidine-1-carbonyl)-2-(propylsulfonimidoyl)purin-8-one; and
6-amino-9-benzyl-7-(3-fluoro-3-methyl-pyrrolidine-1-carbonyl)-2-(propylsulfonimidoyl)purin-8-one;

and their enantiomers and diastereomers are excluded.

2. A compound according to claim 1, wherein
$R^1$ is $C_{1-6}$alkyl;
$R^2$ is benzyl, said benzyl being unsubstituted or substituted by halogen or $C_{1-6}$alkyl;
$R^3$ is azetidinyl; piperazinyl substituted by $C_{1-6}$alkyl; piperidinyl substituted by piperidinyl; pyrrolidinyl; or —$NR^4R^5$, wherein
$R^4$ is $C_{1-6}$alkyl or $C_{1-6}$alkoxy$C_{1-6}$alkyl; and
$R^5$ is $(C_{1-6}$alkyl$)_2$NCOOC$_{1-6}$alkyl, $C_{1-6}$alkoxy$C_{1-6}$alkyl, $C_{1-6}$alkoxycarbonyl($C_{1-6}$alkyl)amino$C_{1-6}$alkyl, $C_{1-6}$alkoxycarbonyl(phenyl)$C_{1-6}$alkyl, $C_{1-6}$alkoxycarbonyl$C_{1-6}$alkyl, $C_{1-6}$alkoxycarbonyloxy$C_{1-6}$alkyl, $C_{1-6}$alkyl, $C_{1-6}$alkylcarbonyl($C_{1-6}$alkyl)amino$C_{1-6}$alkyl or pyrrolidinylcarbamoyloxy$C_{1-6}$alkyl;
or a pharmaceutically acceptable salt, enantiomer or diastereomer thereof.

3. A compound according to claim 1, wherein
$R^1$ is ethyl or propyl;
$R^2$ is benzyl, bromobenzyl, chlorobenzyl, fluorobenzyl or methylbenzyl;
$R^3$ is azetidinyl; 4-methylpiperazinyl; piperidinylpiperidinyl; pyrrolidinyl; or —$NR^4R^5$, wherein
$R^4$ is methyl, ethyl, propyl or methoxyethyl; and
$R^5$ is acetyl(methyl)aminoethyl, butyl, butyl(methyl)carbamoyloxyethyl, diethylcarbamoyloxyethyl, ethoxycarbonyl(methyl)aminoethyl, ethoxycarbonylethyl, ethoxycarbonylisobutyl, ethoxycarbonylisopentyl, ethoxycarbonylmethyl, ethoxycarbonyloxyethyl, ethoxycarbonyl(phenyl)ethyl, ethyl, isobutyl, isopropoxycarbonylisopentyl, isopropoxycarbonyl(phenyl)ethyl, isopropyl, methoxycarbonyl(methyl)aminoethyl, methoxyethyl, methoxypropyl, propyl, propyl(methyl)carbamoyloxyethyl, pyrrolidinylcarbamoyloxyethyl, tert-butoxycarbonyl(methyl)aminoethyl, tert-butoxycarbonylethyl, tert-butoxycarbonylisopentyl or tert-butoxycarbonyl(phenyl)ethyl;
or a pharmaceutically acceptable salt, enantiomer or diastereomer thereof.

4. A compound according to claim 3, wherein $R^3$ is azetidinyl, 4-methylpiperazinyl, piperidinylpiperidinyl, pyrrolidinyl, acetyl(methyl)aminoethyl(methyl)amino, bis(methoxyethyl)amino, butyl(ethyl)amino, butyl(methyl)amino, butyl(methyl)carbamoyloxyethyl(methyl)amino, diethylcarbamoyloxyethyl(methyl)amino, ethoxycarbonyl(methyl)aminoethyl(methyl)amino, ethoxycarbonylethyl(methyl)amino, ethoxycarbonylisobutyl(methyl)amino, ethoxycarbonylisopentyl(methyl)amino, ethoxycarbonylmethyl(methyl)amino, ethoxycarbonyloxyethyl(methyl)amino, ethoxycarbonyl(phenyl)ethyl(methyl)amino, ethyl(methyl)amino, isobutyl(methyl)amino, isopropoxycarbonylisopentyl(methyl)amino, isopropoxycarbonyl(phenyl)ethyl(methyl)amino, isopropyl(methyl)amino, methoxycarbonyl(methyl)aminoethyl(methyl)amino, methoxyethyl(ethyl)amino, methoxyethyl(methyl)amino, methoxyethyl(propyl)amino, methoxypropyl(methyl)amino, propyl(ethyl)amino, propyl(methyl)amino, propyl(methyl)carbamoyloxyethyl(methyl)amino, pyrrolidinylcarbamoyloxyethyl(methyl)amino, tert-butoxycarbonyl(methyl)aminoethyl(methyl)amino, tert-butoxycarbonylethyl(methyl)amino, tert-butoxycarbonylisopentyl(methyl)amino or tert-butoxycarbonyl(phenyl)ethyl(methyl)amino; or a pharmaceutically acceptable salt, enantiomer or diastereomer thereof.

5. A compound according to claim 1, wherein $R^1$ is ethyl; or a pharmaceutically acceptable salt, enantiomer or diastereomer thereof.

6. A compound according to claim 1, wherein $R^2$ is benzyl substituted by halogen or $C_{1-6}$alkyl; or a pharmaceutically acceptable salt, enantiomer or diastereomer thereof.

7. A compound according to claim 1, wherein $R^2$ is bromobenzyl, chlorobenzyl, fluorobenzyl or methylbenzyl; or a pharmaceutically acceptable salt, enantiomer or diastereomer thereof.

8. A compound according to claim 7, wherein $R^2$ is bromobenzyl, chlorobenzyl or fluorobenzyl; or a pharmaceutically acceptable salt, enantiomer or diastereomer thereof.

9. A compound according to claim 1, wherein $R^3$ is —$NR^4R^5$, wherein $R^4$ is $C_{1-6}$alkyl, $R^5$ is $C_{1-6}$alkyl; or a pharmaceutically acceptable salt, enantiomer or diastereomer thereof.

10. A compound according to claim 9, wherein $R^3$ is propyl(methyl)amino or ethyl(methyl)amino; or a pharmaceutically acceptable salt, enantiomer or diastereomer thereof.

11. A compound according to claim 1, wherein
$R^1$ is $C_{1-6}$alkyl;
$R^2$ is benzyl, said benzyl being substituted by halogen or $C_{1-6}$alkyl; and
$R^3$ is —$NR^4R^5$, wherein $R^4$ is $C_{1-6}$alkyl, and $R^5$ is $C_{1-6}$alkyl;
or a pharmaceutically acceptable salt, enantiomer or diastereomer thereof.

12. A compound according to claim 11, wherein
$R^1$ is ethyl;
$R^2$ is methylbenzyl, bromobenzyl, chlorobenzyl or fluorobenzyl; and
$R^3$ is propyl(methyl)amino or ethyl(methyl)amino;
or a pharmaceutically acceptable salt, enantiomer or diastereomer thereof.

13. A compound selected from:
6-Amino-9-benzyl-N-methyl-8-oxo-N-propyl-2-(propylsulfonimidoyl)purine-7-carboxamide;
6-Amino-9-benzyl-N-(2-methoxyethyl)-N-methyl-8-oxo-2-(propylsulfonimidoyl)purine-7-carboxamide;
6-Amino-9-benzyl-N-ethyl-8-oxo-N-propyl-2-(propylsulfonimidoyl)purine-7-carboxamide;
6-Amino-9-benzyl-7-[4-(1-piperidyl)piperidine-1-carbonyl]-2-(propylsulfonimidoyl)purin-8-one;
6-Amino-9-benzyl-N-ethyl-N-(2-methoxyethyl)-8-oxo-2-(propylsulfonimidoyl)purine-7-carboxamide;
6-Amino-9-benzyl-N-butyl-N-ethyl-8-oxo-2-(propylsulfonimidoyl)purine-7-carboxamide;
6-Amino-9-benzyl-N-(2-methoxyethyl)-8-oxo-N-propyl-2-(propylsulfonimidoyl)purine-7-carboxamide;
6-Amino-9-benzyl-N,N-bis(2-methoxyethyl)-8-oxo-2-(propylsulfonimidoyl)purine-7-carboxamide;
6-Amino-7-(azetidine-1-carbonyl)-9-benzyl-2-(propylsulfonimidoyl)purin-8-one;
6-Amino-9-benzyl-N-isopropyl-N-methyl-8-oxo-2-(propylsulfonimidoyl)purine-7-carboxamide;
6-Amino-9-benzyl-7-(4-methylpiperazine-1-carbonyl)-2-(propylsulfonimidoyl)purin-8-one;
6-Amino-9-benzyl-N-(3-methoxypropyl)-N-methyl-8-oxo-2-(propylsulfonimidoyl)purine-7-carboxamide;
6-Amino-9-benzyl-N-isobutyl-N-methyl-8-oxo-2-(propylsulfonimidoyl)purine-7-carboxamide;
Ethyl 2-[[6-amino-9-benzyl-8-oxo-2-(propylsulfonimidoyl)purine-7-carbonyl]-methyl-amino]acetate;

Ethyl 3-[[6-amino-9-benzyl-8-oxo-2-(propylsulfonimidoyl)purine-7-carbonyl]-methyl-amino]propanoate;
tert-Butyl 3-[[6-amino-9-benzyl-8-oxo-2-(propylsulfonimidoyl)purine-7-carbonyl]-methyl-amino]propanoate;
Ethyl (2S)-2-[[6-amino-9-benzyl-8-oxo-2-(propylsulfonimidoyl)purine-7-carbonyl]-methyl-amino]propanoate;
tert-Butyl (2S)-2-[[6-amino-9-benzyl-8-oxo-2-(propylsulfonimidoyl)purine-7-carbonyl]-methyl-amino]-4-methyl-pentanoate;
Isopropyl (2S)-2-[[6-amino-9-benzyl-8-oxo-2-(propylsulfonimidoyl)purine-7-carbonyl]-methyl-amino]-4-methyl-pentanoate;
Ethyl (2S)-2-[[6-amino-9-benzyl-8-oxo-2-(propylsulfonimidoyl)purine-7-carbonyl]-methyl-amino]-3-methyl-butanoate;
Ethyl (2S)-2-[[6-amino-9-benzyl-8-oxo-2-(propylsulfonimidoyl)purine-7-carbonyl]-methyl-amino]-4-methyl-pentanoate;
Ethyl (2S)-2-[[6-amino-9-benzyl-8-oxo-2-(propylsulfonimidoyl)purine-7-carbonyl]-methyl-amino]-3-phenyl-propanoate;
Isopropyl (2S)-2-[[6-amino-9-benzyl-8-oxo-2-(propylsulfonimidoyl)purine-7-carbonyl]-methyl-amino]-3-phenyl-propanoate;
tert-Butyl (2S)-2-[[6-amino-9-benzyl-8-oxo-2-(propylsulfonimidoyl)purine-7-carbonyl]-methyl-amino]-3-phenyl-propanoate;
N-[2-[Acetyl(methyl)amino]ethyl]-6-amino-9-benzyl-N-methyl-8-oxo-2-(propylsulfonimidoyl)purine-7-carboxamide;
Methyl N-[2-[[6-amino-9-benzyl-8-oxo-2-(propylsulfonimidoyl)purine-7-carbonyl]-methyl-amino]ethyl]-N-methyl-carbamate;
tert-Butyl N-[2-[[6-amino-9-benzyl-8-oxo-2-(propylsulfonimidoyl)purine-7-carbonyl]-methyl-amino]ethyl]-N-methyl-carbamate;
Ethyl N-[2-[[6-amino-9-benzyl-8-oxo-2-(propylsulfonimidoyl)purine-7-carbonyl]-methyl-amino]ethyl]-N-methyl-carbamate;
2-[[6-Amino-9-benzyl-8-oxo-2-(propylsulfonimidoyl)purine-7-carbonyl]-methyl-amino]ethyl N-butyl-N-methyl-carbamate;
2-[[6-Amino-9-benzyl-8-oxo-2-(propylsulfonimidoyl)purine-7-carbonyl]-methyl-amino]ethyl pyrrolidine-1-carboxylate;
2-[[6-Amino-9-benzyl-8-oxo-2-(propylsulfonimidoyl)purine-7-carbonyl]-methyl-amino]ethyl N-methyl-N-propyl-carbamate;
2-[[6-Amino-9-benzyl-8-oxo-2-(propylsulfonimidoyl)purine-7-carbonyl]-methyl-amino]ethyl N,N-diethylcarbamate;
2-[[6-Amino-9-benzyl-8-oxo-2-(propylsulfonimidoyl)purine-7-carbonyl]-methyl-amino]ethyl ethyl carbonate;
6-Amino-N-butyl-9-[(4-chlorophenyl)methyl]-N-methyl-8-oxo-2-[S(S)-propylsulfonimidoyl]purine-7-carboxamide;
6-amino-N-butyl-9-[(4-chlorophenyl)methyl]-N-methyl-8-oxo-2-[S(S)-propylsulfonimidoyl]purine-7-carboxamide;
6-Amino-9-[(4-chlorophenyl)methyl]-N-ethyl-N-methyl-8-oxo-2-(propylsulfonimidoyl)purine-7-carboxamide;
6-Amino-N-methyl-8-oxo-N-propyl-2[S(S)-propylsulfonimidoyl]-9-(p-tolylmethyl)purine-7-carboxamide;
6-Amino-N-methyl-8-oxo-N-propyl-2[S(R)-propylsulfonimidoyl]-9-(p-tolylmethyl)purine-7-carboxamide;
6-Amino-2-[S(S)-propylsulfonimidoyl]-9-(p-tolylmethyl)-7-(pyrrolidine-1-carbonyl)purin-8-one;
6-Amino-2-[S(R)-propylsulfonimidoyl]-9-(p-tolylmethyl)-7-(pyrrolidine-1-carbonyl)purin-8-one;
6-Amino-N-(2-methoxyethyl)-N-methyl-8-oxo-2-[S(S)-propylsulfonimidoyl]-9-(p-tolylmethyl)purine-7-carboxamide;
6-Amino-N-(2-methoxyethyl)-N-methyl-8-oxo-2-[S(R)-propylsulfonimidoyl]-9-(p-tolylmethyl)purine-7-carboxamide;
6-Amino-N-ethyl-N-methyl-8-oxo-2-(propylsulfonimidoyl)-9-(p-tolylmethyl)purine-7-carboxamide;
6-Amino-N-butyl-N-methyl-8-oxo-2-(propylsulfonimidoyl)-9-(p-tolylmethyl)purine-7-carboxamide;
6-Amino-9-[(4-chlorophenyl)methyl]-2-[S(R)-ethylsulfonimidoyl]-N-methyl-8-oxo-N-propyl-purine-7-carboxamide;
6-Amino-9-[(4-chlorophenyl)methyl]-2-[S(S)-ethylsulfonimidoyl]-N-methyl-8-oxo-N-propyl-purine-7-carboxamide;
6-Amino-9-[(4-chlorophenyl)methyl]-N-ethyl-2[S(S)-ethylsulfonimidoyl]-N-methyl-8-oxo-purine-7-carboxamide;
6-Amino-9-[(4-chlorophenyl)methyl]-N-ethyl-2-[S(R)-ethylsulfonimidoyl]-N-methyl-8-oxo-purine-7-carboxamide;
6-Amino-2-[S(S)-ethylsulfonimidoyl]-N-methyl-8-oxo-N-propyl-9-(p-tolylmethyl)purine-7-carboxamide;
6-Amino-2-[S(R)-ethylsulfonimidoyl]-N-methyl-8-oxo-N-propyl-9-(p-tolylmethyl)purine-7-carboxamide;
6-Amino-N-ethyl-2[S(S)-ethylsulfonimidoyl]-N-methyl-8-oxo-9-(p-tolylmethyl)purine-7-carboxamide;
6-Amino-N-ethyl-2-[S(R)-ethylsulfonimidoyl]-N-methyl-8-oxo-9-(p-tolylmethyl)purine-7-carboxamide;
6-Amino-2-[S(S)ethylsulfonimidoyl]-9-[(4-fluorophenyl)methyl]-N-methyl-8-oxo-N-propyl-purine-7-carboxamide;
6-Amino-2-[S(R)ethylsulfonimidoyl]-9-[(4-fluorophenyl)methyl]-N-methyl-8-oxo-N-propyl-purine-7-carboxamide;
6-Amino-N-ethyl-2-(ethylsulfonimidoyl)-9-[(4-fluorophenyl)methyl]-N-methyl-8-oxo-purine-7-carboxamide;
6-Amino-N-ethyl-2-[S(S)-(ethylsulfonimidoyl)]-9-[(4-fluorophenyl)methyl]-N-methyl-8-oxo-purine-7-carboxamide;
6-Amino-N-ethyl-2-[S(R)-(ethylsulfonimidoyl)]-9-[(4-fluorophenyl)methyl]-N-methyl-8-oxo-purine-7-carboxamide;
6-Amino-9-[(4-bromophenyl)methyl]-2-(ethylsulfonimidoyl)-N-methyl-8-oxo-N-propyl-purine-7-carboxamide;
6-Amino-2-[S(R)-ethylsulfonimidoyl]-9-[(4-bromophenyl)methyl]-N-methyl-8-oxo-N-propyl-purine-7-carboxamide;
6-Amino-2-[S(S)-ethylsulfonimidoyl]-9-[(4-bromophenyl)methyl]-N-methyl-8-oxo-N-propyl-purine-7-carboxamide;
6-Amino-9-[(4-bromophenyl)methyl]-N-ethyl-2-(ethylsulfonimidoyl)-N-methyl-8-oxo-purine-7-carboxamide;
6-Amino-9-[(4-bromophenyl)methyl]-N-ethyl-2-[S(S)-(ethylsulfonimidoyl)]-N-methyl-8-oxo-purine-7-carboxamide; and
6-Amino-9-[(4-bromophenyl)methyl]-N-ethyl-2-[S(R)-(ethylsulfonimidoyl)]-N-methyl-8-oxo-purine-7-carboxamide;
or a pharmaceutically acceptable salt, enantiomer or diastereomer thereof.

14. A compound according to claim 13, selected from:
6-Amino-9-benzyl-N-methyl-8-oxo-N-propyl-2-(propylsulfonimidoyl)purine-7-carboxamide;
6-Amino-9-[(4-chlorophenyl)methyl]-2-[S(R)-ethylsulfonimidoyl]-N-methyl-8-oxo-N-propyl-purine-7-carboxamide;
6-Amino-9-[(4-chlorophenyl)methyl]-2-[S(S)-ethylsulfonimidoyl]-N-methyl-8-oxo-N-propyl-purine-7-carboxamide;
6-Amino-9-[(4-chlorophenyl)methyl]-N-ethyl-2[S(S)-ethylsulfonimidoyl]-N-methyl-8-oxo-purine-7-carboxamide;
6-Amino-9-[(4-chlorophenyl)methyl]-N-ethyl-2-[S(R)-ethylsulfonimidoyl]-N-methyl-8-oxo-purine-7-carboxamide;
6-Amino-2-[S(S)-ethylsulfonimidoyl]-N-methyl-8-oxo-N-propyl-9-(p-tolylmethyl)purine-7-carboxamide;
6-Amino-2-[S(R)-ethylsulfonimidoyl]-N-methyl-8-oxo-N-propyl-9-(p-tolylmethyl)purine-7-carboxamide;
6-Amino-N-ethyl-2[S(S)-ethylsulfonimidoyl]-N-methyl-8-oxo-9-(p-tolylmethyl)purine-7-carboxamide;
6-Amino-N-ethyl-2-[S(R)-ethylsulfonimidoyl]-N-methyl-8-oxo-9-(p-tolylmethyl)purine-7-carboxamide;
6-amino-2-(ethylsulfonimidoyl)-9-[(4-fluorophenyl)methyl]-N-methyl-8-oxo-N-propyl-purine-7-carboxamide;
6-Amino-2-[S(S)ethylsulfonimidoyl]-9-[(4-fluorophenyl)methyl]-N-methyl-8-oxo-N-propyl-purine-7-carboxamide; and
6-Amino-2-[S(R)ethylsulfonimidoyl]-9-[(4-fluorophenyl)methyl]-N-methyl-8-oxo-N-propyl-purine-7-carboxamide;
or a pharmaceutically acceptable salt, enantiomer or diastereomer thereof.

15. A process for the preparation of a compound according to claim 1 comprising the following step:
the reaction of a compound of formula (II),

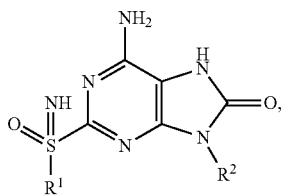

(II)

with carbamoyl chloride in the presence of a mixed base;
wherein the mixed base is pyridine and triethylamine, pyridine and DIPEA, DMAP and triethylamine, or DMAP and DIPEA.

16. A pharmaceutical composition comprising a compound according to claim 1, or a pharmaceutically acceptable salt, enantiomer or diastereomer thereof, and a therapeutically inert carrier.

17. A compound which is 6-Amino-9-[(4-chlorophenyl)methyl]-2-[S(R)-ethylsulfonimidoyl]-N-methyl-8-oxo-N-propyl-purine-7-carboxamide, or a pharmaceutically acceptable salt thereof.

18. A compound which is 6-amino-9-[(4-chlorophenyl)methyl]-2-[S(S)-ethylsulfonimidoyl]-N-methyl-8-oxo-N-propyl-purine-7-carboxamide, or a pharmaceutically acceptable salt thereof.

19. A compound which is 6-Amino-9-[(4-chlorophenyl)methyl]-N-ethyl-2[S(S)-ethylsulfonimidoyl]-N-methyl-8-oxo-purine-7-carboxamide, or a pharmaceutically acceptable salt thereof.

20. A compound which is 6-Amino-9-[(4-chlorophenyl)methyl]-N-ethyl-2-[S(R)-ethylsulfonimidoyl]-N-methyl-8-oxo-purine-7-carboxamide, or a pharmaceutically acceptable salt thereof.

21. A compound which is 6-Amino-N-ethyl-2[S(S)-ethylsulfonimidoyl]-N-methyl-8-oxo-9-(p-tolylmethyl)purine-7-carboxamide, or a pharmaceutically acceptable salt thereof.

22. A compound which is 6-Amino-N-ethyl-2-[S(R)-ethylsulfonimidoyl]-N-methyl-8-oxo-9-(p-tolylmethyl)purine-7-carboxamide, or a pharmaceutically acceptable salt thereof.

23. A compound which is 6-Amino-9-[(4-bromophenyl)methyl]-2-(ethylsulfonimidoyl)-N-methyl-8-oxo-N-propyl-purine-7-carboxamide, or a pharmaceutically acceptable salt thereof.

24. A compound which is 6-amino-2-[S(R)-ethylsulfonimidoyl]-9-[(4-bromophenyl)methyl]-N-methyl-8-oxo-N-propyl-purine-7-carboxamide, or a pharmaceutically acceptable salt thereof.

25. A compound which is 6-amino-2-[S(S)-ethylsulfonimidoyl]-9-[(4-bromophenyl)methyl]-N-methyl-8-oxo-N-propyl-purine-7-carboxamide, or a pharmaceutically acceptable salt thereof.

26. A compound which is 6-Amino-9-[(4-bromophenyl)methyl]-N-ethyl-2-(ethylsulfonimidoyl)-N-methyl-8-oxo-purine-7-carboxamide, or a pharmaceutically acceptable salt thereof.

27. A compound which is 6-amino-9-[(4-bromophenyl)methyl]-N-ethyl-2-[S(S)-(ethylsulfonimidoyl)]-N-methyl-8-oxo-purine-7-carboxamide, or a pharmaceutically acceptable salt thereof.

28. A compound which is 6-amino-9-[(4-bromophenyl)methyl]-N-ethyl-2-[S(R)-(ethylsulfonimidoyl)]-N-methyl-8-oxo-purine-7-carboxamide, or a pharmaceutically acceptable salt thereof.

29. A method for the treatment of hepatitis B virus infection, which method comprises administering a therapeutically effective amount of a compound according to claim 1, or a pharmaceutically acceptable salt, enantiomer or diastereomer thereof.

30. A method for agonizing TLR7, which method comprises administering a therapeutically effective amount of a compound according to claim 1, or a pharmaceutically acceptable salt, enantiomer or diastereomer thereof.

31. A method for inducing production of interferon-α, which method comprises administering a therapeutically effective amount of a compound according to claim 1, or a pharmaceutically acceptable salt, enantiomer or diastereomer thereof.

* * * * *